(12) United States Patent
Carr et al.

(10) Patent No.: US 7,264,806 B2
(45) Date of Patent: Sep. 4, 2007

(54) MODIFIED ANTI-CD52 ANTIBODY

(75) Inventors: Francis J. Carr, Balmedie (GB); Anita A. Hamilton, Aberdeen (GB)

(73) Assignee: Biovation Ltd., Aberdeen (GB)

( * ) Notice: Subject to any disclaimer, the term of this patent is extended or adjusted under 35 U.S.C. 154(b) by 64 days.

(21) Appl. No.: 10/977,369

(22) Filed: Oct. 29, 2004

(65) Prior Publication Data

US 2005/0152898 A1 Jul. 14, 2005

Related U.S. Application Data

(60) Provisional application No. 60/516,210, filed on Nov. 1, 2003.

(51) Int. Cl.
C07H 21/00 (2006.01)
C07K 16/00 (2006.01)
C12N 5/06 (2006.01)
A61K 39/395 (2006.01)
C12P 21/06 (2006.01)

(52) U.S. Cl. .............................. 424/144.1; 424/320.1; 530/388.22; 536/23.53

(58) Field of Classification Search .................... None
See application file for complete search history.

(56) References Cited

U.S. PATENT DOCUMENTS

| 6,569,430 | B1 * | 5/2003 | Waldmann et al. ...... 424/133.1 |
| 6,982,321 | B2 * | 1/2006 | Winter ..................... 530/387.3 |
| 2003/0153043 | A1 | 8/2003 | Carr et al. ................. 435/69.1 |
| 2003/0157641 | A1 * | 8/2003 | Reff et al. ................. 435/69.1 |
| 2004/0180386 | A1 * | 9/2004 | Carr et al. ................. 435/7.21 |

FOREIGN PATENT DOCUMENTS

| WO | WO92/01059 | * 1/1992 |
| WO | WO93/10817 | 6/1993 |
| WO | WO98/52976 | 11/1998 |
| WO | WO98/59244 | 12/1998 |
| WO | WO 00/34317 | 6/2000 |
| WO | WO 02/30460 | 4/2002 |

OTHER PUBLICATIONS

Rudikoff et al (Proc Natl Acad Sci USA 1982 vol. 79 1979-1983).*
Reichmann et al. (Nature 332:323-327 1988).*
Sequence search results for SEQ ID Nos.: 1 (pp. 1-5) and 2 (pp. 1-5).*
VH and VL domain map for SEQ ID Nos.: 1 and 2 (1 page).*
Asano et al. (J Biochem (Tokyo). Dec. 2002;132(6):903-9).*
Takeda et al. (Hybridoma. Feb. 1995;14(1):9-18).*
Cheung et al. (J Virol. Nov. 1992;66(11):6714-20).*
Cobbold et al., "A simple method for measuring patient antiglobulin responses against isotypic or idiotypic determinants," *J. Immunol Methods*, 127:19-24, 1990.

(Continued)

Primary Examiner—Larry R. Helms
Assistant Examiner—Lynn Bristol
(74) Attorney, Agent, or Firm—Fulbright & Jaworski L.L.P.

(57) ABSTRACT

The present invention provides for modified forms of anti-CD52 antibodies with reduced numbers of potential T-cell epitopes that are expected to display decreased immunogenicity.

2 Claims, 39 Drawing Sheets

OTHER PUBLICATIONS

Dyer, "Effects of CAMPATH-1 antibodies in vivo in patients with lymphoid malignancies: influence of antibody isotype," *Blood*, 73:1431-1439, 1989.

Friend et al., "Reversal of allograft rejection using the monoclonal antibody, campath-1G," *Transplant. Proc*, 23:2253-2254, 1991.

Hale et al., "Improving the outcome of bone marrow transplantation by using CD52 monoclonal antibodies to prevent graft-versus-host disease and graft rejection," *Blood*, 92:4581-4590, 1998.

Hale et al., "Removal of t cells from bone marrow for transplantation: a monoclonal antilymphocyte antibody that fixes human complement," *Blood*, 62:873-882, 1983.

Riechmann et al., "Reshaping human antibodies for therapy," *Nature*, 332:323-327, 1988.

Schnitzer et al., "Subcutaneous administration of campath-1h: clinical and biological outcomes," *J. Rheumatol*, 24:1031-1036, 1997.

Weinblatt et al., "CAMPATH-1H, a humanized monoclonal antibody, in refractory rheumatoid arthritis," *Arthritis Rheum*, 38:1589-1594, 1995.

Dyer, "The Role of CAMPATH-I Antibodies in the Treatment of Lymphoid Malignancies," *Seminars in Oncology*, 26:52-57, 1999.

\* cited by examiner

SEQUENCE LISTING

<160> NUMBER OF SEQ ID NOS: 231

<210> SEQ ID NO 1
<211> LENGTH: 121
<212> TYPE: PRT
<213> ORGANISM: Rattus norvegicus

<400> SEQUENCE: 1

```
Glu Val Lys Leu Leu Glu Ser Gly Gly Gly Leu Val Gln Pro Gly Gly
1               5                   10                  15

Ser Met Arg Leu Ser Cys Ala Gly Ser Gly Phe Thr Phe Thr Asp Phe
            20                  25                  30

Tyr Met Asn Trp Ile Arg Gln Pro Ala Gly Lys Ala Pro Glu Trp Leu
        35                  40                  45

Gly Phe Ile Arg Asp Lys Ala Lys Gly Tyr Thr Thr Glu Tyr Asn Pro
    50                  55                  60

Ser Val Lys Gly Arg Phe Thr Ile Ser Arg Asp Asn Thr Gln Asn Met
65                  70                  75                  80

Leu Tyr Leu Gln Met Asn Thr Leu Arg Ala Glu Asp Thr Ala Thr Tyr
                85                  90                  95

Tyr Cys Ala Arg Glu Gly His Thr Ala Ala Pro Phe Asp Tyr Trp Gly
            100                 105                 110

Gln Gly Val Met Val Thr Val Ser Ser
        115                 120
```

<210> SEQ ID NO 2
<211> LENGTH: 107
<212> TYPE: PRT
<213> ORGANISM: Rattus norvegicus

<400> SEQUENCE: 2

```
Asp Ile Lys Met Thr Gln Ser Pro Ser Phe Leu Ser Ala Ser Val Gly
1               5                   10                  15

Asp Arg Val Thr Leu Asn Cys Lys Ala Ser Gln Asn Ile Asp Lys Tyr
            20                  25                  30

Leu Asn Trp Tyr Gln Gln Lys Leu Gly Glu Ser Pro Lys Leu Leu Ile
        35                  40                  45

Tyr Asn Thr Asn Asn Leu Gln Thr Gly Ile Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Phe Cys Leu Gln His Ile Ser Arg Pro Arg
                85                  90                  95

Thr Phe Gly Thr Gly Thr Lys Leu Glu Leu Lys
            100                 105
```

<210> SEQ ID NO 3
<211> LENGTH: 121
<212> TYPE: PRT
<213> ORGANISM: Artificial

```
<220> FEATURE:
<223> OTHER INFORMATION: Mutated recombinant

<400> SEQUENCE: 3

Glu Val Gln Leu Leu Glu Ser Gly Gly Gly Leu Val Gln Pro Gly Gly
1               5                   10                  15

Ser Leu Arg Leu Ser Cys Ala Gly Ser Gly Phe Thr Phe Thr Asp Phe
            20                  25                  30

Tyr Met Asn Trp Val Arg Gln Ala Pro Gly Lys Gly Leu Glu Trp Val
        35                  40                  45

Gly Phe Ile Arg Asp Lys Ala Lys Gly Tyr Thr Thr Glu Tyr Asn Pro
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Glu Gly His Thr Ala Ala Pro Phe Asp Tyr Trp Gly
            100                 105                 110

Gln Gly Thr Leu Val Thr Val Ser Ser
        115                 120

<210> SEQ ID NO 4
<211> LENGTH: 121
<212> TYPE: PRT
<213> ORGANISM: Artificial
<220> FEATURE:
<223> OTHER INFORMATION: Mutated recombinant

<400> SEQUENCE: 4

Glu Val Gln Leu Leu Glu Ser Gly Gly Gly Leu Val Gln Pro Gly Gly
1               5                   10                  15

Ser Leu Arg Leu Ser Cys Ala Gly Ser Gly Phe Thr Phe Thr Asp Phe
            20                  25                  30

Tyr Met Asn Trp Ile Arg Gln Pro Pro Gly Lys Ala Pro Glu Trp Ile
        35                  40                  45

Gly Phe Ile Arg Asp Lys Ala Lys Gly Tyr Thr Thr Glu Tyr Asn Pro
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Glu Gly His Thr Ala Ala Pro Phe Asp Tyr Trp Gly
            100                 105                 110

Gln Gly Thr Leu Val Thr Val Ser Ser
        115                 120

<210> SEQ ID NO 5
<211> LENGTH: 121
<212> TYPE: PRT
<213> ORGANISM: Artificial
<220> FEATURE:
<223> OTHER INFORMATION: Mutated Recombinant

<400> SEQUENCE: 5

Glu Val Lys Leu Gln Glu Ser Gly Gly Gly Leu Val Gln Pro Gly Gly
1               5                   10                  15

Ser Met Arg Ile Ser Cys Ser Gly Ser Gly Phe Thr Phe Thr Asp Phe
            20                  25                  30
```

```
Tyr Met Asn Trp Ile Arg Gln Pro Pro Gly Lys Gly Pro Glu Trp Ile
            35                  40                  45

Gly Phe Ile Arg Asp Lys Ala Lys Gly Tyr Thr Thr Glu Tyr Asn Pro
        50                  55                  60

Ser Val Lys Gly Arg Phe Thr Ile Ser Arg Asp Asn Thr Gln Asn Thr
65                  70                  75                  80

Leu His Leu Gln Ala Asn Thr Leu Arg Ala Glu Asp Thr Ala Val Tyr
                85                  90                  95

Tyr Cys Ala Arg Glu Gly His Thr Ala Ala Pro Phe Asp Tyr Trp Gly
                100                 105                 110

Gln Gly Thr Thr Val Thr Val Ser Ser
            115                 120
```

<210> SEQ ID NO 6
<211> LENGTH: 121
<212> TYPE: PRT
<213> ORGANISM: Artificial
<220> FEATURE:
<223> OTHER INFORMATION: MUTATED RECOMBINANT

<400> SEQUENCE: 6

```
Glu Val Gln Leu Leu Glu Ser Gly Gly Gly Leu Val Gln Pro Gly Gly
1               5                   10                  15

Ser Leu Arg Leu Ser Cys Ala Gly Ser Gly Phe Thr Phe Thr Asp Phe
            20                  25                  30

Tyr Met Asn Trp Val Arg Gln Ala Pro Gly Lys Gly Leu Glu Trp Val
            35                  40                  45

Gly Phe Ile Arg Asp Lys Ala Lys Gly Tyr Thr Thr Glu Tyr Asn Pro
        50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Glu Gly His Thr Ala Ala Pro Phe Asp Tyr Trp Gly
                100                 105                 110

Gln Gly Thr Leu Val Thr Val Ser Ser
            115                 120
```

<210> SEQ ID NO 7
<211> LENGTH: 121
<212> TYPE: PRT
<213> ORGANISM: Artificial
<220> FEATURE:
<223> OTHER INFORMATION: Mutated Recombinant

<400> SEQUENCE: 7

```
Glu Val Gln Leu Leu Glu Ser Gly Gly Gly Leu Val Gln Pro Gly Gly
1               5                   10                  15

Ser Leu Arg Leu Ser Cys Ala Gly Ser Gly Phe Thr Phe Thr Asp Phe
            20                  25                  30

Tyr Met Asn Trp Ile Arg Gln Pro Pro Gly Lys Ala Pro Glu Trp Leu
            35                  40                  45

Gly Phe Ile Arg Asp Lys Ala Lys Gly Tyr Thr Thr Glu Tyr Asn Pro
        50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95
```

```
Tyr Cys Ala Arg Glu Gly His Thr Ala Ala Pro Phe Asp Tyr Trp Gly
            100                 105                 110
Gln Gly Thr Leu Val Thr Val Ser Ser
        115                 120

<210> SEQ ID NO 8
<211> LENGTH: 107
<212> TYPE: PRT
<213> ORGANISM: Artificial
<220> FEATURE:
<223> OTHER INFORMATION: MR

<400> SEQUENCE: 8

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Asn Ile Asp Lys Tyr
            20                  25                  30
Leu Asn Trp Tyr Gln Gln Lys Pro Gly Lys Ala Pro Lys Ser Leu Ile
        35                  40                  45
Tyr Asn Thr Asn Asn Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Ile Ala Thr Tyr Tyr Cys Leu Gln His Ile Ser Arg Pro Arg
                85                  90                  95
Thr Phe Gly Thr Gly Thr Lys Leu Glu Leu Lys
            100                 105

<210> SEQ ID NO 9
<211> LENGTH: 107
<212> TYPE: PRT
<213> ORGANISM: ARTIFICIAL
<220> FEATURE:
<223> OTHER INFORMATION: MR

<400> SEQUENCE: 9

Asp Ile Gln Met Thr Gln Ser Pro Ser Ser Leu Ser Ala Ser Val Gly
1               5                   10                  15
Asp Arg Val Thr Ile Thr Cys Lys Ala Ser Gln Asn Ile Asp Lys Tyr
            20                  25                  30
Leu Asn Trp Tyr Gln Gln Lys Pro Gly Lys Ala Pro Lys Leu Leu Ile
        35                  40                  45
Tyr Asn Thr Asn Asn Leu Gln Thr Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Ile Ala Thr Tyr Tyr Cys Leu Gln His Ile Ser Arg Pro Arg
                85                  90                  95
Thr Phe Gly Thr Gly Thr Lys Leu Glu Leu Lys
            100                 105

<210> SEQ ID NO 10
<211> LENGTH: 107
<212> TYPE: PRT
<213> ORGANISM: ARTIFICIAL
<220> FEATURE:
<223> OTHER INFORMATION: MR

<400> SEQUENCE: 10
```

-continued

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Asp Lys Tyr
            20                  25                  30

Leu Asn Trp Tyr Gln Gln Lys Pro Gly Lys Ala Pro Lys Leu Leu Ile
        35                  40                  45

Tyr Asn Thr Asn Asn Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Leu Gln His Ile Ser Arg Pro Arg
                85                  90                  95

Thr Phe Gly Thr Gly Thr Lys Leu Glu Leu Lys
            100                 105
```

<210> SEQ ID NO 11
<211> LENGTH: 107
<212> TYPE: PRT
<213> ORGANISM: ARTIFICIAL
<220> FEATURE:
<223> OTHER INFORMATION: MR

<400> SEQUENCE: 11

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Ile Asp Lys Tyr
            20                  25                  30

Leu Asn Trp Tyr Gln Gln Lys Pro Gly Lys Ala Pro Lys Ser Leu Ile
        35                  40                  45

Tyr Asn Thr Asn Asn Leu Gln Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Leu Gln His Ile Ser Arg Pro Arg
                85                  90                  95

Thr Phe Gly Thr Gly Thr Lys Leu Glu Leu Lys
            100                 105
```

<210> SEQ ID NO 12
<211> LENGTH: 107
<212> TYPE: PRT
<213> ORGANISM: ARTIFICIAL
<220> FEATURE:
<223> OTHER INFORMATION: MR

<400> SEQUENCE: 12

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Ile Asp Lys Tyr
            20                  25                  30

Leu Asn Trp Tyr Gln Gln Lys Pro Gly Lys Ser Pro Lys Leu Leu Ile
        35                  40                  45

Tyr Asn Thr Asn Asn Leu Gln Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Leu Gln His Ile Ser Arg Pro Arg
                85                  90                  95
```

Thr Phe Gly Thr Gly Thr Lys Leu Glu Leu Lys
            100                 105

<210> SEQ ID NO 13
<211> LENGTH: 121
<212> TYPE: PRT
<213> ORGANISM: ARTIFICIAL
<220> FEATURE:
<223> OTHER INFORMATION: MR

<400> SEQUENCE: 13

Glu Val Gln Leu Gln Glu Ser Gly Gly Gly Leu Val Gln Pro Gly Gly
1               5                   10                  15

Ser Leu Arg Leu Ser Cys Ala Gly Ser Gly Phe Thr Phe Thr Asp Phe
            20                  25                  30

Tyr Met Asn Trp Ile Arg Gln Pro Pro Gly Lys Ala Pro Glu Trp Ile
        35                  40                  45

Gly Phe Ile Arg Asp Lys Ala Lys Gly Tyr Thr Thr Glu Tyr Asn Pro
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Glu Gly His Thr Ala Ala Pro Phe Asp Tyr Trp Gly
            100                 105                 110

Gln Gly Thr Leu Val Thr Val Ser Ser
            115                 120

<210> SEQ ID NO 14
<211> LENGTH: 121
<212> TYPE: PRT
<213> ORGANISM: ARTIFICIAL
<220> FEATURE:
<223> OTHER INFORMATION: MR

<400> SEQUENCE: 14

Glu Val Gln Leu Gln Glu Ser Gly Gly Gly Leu Val Gln Pro Gly Gly
1               5                   10                  15

Ser Leu Arg Leu Ser Cys Ala Gly Ser Gly Phe Thr Phe Thr Asp Phe
            20                  25                  30

Tyr Met Asn Trp Val Arg Gln Ala Pro Gly Lys Gly Leu Glu Trp Val
        35                  40                  45

Gly Phe Ile Arg Asp Lys Ala Lys Gly Tyr Thr Thr Glu Tyr Asn Pro
    50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Glu Gly His Thr Ala Ala Pro Phe Asp Tyr Trp Gly
            100                 105                 110

Gln Gly Thr Leu Val Thr Val Ser Ser
            115                 120

<210> SEQ ID NO 15
<211> LENGTH: 121
<212> TYPE: PRT
<213> ORGANISM: ARTIFICIAL
<220> FEATURE:
<223> OTHER INFORMATION: MR

<400> SEQUENCE: 15

Glu Val Gln Leu Gln Glu Ser Gly Gly Gly Leu Val Gln Pro Gly Gly
1               5                   10                  15

Ser Leu Arg Leu Ser Cys Ala Gly Ser Gly Phe Thr Phe Thr Asp Phe
            20                  25                  30

Tyr Met Asn Trp Ile Arg Gln Pro Pro Gly Lys Ala Pro Glu Trp Leu
        35                  40                  45

Gly Phe Ile Arg Asp Lys Ala Lys Gly Tyr Thr Thr Glu Tyr Asn Pro
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Glu Gly His Thr Ala Ala Pro Phe Asp Tyr Trp Gly
            100                 105                 110

Gln Gly Thr Leu Val Thr Val Ser Ser
        115                 120

<210> SEQ ID NO 16
<211> LENGTH: 121
<212> TYPE: PRT
<213> ORGANISM: ARTIFICIAL
<220> FEATURE:
<223> OTHER INFORMATION: MR

<400> SEQUENCE: 16

Glu Val Gln Leu Leu Glu Ser Gly Gly Gly Leu Val Gln Pro Gly Gly
1               5                   10                  15

Ser Leu Arg Leu Ser Cys Ala Gly Ser Gly Phe Thr Phe Thr Asp Phe
            20                  25                  30

Tyr Met Asn Trp Val Arg Gln Pro Pro Gly Lys Ala Pro Glu Trp Ile
        35                  40                  45

Gly Phe Ile Arg Asp Lys Ala Lys Gly Tyr Thr Thr Glu Tyr Asn Pro
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Glu Gly His Thr Ala Ala Pro Phe Asp Tyr Trp Gly
            100                 105                 110

Gln Gly Thr Leu Val Thr Val Ser Ser
        115                 120

<210> SEQ ID NO 17
<211> LENGTH: 121
<212> TYPE: PRT
<213> ORGANISM: ARTIFICIAL
<220> FEATURE:
<223> OTHER INFORMATION: MR

<400> SEQUENCE: 17

Glu Val Lys Leu Gln Glu Ser Gly Gly Gly Leu Val Gln Pro Gly Gly
1               5                   10                  15

Ser Met Arg Ile Ser Cys Ser Gly Ser Gly Phe Thr Phe Thr Asp Phe
            20                  25                  30

Tyr Met Asn Trp Val Arg Gln Pro Pro Gly Lys Gly Pro Glu Trp Ile
        35                  40                  45

```
Gly Phe Ile Arg Asp Lys Ala Lys Gly Tyr Thr Thr Glu Tyr Asn Pro
        50                  55                  60

Ser Val Lys Gly Arg Phe Thr Ile Ser Arg Asp Asn Thr Gln Asn Thr
 65                  70                  75                  80

Leu His Leu Gln Ala Asn Thr Leu Arg Ala Glu Asp Thr Ala Val Tyr
                 85                  90                  95

Tyr Cys Ala Arg Glu Gly His Thr Ala Ala Pro Phe Asp Tyr Trp Gly
                100                 105                 110

Gln Gly Thr Thr Val Thr Val Ser Ser
            115                 120
```

<210> SEQ ID NO 18
<211> LENGTH: 121
<212> TYPE: PRT
<213> ORGANISM: ARTIFICIAL
<220> FEATURE:
<223> OTHER INFORMATION: MR

<400> SEQUENCE: 18

```
Glu Val Gln Leu Leu Glu Ser Gly Gly Gly Leu Val Gln Pro Gly Gly
 1               5                  10                  15

Ser Leu Arg Leu Ser Cys Ala Gly Ser Gly Phe Thr Phe Thr Asp Phe
                 20                  25                  30

Tyr Met Asn Trp Val Arg Gln Pro Pro Gly Lys Ala Pro Glu Trp Leu
             35                  40                  45

Gly Phe Ile Arg Asp Lys Ala Lys Gly Tyr Thr Thr Glu Tyr Asn Pro
        50                  55                  60

Ser Val Lys Gly Arg Phe Thr Ile Ser Arg Asp Asn Ser Lys Asn Thr
 65                  70                  75                  80

Leu Tyr Leu Gln Met Asn Ser Leu Arg Ala Glu Asp Thr Ala Val Tyr
                 85                  90                  95

Tyr Cys Ala Arg Glu Gly His Thr Ala Ala Pro Phe Asp Tyr Trp Gly
                100                 105                 110

Gln Gly Thr Leu Val Thr Val Ser Ser
            115                 120
```

<210> SEQ ID NO 19
<211> LENGTH: 121
<212> TYPE: PRT
<213> ORGANISM: ARTIFICIAL
<220> FEATURE:
<223> OTHER INFORMATION: MR

<400> SEQUENCE: 19

```
Glu Val Gln Leu Leu Glu Ser Gly Gly Gly Leu Val Gln Pro Gly Gly
 1               5                  10                  15

Ser Leu Arg Leu Ser Cys Ser Gly Ser Gly Phe Thr Phe Thr Asp Phe
                 20                  25                  30

Tyr Met Asn Trp Ile Arg Gln Pro Pro Gly Lys Ala Pro Glu Trp Ile
             35                  40                  45

Gly Phe Ile Arg Asp Lys Ala Lys Gly Tyr Thr Thr Glu Tyr Asn Pro
        50                  55                  60

Ser Val Lys Gly Arg Phe Thr Ile Ser Arg Asp Asn Ser Lys Asn Thr
 65                  70                  75                  80

Leu Tyr Leu Gln Met Asn Ser Leu Arg Ala Glu Asp Thr Ala Val Tyr
                 85                  90                  95

Tyr Cys Ala Arg Glu Gly His Thr Ala Ala Pro Phe Asp Tyr Trp Gly
```

Gln Gly Thr Leu Val Thr Val Ser Ser
        115                 120

<210> SEQ ID NO 20
<211> LENGTH: 121
<212> TYPE: PRT
<213> ORGANISM: ARTIFICIAL
<220> FEATURE:
<223> OTHER INFORMATION: MR

<400> SEQUENCE: 20

Glu Val Gln Leu Leu Glu Ser Gly Gly Gly Leu Val Gln Pro Gly Gly
1               5                   10                  15

Ser Leu Arg Leu Ser Cys Ser Gly Ser Gly Phe Thr Phe Thr Asp Phe
            20                  25                  30

Tyr Met Asn Trp Val Arg Gln Ala Pro Gly Lys Gly Leu Glu Trp Val
        35                  40                  45

Gly Phe Ile Arg Asp Lys Ala Lys Gly Tyr Thr Thr Glu Tyr Asn Pro
    50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Glu Gly His Thr Ala Ala Pro Phe Asp Tyr Trp Gly
            100                 105                 110

Gln Gly Thr Leu Val Thr Val Ser Ser
        115                 120

<210> SEQ ID NO 21
<211> LENGTH: 121
<212> TYPE: PRT
<213> ORGANISM: ARTIFICIAL
<220> FEATURE:
<223> OTHER INFORMATION: MR

<400> SEQUENCE: 21

Glu Val Gln Leu Leu Glu Ser Gly Gly Gly Leu Val Gln Pro Gly Gly
1               5                   10                  15

Ser Leu Arg Leu Ser Cys Ser Gly Ser Gly Phe Thr Phe Thr Asp Phe
            20                  25                  30

Tyr Met Asn Trp Ile Arg Gln Pro Pro Gly Lys Ala Pro Glu Trp Leu
        35                  40                  45

Gly Phe Ile Arg Asp Lys Ala Lys Gly Tyr Thr Thr Glu Tyr Asn Pro
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Glu Gly His Thr Ala Ala Pro Phe Asp Tyr Trp Gly
            100                 105                 110

Gln Gly Thr Leu Val Thr Val Ser Ser
        115                 120

<210> SEQ ID NO 22
<211> LENGTH: 121
<212> TYPE: PRT
<213> ORGANISM: ARTIFICIAL
<220> FEATURE:

<223> OTHER INFORMATION: MR

<400> SEQUENCE: 22

Glu Val Gln Leu Leu Glu Ser Gly Gly Gly Leu Val Gln Pro Gly Gly
1               5                   10                  15

Ser Leu Arg Leu Ser Cys Ala Gly Ser Gly Phe Thr Phe Thr Asp Phe
            20                  25                  30

Tyr Met Asn Trp Ile Arg Gln Ala Pro Gly Lys Ala Pro Glu Trp Ile
        35                  40                  45

Gly Phe Ile Arg Asp Lys Ala Lys Gly Tyr Thr Thr Glu Tyr Asn Pro
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Glu Gly His Thr Ala Ala Pro Phe Asp Tyr Trp Gly
            100                 105                 110

Gln Gly Thr Leu Val Thr Val Ser Ser
        115                 120

<210> SEQ ID NO 23
<211> LENGTH: 121
<212> TYPE: PRT
<213> ORGANISM: ARTIFICIAL
<220> FEATURE:
<223> OTHER INFORMATION: MR

<400> SEQUENCE: 23

Glu Val Lys Leu Gln Glu Ser Gly Gly Gly Leu Val Gln Pro Gly Gly
1               5                   10                  15

Ser Met Arg Ile Ser Cys Ser Gly Ser Gly Phe Thr Phe Thr Asp Phe
            20                  25                  30

Tyr Met Asn Trp Ile Arg Gln Ala Pro Gly Lys Gly Pro Glu Trp Ile
        35                  40                  45

Gly Phe Ile Arg Asp Lys Ala Lys Gly Tyr Thr Thr Glu Tyr Asn Pro
    50                  55                  60

Ser Val Lys Gly Arg Phe Thr Ile Ser Arg Asp Asn Thr Gln Asn Thr
65                  70                  75                  80

Leu His Leu Gln Ala Asn Thr Leu Arg Ala Glu Asp Thr Ala Val Tyr
                85                  90                  95

Tyr Cys Ala Arg Glu Gly His Thr Ala Ala Pro Phe Asp Tyr Trp Gly
            100                 105                 110

Gln Gly Thr Thr Val Thr Val Ser Ser
        115                 120

<210> SEQ ID NO 24
<211> LENGTH: 121
<212> TYPE: PRT
<213> ORGANISM: ARTIFICIAL
<220> FEATURE:
<223> OTHER INFORMATION: MR

<400> SEQUENCE: 24

Glu Val Gln Leu Leu Glu Ser Gly Gly Gly Leu Val Gln Pro Gly Gly
1               5                   10                  15

Ser Leu Arg Leu Ser Cys Ala Gly Ser Gly Phe Thr Phe Thr Asp Phe
            20                  25                  30

Tyr Met Asn Trp Ile Arg Gln Ala Pro Gly Lys Ala Pro Glu Trp Leu

```
                   35                  40                  45
Gly Phe Ile Arg Asp Lys Ala Lys Gly Tyr Thr Thr Glu Tyr Asn Pro
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Glu Gly His Thr Ala Ala Pro Phe Asp Tyr Trp Gly
                100                 105                 110

Gln Gly Thr Leu Val Thr Val Ser Ser
            115                 120

<210> SEQ ID NO 25
<211> LENGTH: 121
<212> TYPE: PRT
<213> ORGANISM: ARTIFICIAL
<220> FEATURE:
<223> OTHER INFORMATION: MR

<400> SEQUENCE: 25

Glu Val Gln Leu Leu Glu Ser Gly Gly Gly Leu Val Gln Pro Gly Gly
1               5                   10                  15

Ser Leu Arg Leu Ser Cys Ala Gly Ser Gly Phe Thr Phe Thr Asp Phe
                20                  25                  30

Tyr Met Asn Trp Ile Arg Gln Pro Pro Gly Lys Ala Pro Glu Trp Ile
            35                  40                  45

Gly Phe Ile Arg Asp Lys Ala Lys Gly Tyr Thr Thr Glu Tyr Asn Pro
    50                  55                  60

Ser Val Lys Gly Arg Phe Thr Ile Ser Arg Asp Asn Ser Lys Asn Thr
65                  70                  75                  80

Leu Tyr Leu Gln Ala Asn Ser Leu Arg Ala Glu Asp Thr Ala Val Tyr
                85                  90                  95

Tyr Cys Ala Arg Glu Gly His Thr Ala Ala Pro Phe Asp Tyr Trp Gly
                100                 105                 110

Gln Gly Thr Leu Val Thr Val Ser Ser
            115                 120

<210> SEQ ID NO 26
<211> LENGTH: 121
<212> TYPE: PRT
<213> ORGANISM: ARTIFICIAL
<220> FEATURE:
<223> OTHER INFORMATION: MR

<400> SEQUENCE: 26

Glu Val Gln Leu Leu Glu Ser Gly Gly Gly Leu Val Gln Pro Gly Gly
1               5                   10                  15

Ser Leu Arg Leu Ser Cys Ala Gly Ser Gly Phe Thr Phe Thr Asp Phe
                20                  25                  30

Tyr Met Asn Trp Val Arg Gln Ala Pro Gly Lys Gly Leu Glu Trp Val
            35                  40                  45

Gly Phe Ile Arg Asp Lys Ala Lys Gly Tyr Thr Thr Glu Tyr Asn Pro
    50                  55                  60

Ser Val Lys Gly Arg Phe Thr Ile Ser Arg Asp Asn Ala Lys Asn Ser
65                  70                  75                  80

Leu Tyr Leu Gln Ala Asn Ser Leu Arg Ala Glu Asp Thr Ala Val Tyr
                85                  90                  95
```

```
Tyr Cys Ala Arg Glu Gly His Thr Ala Ala Pro Phe Asp Tyr Trp Gly
            100                 105                 110

Gln Gly Thr Leu Val Thr Val Ser Ser
        115                 120

<210> SEQ ID NO 27
<211> LENGTH: 121
<212> TYPE: PRT
<213> ORGANISM: ARTIFICIAL
<220> FEATURE:
<223> OTHER INFORMATION: MR

<400> SEQUENCE: 27

Glu Val Gln Leu Leu Glu Ser Gly Gly Gly Leu Val Gln Pro Gly Gly
1               5                   10                  15

Ser Leu Arg Leu Ser Cys Ala Gly Ser Gly Phe Thr Phe Thr Asp Phe
            20                  25                  30

Tyr Met Asn Trp Ile Arg Gln Pro Pro Gly Lys Ala Pro Glu Trp Leu
        35                  40                  45

Gly Phe Ile Arg Asp Lys Ala Lys Gly Tyr Thr Thr Glu Tyr Asn Pro
    50                  55                  60

Ser Val Lys Gly Arg Phe Thr Ile Ser Arg Asp Asn Ser Lys Asn Thr
65                  70                  75                  80

Leu Tyr Leu Gln Ala Asn Ser Leu Arg Ala Glu Asp Thr Ala Val Tyr
                85                  90                  95

Tyr Cys Ala Arg Glu Gly His Thr Ala Ala Pro Phe Asp Tyr Trp Gly
            100                 105                 110

Gln Gly Thr Leu Val Thr Val Ser Ser
        115                 120

<210> SEQ ID NO 28
<211> LENGTH: 121
<212> TYPE: PRT
<213> ORGANISM: ARTIFICIAL
<220> FEATURE:
<223> OTHER INFORMATION: MR

<400> SEQUENCE: 28

Glu Val Gln Leu Leu Glu Ser Gly Gly Gly Leu Val Gln Pro Gly Gly
1               5                   10                  15

Ser Leu Arg Leu Ser Cys Ala Gly Ser Gly Phe Thr Phe Thr Asp Phe
            20                  25                  30

Tyr Met Asn Trp Ile Arg Gln Pro Pro Gly Lys Ala Pro Glu Trp Ile
        35                  40                  45

Gly Phe Ile Arg Asp Lys Ala Lys Gly Tyr Thr Thr Glu Tyr Asn Pro
    50                  55                  60

Ser Val Lys Gly Arg Phe Thr Ile Ser Arg Asp Asn Ser Gln Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Glu Gly His Thr Ala Ala Pro Phe Asp Tyr Trp Gly
            100                 105                 110

Gln Gly Thr Leu Val Thr Val Ser Ser
        115                 120

<210> SEQ ID NO 29
<211> LENGTH: 121
<212> TYPE: PRT
<213> ORGANISM: ARTIFICIAL
```

-continued

```
<220> FEATURE:
<223> OTHER INFORMATION: MR

<400> SEQUENCE: 29

Glu Val Gln Leu Leu Glu Ser Gly Gly Gly Leu Val Gln Pro Gly Gly
1               5                   10                  15

Ser Leu Arg Leu Ser Cys Ala Gly Ser Gly Phe Thr Phe Thr Asp Phe
            20                  25                  30

Tyr Met Asn Trp Val Arg Gln Ala Pro Gly Lys Gly Leu Glu Trp Val
        35                  40                  45

Gly Phe Ile Arg Asp Lys Ala Lys Gly Tyr Thr Thr Glu Tyr Asn Pro
    50                  55                  60

Ser Val Lys Gly Arg Phe Thr Ile Ser Arg Asp Asn Ala Gln Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Glu Gly His Thr Ala Ala Pro Phe Asp Tyr Trp Gly
            100                 105                 110

Gln Gly Thr Leu Val Thr Val Ser Ser
        115                 120

<210> SEQ ID NO 30
<211> LENGTH: 121
<212> TYPE: PRT
<213> ORGANISM: ARTIFICIAL
<220> FEATURE:
<223> OTHER INFORMATION: MR

<400> SEQUENCE: 30

Glu Val Gln Leu Leu Glu Ser Gly Gly Gly Leu Val Gln Pro Gly Gly
1               5                   10                  15

Ser Leu Arg Leu Ser Cys Ala Gly Ser Gly Phe Thr Phe Thr Asp Phe
            20                  25                  30

Tyr Met Asn Trp Ile Arg Gln Pro Pro Gly Lys Ala Pro Glu Trp Leu
        35                  40                  45

Gly Phe Ile Arg Asp Lys Ala Lys Gly Tyr Thr Thr Glu Tyr Asn Pro
    50                  55                  60

Ser Val Lys Gly Arg Phe Thr Ile Ser Arg Asp Asn Ser Gln Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Glu Gly His Thr Ala Ala Pro Phe Asp Tyr Trp Gly
            100                 105                 110

Gln Gly Thr Leu Val Thr Val Ser Ser
        115                 120

<210> SEQ ID NO 31
<211> LENGTH: 121
<212> TYPE: PRT
<213> ORGANISM: ARTIFICIAL
<220> FEATURE:
<223> OTHER INFORMATION: MR

<400> SEQUENCE: 31

Glu Val Gln Leu Leu Glu Ser Gly Gly Gly Leu Val Gln Pro Gly Gly
1               5                   10                  15

Ser Leu Arg Leu Ser Cys Ala Gly Ser Gly Phe Thr Phe Thr Asp Phe
            20                  25                  30
```

-continued

```
Tyr Met Asn Trp Ile Arg Gln Pro Pro Gly Lys Ala Pro Glu Trp Ile
            35                  40                  45

Gly Phe Ile Arg Asp Lys Ala Lys Gly Tyr Thr Thr Glu Tyr Asn Pro
        50                  55                  60

Ser Val Lys Gly Arg Phe Thr Ile Ser Arg Asp Asn Thr Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Glu Gly His Thr Ala Ala Pro Phe Asp Tyr Trp Gly
            100                 105                 110

Gln Gly Thr Leu Val Thr Val Ser Ser
        115                 120
```

<210> SEQ ID NO 32
<211> LENGTH: 121
<212> TYPE: PRT
<213> ORGANISM: ARTIFICIAL
<220> FEATURE:
<223> OTHER INFORMATION: MR

<400> SEQUENCE: 32

```
Glu Val Gln Leu Leu Glu Ser Gly Gly Gly Leu Val Gln Pro Gly Gly
1               5                   10                  15

Ser Leu Arg Leu Ser Cys Ala Gly Ser Gly Phe Thr Phe Thr Asp Phe
            20                  25                  30

Tyr Met Asn Trp Val Arg Gln Ala Pro Gly Lys Gly Leu Glu Trp Val
            35                  40                  45

Gly Phe Ile Arg Asp Lys Ala Lys Gly Tyr Thr Thr Glu Tyr Asn Pro
        50                  55                  60

Ser Val Lys Gly Arg Phe Thr Ile Ser Arg Asp Asn Thr Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Glu Gly His Thr Ala Ala Pro Phe Asp Tyr Trp Gly
            100                 105                 110

Gln Gly Thr Leu Val Thr Val Ser Ser
        115                 120
```

<210> SEQ ID NO 33
<211> LENGTH: 121
<212> TYPE: PRT
<213> ORGANISM: ARTIFICIAL
<220> FEATURE:
<223> OTHER INFORMATION: MR

<400> SEQUENCE: 33

```
Glu Val Gln Leu Leu Glu Ser Gly Gly Gly Leu Val Gln Pro Gly Gly
1               5                   10                  15

Ser Leu Arg Leu Ser Cys Ala Gly Ser Gly Phe Thr Phe Thr Asp Phe
            20                  25                  30

Tyr Met Asn Trp Ile Arg Gln Pro Pro Gly Lys Ala Pro Glu Trp Leu
            35                  40                  45

Gly Phe Ile Arg Asp Lys Ala Lys Gly Tyr Thr Thr Glu Tyr Asn Pro
        50                  55                  60

Ser Val Lys Gly Arg Phe Thr Ile Ser Arg Asp Asn Thr Lys Asn Thr
65                  70                  75                  80

Leu Tyr Leu Gln Met Asn Ser Leu Arg Ala Glu Asp Thr Ala Val Tyr
                85                  90                  95
```

```
Tyr Cys Ala Arg Glu Gly His Thr Ala Ala Pro Phe Asp Tyr Trp Gly
            100                 105                 110

Gln Gly Thr Leu Val Thr Val Ser Ser
        115                 120

<210> SEQ ID NO 34
<211> LENGTH: 121
<212> TYPE: PRT
<213> ORGANISM: ARTIFICIAL
<220> FEATURE:
<223> OTHER INFORMATION: MR

<400> SEQUENCE: 34

Glu Val Gln Leu Leu Glu Ser Gly Gly Gly Leu Val Gln Pro Gly Gly
1               5                   10                  15

Ser Met Arg Leu Ser Cys Ala Gly Ser Gly Phe Thr Phe Thr Asp Phe
            20                  25                  30

Tyr Met Asn Trp Ile Arg Gln Pro Pro Gly Lys Ala Pro Glu Trp Leu
            35                  40                  45

Gly Phe Ile Arg Asp Lys Ala Lys Gly Tyr Thr Thr Glu Tyr Asn Pro
        50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Glu Gly His Thr Ala Ala Pro Phe Asp Tyr Trp Gly
            100                 105                 110

Gln Gly Thr Leu Val Thr Val Ser Ser
        115                 120

<210> SEQ ID NO 35
<211> LENGTH: 121
<212> TYPE: PRT
<213> ORGANISM: ARTIFICIAL
<220> FEATURE:
<223> OTHER INFORMATION: MR

<400> SEQUENCE: 35

Glu Val Lys Leu Gln Glu Ser Gly Gly Gly Leu Val Gln Pro Gly Gly
1               5                   10                  15

Ser Met Arg Ile Ser Cys Ser Gly Ser Gly Phe Thr Phe Thr Asp Phe
            20                  25                  30

Tyr Met Asn Trp Ile Arg Gln Pro Pro Gly Lys Gly Pro Glu Trp Leu
            35                  40                  45

Gly Phe Ile Arg Asp Lys Ala Lys Gly Tyr Thr Thr Glu Tyr Asn Pro
        50                  55                  60

Ser Val Lys Gly Arg Phe Thr Ile Ser Arg Asp Asn Thr Gln Asn Thr
65                  70                  75                  80

Leu His Leu Gln Ala Asn Thr Leu Arg Ala Glu Asp Thr Ala Val Tyr
                85                  90                  95

Tyr Cys Ala Arg Glu Gly His Thr Ala Ala Pro Phe Asp Tyr Trp Gly
            100                 105                 110

Gln Gly Thr Thr Val Thr Val Ser Ser
        115                 120

<210> SEQ ID NO 36
<211> LENGTH: 121
<212> TYPE: PRT
```

<213> ORGANISM: ARTIFICIAL
<220> FEATURE:
<223> OTHER INFORMATION: MR

<400> SEQUENCE: 36

Glu Val Gln Leu Leu Glu Ser Gly Gly Gly Leu Val Gln Pro Gly Gly
1               5                   10                  15

Ser Leu Arg Leu Ser Cys Ala Gly Ser Gly Phe Thr Phe Thr Asp Phe
            20                  25                  30

Tyr Met Asn Trp Val Arg Gln Ala Pro Gly Lys Gly Leu Glu Trp Leu
        35                  40                  45

Gly Phe Ile Arg Asp Lys Ala Lys Gly Tyr Thr Thr Glu Tyr Asn Pro
    50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Glu Gly His Thr Ala Ala Pro Phe Asp Tyr Trp Gly
            100                 105                 110

Gln Gly Thr Leu Val Thr Val Ser Ser
            115                 120

<210> SEQ ID NO 37
<211> LENGTH: 121
<212> TYPE: PRT
<213> ORGANISM: ARTIFICIAL
<220> FEATURE:
<223> OTHER INFORMATION: MR

<400> SEQUENCE: 37

Glu Val Gln Leu Leu Glu Ser Gly Gly Gly Leu Val Gln Pro Gly Gly
1               5                   10                  15

Ser Leu Arg Leu Ser Cys Ala Gly Ser Gly Phe Thr Phe Thr Asp Phe
            20                  25                  30

Tyr Met Asn Trp Ile Arg Gln Pro Pro Gly Lys Ala Pro Glu Trp Ile
        35                  40                  45

Gly Phe Ile Arg Asp Lys Ala Lys Gly Tyr Thr Thr Glu Tyr Asn Pro
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Glu Gly His Thr Ala Ala Pro Phe Asp Tyr Trp Gly
            100                 105                 110

Gln Gly Thr Thr Val Thr Val Ser Ser
            115                 120

<210> SEQ ID NO 38
<211> LENGTH: 121
<212> TYPE: PRT
<213> ORGANISM: ARTIFICIAL
<220> FEATURE:
<223> OTHER INFORMATION: MR

<400> SEQUENCE: 38

Glu Val Gln Leu Leu Glu Ser Gly Gly Gly Leu Val Gln Pro Gly Gly
1               5                   10                  15

Ser Leu Arg Leu Ser Cys Ala Gly Ser Gly Phe Thr Phe Thr Asp Phe
            20                  25                  30

-continued

Tyr Met Asn Trp Val Arg Gln Ala Pro Gly Lys Gly Leu Glu Trp Val
            35                  40                  45

Gly Phe Ile Arg Asp Lys Ala Lys Gly Tyr Thr Thr Glu Tyr Asn Pro
 50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Glu Gly His Thr Ala Ala Pro Phe Asp Tyr Trp Gly
                100                 105                 110

Gln Gly Thr Thr Val Thr Val Ser Ser
        115                 120

<210> SEQ ID NO 39
<211> LENGTH: 121
<212> TYPE: PRT
<213> ORGANISM: ARTIFICIAL
<220> FEATURE:
<223> OTHER INFORMATION: MR

<400> SEQUENCE: 39

Glu Val Gln Leu Leu Glu Ser Gly Gly Gly Leu Val Gln Pro Gly Gly
1               5                   10                  15

Ser Leu Arg Leu Ser Cys Ala Gly Ser Gly Phe Thr Phe Thr Asp Phe
            20                  25                  30

Tyr Met Asn Trp Ile Arg Gln Pro Pro Gly Lys Ala Pro Glu Trp Leu
            35                  40                  45

Gly Phe Ile Arg Asp Lys Ala Lys Gly Tyr Thr Thr Glu Tyr Asn Pro
 50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Glu Gly His Thr Ala Ala Pro Phe Asp Tyr Trp Gly
                100                 105                 110

Gln Gly Thr Thr Val Thr Val Ser Ser
        115                 120

<210> SEQ ID NO 40
<211> LENGTH: 121
<212> TYPE: PRT
<213> ORGANISM: ARTIFICIAL
<220> FEATURE:
<223> OTHER INFORMATION: MR

<400> SEQUENCE: 40

Glu Val Gln Leu Leu Glu Ser Gly Gly Gly Leu Val Gln Pro Gly Gly
1               5                   10                  15

Ser Leu Arg Leu Ser Cys Ala Gly Ser Gly Phe Thr Phe Thr Asp Phe
            20                  25                  30

Tyr Met Asn Trp Ile Arg Gln Pro Pro Gly Lys Ala Pro Glu Trp Leu
            35                  40                  45

Gly Phe Ile Arg Asp Lys Ala Lys Gly Tyr Thr Thr Glu Tyr Asn Pro
 50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Thr Tyr

-continued

```
                85                  90                  95
Tyr Cys Ala Arg Glu Gly His Thr Ala Ala Pro Phe Asp Tyr Trp Gly
            100                 105                 110

Gln Gly Thr Thr Val Thr Val Ser Ser
        115                 120

<210> SEQ ID NO 41
<211> LENGTH: 107
<212> TYPE: PRT
<213> ORGANISM: ARTIFICIAL
<220> FEATURE:
<223> OTHER INFORMATION: MR

<400> SEQUENCE: 41

Asp Ile Gln Met Thr Gln Ser Pro Ser Ala Leu Ser Ala Ser Val Gly
1               5                   10                  15

Asp Arg Val Thr Pro Thr Cys Arg Ala Ser Gln Asn Ile Asp Lys Tyr
            20                  25                  30

Leu Asn Trp Tyr Gln Gln Lys Pro Gly Lys Ala Pro Lys Ser Leu Ile
        35                  40                  45

Tyr Asn Thr Asn Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Leu Gln His Ile Ser Arg Pro Arg
                85                  90                  95

Thr Phe Gly Thr Gly Thr Lys Leu Glu Leu Lys
            100                 105

<210> SEQ ID NO 42
<211> LENGTH: 107
<212> TYPE: PRT
<213> ORGANISM: ARTIFICIAL
<220> FEATURE:
<223> OTHER INFORMATION: MR

<400> SEQUENCE: 42

Asp Ile Gln Met Thr Gln Ser Pro Ser Ala Leu Ser Ala Ser Val Gly
1               5                   10                  15

Asp Arg Val Thr Pro Thr Cys Lys Ala Ser Gln Asn Ile Asp Lys Tyr
            20                  25                  30

Leu Asn Trp Tyr Gln Gln Lys Pro Gly Lys Ala Pro Lys Leu Leu Ile
        35                  40                  45

Tyr Asn Thr Asn Asn Leu Gln Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Leu Gln His Ile Ser Arg Pro Arg
                85                  90                  95

Thr Phe Gly Thr Gly Thr Lys Leu Glu Leu Lys
            100                 105

<210> SEQ ID NO 43
<211> LENGTH: 107
<212> TYPE: PRT
<213> ORGANISM: ARTIFICIAL
<220> FEATURE:
<223> OTHER INFORMATION: MR

<400> SEQUENCE: 43
```

Asp Ile Gln Met Thr Gln Ser Pro Ser Ala Leu Ser Ala Ser Val Gly
1               5                   10                  15

Asp Arg Val Thr Pro Thr Cys Arg Ala Ser Gln Asn Ile Asp Lys Tyr
            20                  25                  30

Leu Asn Trp Tyr Gln Gln Lys Pro Gly Lys Ala Pro Lys Leu Leu Ile
            35                  40                  45

Tyr Asn Thr Asn Asn Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Leu Gln His Ile Ser Arg Pro Arg
                85                  90                  95

Thr Phe Gly Thr Gly Thr Lys Leu Glu Leu Lys
            100                 105

<210> SEQ ID NO 44
<211> LENGTH: 107
<212> TYPE: PRT
<213> ORGANISM: ARTIFICIAL
<220> FEATURE:
<223> OTHER INFORMATION: MR

<400> SEQUENCE: 44

Asp Ile Gln Met Thr Gln Ser Pro Ser Ala Leu Ser Ala Ser Val Gly
1               5                   10                  15

Asp Arg Val Thr Pro Thr Cys Lys Ala Ser Gln Asn Ile Asp Lys Tyr
            20                  25                  30

Leu Asn Trp Tyr Gln Gln Lys Pro Gly Lys Ala Pro Lys Ser Leu Ile
            35                  40                  45

Tyr Asn Thr Asn Asn Leu Gln Thr Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Leu Gln His Ile Ser Arg Pro Arg
                85                  90                  95

Thr Phe Gly Thr Gly Thr Lys Leu Glu Leu Lys
            100                 105

<210> SEQ ID NO 45
<211> LENGTH: 107
<212> TYPE: PRT
<213> ORGANISM: ARTIFICIAL
<220> FEATURE:
<223> OTHER INFORMATION: MR

<400> SEQUENCE: 45

Asp Ile Gln Met Thr Gln Ser Pro Ser Ala Leu Ser Ala Ser Val Gly
1               5                   10                  15

Asp Arg Val Thr Pro Thr Cys Lys Ala Ser Gln Asn Ile Asp Lys Tyr
            20                  25                  30

Leu Asn Trp Tyr Gln Gln Lys Pro Gly Lys Ser Pro Lys Leu Leu Ile
            35                  40                  45

Tyr Asn Thr Asn Asn Leu Gln Thr Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Leu Gln His Ile Ser Arg Pro Arg

```
                85                  90                  95
Thr Phe Gly Thr Gly Thr Lys Leu Glu Leu Lys
            100                 105

<210> SEQ ID NO 46
<211> LENGTH: 107
<212> TYPE: PRT
<213> ORGANISM: ARTIFICIAL
<220> FEATURE:
<223> OTHER INFORMATION: MR

<400> SEQUENCE: 46

Asp Ile Gln Met Thr Gln Ser Pro Ser Ala Leu Ser Ala Ser Val Gly
1               5                  10                  15

Asp Arg Val Thr Ile Thr Cys Arg Ala Ser Gln Asn Ile Asp Lys Tyr
            20                  25                  30

Leu Asn Trp Tyr Gln Gln Lys Pro Gly Lys Ala Pro Lys Ser Leu Ile
        35                  40                  45

Tyr Asn Thr Asn Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Leu Gln His Ile Ser Arg Pro Arg
                85                  90                  95

Thr Phe Gly Thr Gly Thr Lys Leu Glu Leu Lys
            100                 105

<210> SEQ ID NO 47
<211> LENGTH: 107
<212> TYPE: PRT
<213> ORGANISM: ARTIFICIAL
<220> FEATURE:
<223> OTHER INFORMATION: MR

<400> SEQUENCE: 47

Asp Ile Gln Met Thr Gln Ser Pro Ser Ala Leu Ser Ala Ser Val Gly
1               5                  10                  15

Asp Arg Val Thr Ile Thr Cys Lys Ala Ser Gln Asn Ile Asp Lys Tyr
            20                  25                  30

Leu Asn Trp Tyr Gln Gln Lys Pro Gly Lys Ala Pro Lys Leu Leu Ile
        35                  40                  45

Tyr Asn Thr Asn Asn Leu Gln Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Leu Gln His Ile Ser Arg Pro Arg
                85                  90                  95

Thr Phe Gly Thr Gly Thr Lys Leu Glu Leu Lys
            100                 105

<210> SEQ ID NO 48
<211> LENGTH: 107
<212> TYPE: PRT
<213> ORGANISM: ARTIFICIAL
<220> FEATURE:
<223> OTHER INFORMATION: MR

<400> SEQUENCE: 48

Asp Ile Gln Met Thr Gln Ser Pro Ser Ala Leu Ser Ala Ser Val Gly
1               5                  10                  15
```

```
Asp Arg Val Thr Ile Thr Cys Arg Ala Ser Gln Asn Ile Asp Lys Tyr
            20                  25                  30

Leu Asn Trp Tyr Gln Gln Lys Pro Gly Lys Ala Pro Lys Leu Leu Ile
        35                  40                  45

Tyr Asn Thr Asn Asn Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Leu Gln His Ile Ser Arg Pro Arg
                85                  90                  95

Thr Phe Gly Thr Gly Thr Lys Leu Glu Leu Lys
            100                 105

<210> SEQ ID NO 49
<211> LENGTH: 107
<212> TYPE: PRT
<213> ORGANISM: ARTIFICIAL
<220> FEATURE:
<223> OTHER INFORMATION: MR

<400> SEQUENCE: 49

Asp Ile Gln Met Thr Gln Ser Pro Ser Ala Leu Ser Ala Ser Val Gly
1               5                   10                  15

Asp Arg Val Thr Ile Thr Cys Lys Ala Ser Gln Asn Ile Asp Lys Tyr
            20                  25                  30

Leu Asn Trp Tyr Gln Gln Lys Pro Gly Lys Ala Pro Lys Ser Leu Ile
        35                  40                  45

Tyr Asn Thr Asn Asn Leu Gln Thr Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Leu Gln His Ile Ser Arg Pro Arg
                85                  90                  95

Thr Phe Gly Thr Gly Thr Lys Leu Glu Leu Lys
            100                 105

<210> SEQ ID NO 50
<211> LENGTH: 107
<212> TYPE: PRT
<213> ORGANISM: ARTIFICIAL
<220> FEATURE:
<223> OTHER INFORMATION: MR

<400> SEQUENCE: 50

Asp Ile Gln Met Thr Gln Ser Pro Ser Ala Leu Ser Ala Ser Val Gly
1               5                   10                  15

Asp Arg Val Thr Ile Thr Cys Lys Ala Ser Gln Asn Ile Asp Lys Tyr
            20                  25                  30

Leu Asn Trp Tyr Gln Gln Lys Pro Gly Lys Ser Pro Lys Leu Leu Ile
        35                  40                  45

Tyr Asn Thr Asn Asn Leu Gln Thr Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Leu Gln His Ile Ser Arg Pro Arg
                85                  90                  95

Thr Phe Gly Thr Gly Thr Lys Leu Glu Leu Lys
```

```
<210> SEQ ID NO 51
<211> LENGTH: 107
<212> TYPE: PRT
<213> ORGANISM: ARTIFICIAL
<220> FEATURE:
<223> OTHER INFORMATION: MR

<400> SEQUENCE: 51

Asp Ile Gln Met Thr Gln Ser Pro Ser Ser Leu Ser Ala Ser Val Gly
1               5                   10                  15

Asp Arg Val Thr Pro Thr Cys Arg Ala Ser Gln Asn Ile Asp Lys Tyr
            20                  25                  30

Leu Asn Trp Tyr Gln Gln Lys Pro Gly Lys Ala Pro Lys Ser Leu Ile
        35                  40                  45

Tyr Asn Thr Asn Asn Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Leu Gln His Ile Ser Arg Pro Arg
                85                  90                  95

Thr Phe Gly Thr Gly Thr Lys Leu Glu Leu Lys
            100                 105

<210> SEQ ID NO 52
<211> LENGTH: 107
<212> TYPE: PRT
<213> ORGANISM: ARTIFICIAL
<220> FEATURE:
<223> OTHER INFORMATION: MR

<400> SEQUENCE: 52

Asp Ile Gln Met Thr Gln Ser Pro Ser Ser Leu Ser Ala Ser Val Gly
1               5                   10                  15

Asp Arg Val Thr Pro Thr Cys Lys Ala Ser Gln Asn Ile Asp Lys Tyr
            20                  25                  30

Leu Asn Trp Tyr Gln Gln Lys Pro Gly Lys Ala Pro Lys Leu Leu Ile
        35                  40                  45

Tyr Asn Thr Asn Asn Leu Gln Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Leu Gln His Ile Ser Arg Pro Arg
                85                  90                  95

Thr Phe Gly Thr Gly Thr Lys Leu Glu Leu Lys
            100                 105

<210> SEQ ID NO 53
<211> LENGTH: 107
<212> TYPE: PRT
<213> ORGANISM: ARTIFICIAL
<220> FEATURE:
<223> OTHER INFORMATION: MR

<400> SEQUENCE: 53

Asp Ile Gln Met Thr Gln Ser Pro Ser Ser Leu Ser Ala Ser Val Gly
1               5                   10                  15

Asp Arg Val Thr Pro Thr Cys Arg Ala Ser Gln Asn Ile Asp Lys Tyr
            20                  25                  30
```

```
Leu Asn Trp Tyr Gln Gln Lys Pro Gly Lys Ala Pro Lys Leu Leu Ile
            35                  40                  45

Tyr Asn Thr Asn Asn Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Ile Ala Thr Tyr Tyr Cys Leu Gln His Ile Ser Arg Pro Arg
                 85                  90                  95

Thr Phe Gly Thr Gly Thr Lys Leu Glu Leu Lys
                100                 105

<210> SEQ ID NO 54
<211> LENGTH: 107
<212> TYPE: PRT
<213> ORGANISM: ARTIFICIAL
<220> FEATURE:
<223> OTHER INFORMATION: Mutated Recombinant

<400> SEQUENCE: 54

Asp Ile Gln Met Thr Gln Ser Pro Ser Ser Leu Ser Ala Ser Val Gly
 1               5                  10                  15

Asp Arg Val Thr Pro Thr Cys Lys Ala Ser Gln Asn Ile Asp Lys Tyr
                20                  25                  30

Leu Asn Trp Tyr Gln Gln Lys Pro Gly Lys Ala Pro Lys Ser Leu Ile
            35                  40                  45

Tyr Asn Thr Asn Asn Leu Gln Thr Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Ile Ala Thr Tyr Tyr Cys Leu Gln His Ile Ser Arg Pro Arg
                 85                  90                  95

Thr Phe Gly Thr Gly Thr Lys Leu Glu Leu Lys
                100                 105

<210> SEQ ID NO 55
<211> LENGTH: 107
<212> TYPE: PRT
<213> ORGANISM: ARTIFICIAL
<220> FEATURE:
<223> OTHER INFORMATION: MR

<400> SEQUENCE: 55

Asp Ile Gln Met Thr Gln Ser Pro Ser Ser Leu Ser Ala Ser Val Gly
 1               5                  10                  15

Asp Arg Val Thr Pro Thr Cys Lys Ala Ser Gln Asn Ile Asp Lys Tyr
                20                  25                  30

Leu Asn Trp Tyr Gln Gln Lys Pro Gly Lys Ser Pro Lys Leu Leu Ile
            35                  40                  45

Tyr Asn Thr Asn Asn Leu Gln Thr Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Ile Ala Thr Tyr Tyr Cys Leu Gln His Ile Ser Arg Pro Arg
                 85                  90                  95

Thr Phe Gly Thr Gly Thr Lys Leu Glu Leu Lys
                100                 105
```

```
<210> SEQ ID NO 56
<211> LENGTH: 107
<212> TYPE: PRT
<213> ORGANISM: ARTIFICIAL
<220> FEATURE:
<223> OTHER INFORMATION: MR

<400> SEQUENCE: 56
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Asp Lys Tyr
            20                  25                  30

Leu Asn Trp Tyr Gln Gln Lys Ser Gly Lys Ala Pro Lys Ser Leu Ile
        35                  40                  45

Tyr Asn Thr Asn Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Leu Gln His Ile Ser Arg Pro Arg
                85                  90                  95

Thr Phe Gly Thr Gly Thr Lys Leu Glu Leu Lys
            100                 105

```
<210> SEQ ID NO 57
<211> LENGTH: 107
<212> TYPE: PRT
<213> ORGANISM: SEQ ID 58

<400> SEQUENCE: 57
```

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Ile Asp Lys Tyr
            20                  25                  30

Leu Asn Trp Tyr Gln Gln Lys Ser Gly Lys Ala Pro Lys Leu Leu Ile
        35                  40                  45

Tyr Asn Thr Asn Asn Leu Gln Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Leu Gln His Ile Ser Arg Pro Arg
                85                  90                  95

Thr Phe Gly Thr Gly Thr Lys Leu Glu Leu Lys
            100                 105

```
<210> SEQ ID NO 58
<211> LENGTH: 107
<212> TYPE: PRT
<213> ORGANISM: ARTIFICIAL
<220> FEATURE:
<223> OTHER INFORMATION: MR

<400> SEQUENCE: 58
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Asp Lys Tyr
            20                  25                  30

Leu Asn Trp Tyr Gln Gln Lys Ser Gly Lys Ala Pro Lys Leu Leu Ile
        35                  40                  45

Tyr Asn Thr Asn Asn Leu Gln Ser Gly Val Pro Ser Arg Phe Ser Gly

```
              50                  55                  60
Ser Gly Ser Gly Thr Asp Phe Thr Leu Thr Ile Ser Ser Leu Gln Pro
 65                  70                  75                  80

Glu Asp Ile Ala Thr Tyr Tyr Cys Leu Gln His Ile Ser Arg Pro Arg
                 85                  90                  95

Thr Phe Gly Thr Gly Thr Lys Leu Glu Leu Lys
            100                 105

<210> SEQ ID NO 59
<211> LENGTH: 107
<212> TYPE: PRT
<213> ORGANISM: ARTIFICIAL
<220> FEATURE:
<223> OTHER INFORMATION: MR

<400> SEQUENCE: 59

Asp Ile Gln Met Thr Gln Ser Pro Ser Ser Leu Ser Ala Ser Val Gly
  1               5                  10                  15

Asp Arg Val Thr Ile Thr Cys Lys Ala Ser Gln Asn Ile Asp Lys Tyr
                 20                  25                  30

Leu Asn Trp Tyr Gln Gln Lys Ser Gly Lys Ala Pro Lys Ser Leu Ile
             35                  40                  45

Tyr Asn Thr Asn Asn Leu Gln Thr Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Ile Ala Thr Tyr Tyr Cys Leu Gln His Ile Ser Arg Pro Arg
                 85                  90                  95

Thr Phe Gly Thr Gly Thr Lys Leu Glu Leu Lys
            100                 105

<210> SEQ ID NO 60
<211> LENGTH: 107
<212> TYPE: PRT
<213> ORGANISM: ARTIFICIAL
<220> FEATURE:
<223> OTHER INFORMATION: MR

<400> SEQUENCE: 60

Asp Ile Gln Met Thr Gln Ser Pro Ser Ser Leu Ser Ala Ser Val Gly
  1               5                  10                  15

Asp Arg Val Thr Ile Thr Cys Lys Ala Ser Gln Asn Ile Asp Lys Tyr
                 20                  25                  30

Leu Asn Trp Tyr Gln Gln Lys Ser Gly Lys Ser Pro Lys Leu Leu Ile
             35                  40                  45

Tyr Asn Thr Asn Asn Leu Gln Thr Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Ile Ala Thr Tyr Tyr Cys Leu Gln His Ile Ser Arg Pro Arg
                 85                  90                  95

Thr Phe Gly Thr Gly Thr Lys Leu Glu Leu Lys
            100                 105

<210> SEQ ID NO 61
<211> LENGTH: 107
<212> TYPE: PRT
<213> ORGANISM: ARTIFICIAL
<220> FEATURE:
```

<223> OTHER INFORMATION: MR

<400> SEQUENCE: 61

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Asp Lys Tyr
            20                  25                  30

Leu Asn Trp Tyr Gln Gln Lys Pro Gly Lys Ala Pro Lys Ser Leu Ile
        35                  40                  45

Tyr Asn Thr Asn Asn Leu Gln Ser Gly Met Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Leu Gln His Ile Ser Arg Pro Arg
                85                  90                  95

Thr Phe Gly Thr Gly Thr Lys Leu Glu Leu Lys
            100                 105

<210> SEQ ID NO 62
<211> LENGTH: 107
<212> TYPE: PRT
<213> ORGANISM: ARTIFICIAL
<220> FEATURE:
<223> OTHER INFORMATION: MR

<400> SEQUENCE: 62

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Ile Asp Lys Tyr
            20                  25                  30

Leu Asn Trp Tyr Gln Gln Lys Pro Gly Lys Ala Pro Lys Leu Leu Ile
        35                  40                  45

Tyr Asn Thr Asn Asn Leu Gln Thr Gly Met Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Leu Gln His Ile Ser Arg Pro Arg
                85                  90                  95

Thr Phe Gly Thr Gly Thr Lys Leu Glu Leu Lys
            100                 105

<210> SEQ ID NO 63
<211> LENGTH: 107
<212> TYPE: PRT
<213> ORGANISM: ARTIFICIAL
<220> FEATURE:
<223> OTHER INFORMATION: MR

<400> SEQUENCE: 63

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Asp Lys Tyr
            20                  25                  30

Leu Asn Trp Tyr Gln Gln Lys Pro Gly Lys Ala Pro Lys Leu Leu Ile
        35                  40                  45

Tyr Asn Thr Asn Asn Leu Gln Ser Gly Met Pro Ser Arg Phe Ser Gly
    50                  55                  60

Ser Gly Ser Gly Thr Asp Phe Thr Leu Thr Ile Ser Ser Leu Gln Pro

```
65                  70                  75                  80
Glu Asp Ile Ala Thr Tyr Tyr Cys Leu Gln His Ile Ser Arg Pro Arg
                85                  90                  95
Thr Phe Gly Thr Gly Thr Lys Leu Glu Leu Lys
            100                 105

<210> SEQ ID NO 64
<211> LENGTH: 107
<212> TYPE: PRT
<213> ORGANISM: ARTIFICIAL
<220> FEATURE:
<223> OTHER INFORMATION: MR

<400> SEQUENCE: 64

Asp Ile Gln Met Thr Gln Ser Pro Ser Ser Leu Ser Ala Ser Val Gly
1               5                   10                  15
Asp Arg Val Thr Ile Thr Cys Lys Ala Ser Gln Asn Ile Asp Lys Tyr
                20                  25                  30
Leu Asn Trp Tyr Gln Gln Lys Pro Gly Lys Ala Pro Lys Ser Leu Ile
            35                  40                  45
Tyr Asn Thr Asn Asn Leu Gln Thr Gly Met Pro Ser Arg Phe Ser Gly
        50                  55                  60
Ser Gly Ser Gly Thr Asp Phe Thr Leu Thr Ile Ser Ser Leu Gln Pro
65                  70                  75                  80
Glu Asp Ile Ala Thr Tyr Tyr Cys Leu Gln His Ile Ser Arg Pro Arg
                85                  90                  95
Thr Phe Gly Thr Gly Thr Lys Leu Glu Leu Lys
            100                 105

<210> SEQ ID NO 65
<211> LENGTH: 107
<212> TYPE: PRT
<213> ORGANISM: ARTIFICIAL
<220> FEATURE:
<223> OTHER INFORMATION: MR

<400> SEQUENCE: 65

Asp Ile Gln Met Thr Gln Ser Pro Ser Ser Leu Ser Ala Ser Val Gly
1               5                   10                  15
Asp Arg Val Thr Ile Thr Cys Lys Ala Ser Gln Asn Ile Asp Lys Tyr
                20                  25                  30
Leu Asn Trp Tyr Gln Gln Lys Pro Gly Lys Ser Pro Lys Leu Leu Ile
            35                  40                  45
Tyr Asn Thr Asn Asn Leu Gln Thr Gly Met Pro Ser Arg Phe Ser Gly
        50                  55                  60
Ser Gly Ser Gly Thr Asp Phe Thr Leu Thr Ile Ser Ser Leu Gln Pro
65                  70                  75                  80
Glu Asp Ile Ala Thr Tyr Tyr Cys Leu Gln His Ile Ser Arg Pro Arg
                85                  90                  95
Thr Phe Gly Thr Gly Thr Lys Leu Glu Leu Lys
            100                 105

<210> SEQ ID NO 66
<211> LENGTH: 107
<212> TYPE: PRT
<213> ORGANISM: ARTIFICIAL
<220> FEATURE:
<223> OTHER INFORMATION: MR

<400> SEQUENCE: 66
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Asp Lys Tyr
            20                  25                  30

Leu Asn Trp Tyr Gln Gln Lys Ser Gly Lys Ala Pro Lys Ser Leu Ile
        35                  40                  45

Tyr Asn Thr Asn Asn Leu Gln Ser Gly Met Pro Ser Arg Phe Ser Gly
    50                  55                  60

Ser Gly Ser Gly Thr Asp Phe Thr Leu Thr Ile Ser Ser Leu Gln Pro
65              70                  75                  80

Glu Asp Ile Ala Thr Tyr Tyr Cys Leu Gln His Ile Ser Arg Pro Arg
                85                  90                  95

Thr Phe Gly Thr Gly Thr Lys Leu Glu Leu Lys
                100                 105

<210> SEQ ID NO 67
<211> LENGTH: 107
<212> TYPE: PRT
<213> ORGANISM: ARTIFICIAL
<220> FEATURE:
<223> OTHER INFORMATION: MR

<400> SEQUENCE: 67

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Ile Asp Lys Tyr
            20                  25                  30

Leu Asn Trp Tyr Gln Gln Lys Ser Gly Lys Ala Pro Lys Leu Leu Ile
        35                  40                  45

Tyr Asn Thr Asn Asn Leu Gln Thr Gly Met Pro Ser Arg Phe Ser Gly
    50                  55                  60

Ser Gly Ser Gly Thr Asp Phe Thr Leu Thr Ile Ser Ser Leu Gln Pro
65              70                  75                  80

Glu Asp Ile Ala Thr Tyr Tyr Cys Leu Gln His Ile Ser Arg Pro Arg
                85                  90                  95

Thr Phe Gly Thr Gly Thr Lys Leu Glu Leu Lys
                100                 105

<210> SEQ ID NO 68
<211> LENGTH: 107
<212> TYPE: PRT
<213> ORGANISM: ARTIFICIAL
<220> FEATURE:
<223> OTHER INFORMATION: MR

<400> SEQUENCE: 68

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Asp Lys Tyr
            20                  25                  30

Leu Asn Trp Tyr Gln Gln Lys Ser Gly Lys Ala Pro Lys Leu Leu Ile
        35                  40                  45

Tyr Asn Thr Asn Asn Leu Gln Ser Gly Met Pro Ser Arg Phe Ser Gly
    50                  55                  60

Ser Gly Ser Gly Thr Asp Phe Thr Leu Thr Ile Ser Ser Leu Gln Pro
65              70                  75                  80

Glu Asp Ile Ala Thr Tyr Tyr Cys Leu Gln His Ile Ser Arg Pro Arg
```

```
                     85                  90                  95

Thr Phe Gly Thr Gly Thr Lys Leu Glu Leu Lys
            100                 105

<210> SEQ ID NO 69
<211> LENGTH: 107
<212> TYPE: PRT
<213> ORGANISM: ARTIFICIAL
<220> FEATURE:
<223> OTHER INFORMATION: MR

<400> SEQUENCE: 69

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Ile Asp Lys Tyr
            20                  25                  30

Leu Asn Trp Tyr Gln Gln Lys Ser Gly Lys Ala Pro Lys Ser Leu Ile
        35                  40                  45

Tyr Asn Thr Asn Asn Leu Gln Thr Gly Met Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Leu Gln His Ile Ser Arg Pro Arg
                85                  90                  95

Thr Phe Gly Thr Gly Thr Lys Leu Glu Leu Lys
            100                 105

<210> SEQ ID NO 70
<211> LENGTH: 107
<212> TYPE: PRT
<213> ORGANISM: ARTIFICIAL
<220> FEATURE:
<223> OTHER INFORMATION: MR

<400> SEQUENCE: 70

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Ile Asp Lys Tyr
            20                  25                  30

Leu Asn Trp Tyr Gln Gln Lys Ser Gly Lys Ser Pro Lys Leu Leu Ile
        35                  40                  45

Tyr Asn Thr Asn Asn Leu Gln Thr Gly Met Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Leu Gln His Ile Ser Arg Pro Arg
                85                  90                  95

Thr Phe Gly Thr Gly Thr Lys Leu Glu Leu Lys
            100                 105

<210> SEQ ID NO 71
<211> LENGTH: 363
<212> TYPE: DNA
<213> ORGANISM: ARTIFICIAL
<220> FEATURE:
<223> OTHER INFORMATION: MR

<400> SEQUENCE: 71
gaggtgcaac tgttggaatc tggaggaggc ttggtacagc cggggggttc tctgagactc      60
```

```
tcctgtgcag gttctggatt caccttcact gatttctaca tgaactgggt ccgccaggct      120
ccagggaagg gacttgagtg ggtgggtttt attagagaca aagctaaagg ttacacaaca      180
gagtacaatc catctgtgaa ggggcggttc accatctcca gagataattc caaaaacacc      240
ctctatcttc aaatgaactc cctaagagct gaggacactg ccgtttacta ctgtgcaaga      300
gagggccaca ctgctgctcc ttttgattac tggggccaag gaacactggt caccgtctcc      360
tca                                                                    363

<210> SEQ ID NO 72
<211> LENGTH: 363
<212> TYPE: DNA
<213> ORGANISM: ARTIFICIAL
<220> FEATURE:
<223> OTHER INFORMATION: MR

<400> SEQUENCE: 72
gaggtgcaac tgttggaatc tggaggaggc ttggtacagc cggggggttc tctgagactc       60
tcctgtgcag gttctggatt caccttcact gatttctaca tgaactggat tcgccagcct      120
cccgggaaag cacctgagtg gattggtttt attagagaca aagctaaagg ttacacaaca      180
gagtacaatc catctgtgaa ggggcggttc accatctcca gagataattc caaaaacacc      240
ctctatcttc aaatgaactc cctaagagct gaggacactg ccgtttacta ctgtgcaaga      300
gagggccaca ctgctgctcc ttttgattac tggggccaag gaacactggt caccgtctcc      360
tca                                                                    363

<210> SEQ ID NO 73
<211> LENGTH: 363
<212> TYPE: DNA
<213> ORGANISM: ARTIFICIAL
<220> FEATURE:
<223> OTHER INFORMATION: MR

<400> SEQUENCE: 73
gaggtgaaac tgcaggaatc tggaggaggc ttggtacagc cggggggttc tatgagaatc       60
tcctgttcag gttctggatt caccttcact gatttctaca tgaactggat tcgccagcct      120
cccgggaaag gacctgagtg gattggtttt attagagaca aagctaaagg ttacacaaca      180
gagtacaatc catctgtgaa ggggcggttc accatctcca gagataatac ccaaaacacc      240
ctccatcttc aagctaacac cctaagagct gaggacactg ccgtttacta ctgtgcaaga      300
gagggccaca ctgctgctcc ttttgattac tggggccaag gaactaccgt caccgtctcc      360
tca                                                                    363

<210> SEQ ID NO 74
<211> LENGTH: 363
<212> TYPE: DNA
<213> ORGANISM: ARTIFICIAL
<220> FEATURE:
<223> OTHER INFORMATION: MR

<400> SEQUENCE: 74
gaggtgcaac tgttggaatc tggaggaggc ttggtacagc cggggggttc tctgagactc       60
tcctgtgcag gttctggatt caccttcact gatttctaca tgaactgggt ccgccaggct      120
ccagggaagg gacttgagtg ggtgggtttt attagagaca aagctaaagg ttacacaaca      180
gagtacaatc catctgtgaa ggggcggttc accatctcca gagataatgc caaaaactcc      240
ctctatcttc aaatgaactc cctaagagct gaggacactg ccgtttacta ctgtgcaaga      300
```

```
gagggccaca ctgctgctcc ttttgattac tggggccaag gaacactggt caccgtctcc    360
tca                                                                  363

<210> SEQ ID NO 75
<211> LENGTH: 363
<212> TYPE: DNA
<213> ORGANISM: ARTIFICIAL
<220> FEATURE:
<223> OTHER INFORMATION: MR

<400> SEQUENCE: 75
gaggtgcaac tgttggaatc tggaggaggc ttggtacagc cggggggttc tctgagactc    60
tcctgtgcag gttctggatt caccttcact gatttctaca tgaactggat tcgccagcct    120
cccgggaaag cacctgagtg gctgggtttt attagagaca aagctaaagg ttacacaaca    180
gagtacaatc catctgtgaa ggggcggttc accatctcca gagataattc caaaaacacc    240
ctctatcttc aaatgaactc cctaagagct gaggacactg ccgtttacta ctgtgcaaga    300
gagggccaca ctgctgctcc ttttgattac tggggccaag gaacactggt caccgtctcc    360
tca                                                                  363

<210> SEQ ID NO 76
<211> LENGTH: 321
<212> TYPE: DNA
<213> ORGANISM: ARTIFICIAL
<220> FEATURE:
<223> OTHER INFORMATION: MR

<400> SEQUENCE: 76
gacatccaga tgacccagtc tccctcatcc ctgtctgcat ctgtgggaga cagagtcact    60
atcacctgca gagcaagtca gaatattgac aaatacttaa actggtatca gcaaaagccc    120
ggaaaagctc ccaaatccct gatatataat acaaacaatt tgcaatctgg cgtcccatca    180
aggttcagtg gcagtggatc tggtactgat ttcacactca ccatcagcag cctgcagcct    240
gaagatattg ccacatatta ctgcttgcag catataagta ggccgcgcac gtttggaact    300
gggaccaagc tggagctgaa a                                              321

<210> SEQ ID NO 77
<211> LENGTH: 321
<212> TYPE: DNA
<213> ORGANISM: ARTIFICIAL
<220> FEATURE:
<223> OTHER INFORMATION: MR

<400> SEQUENCE: 77
gacatccaga tgacccagtc tccctcatcc ctgtctgcat ctgtgggaga cagagtcact    60
atcacctgca aagcaagtca gaatattgac aaatacttaa actggtatca gcaaaagccc    120
ggaaaagctc ccaaactcct gatatataat acaaacaatt tgcaaacggg cgtcccatca    180
aggttcagtg gcagtggatc tggtactgat ttcacactca ccatcagcag cctgcagcct    240
gaagatattg ccacatatta ctgcttgcag catataagta ggccgcgcac gtttggaact    300
gggaccaagc tggagctgaa a                                              321

<210> SEQ ID NO 78
<211> LENGTH: 321
<212> TYPE: DNA
<213> ORGANISM: ARTIFICIAL
<220> FEATURE:
```

<223> OTHER INFORMATION: MR

<400> SEQUENCE: 78

```
gacatccaga tgacccagtc tccctcatcc ctgtctgcat ctgtgggaga cagagtcact      60
atcacctgca gagcaagtca gaatattgac aaatacttaa actggtatca gcaaaagccc     120
ggaaaagctc ccaaactcct gatatataat acaaacaatt tgcaatctgg cgtcccatca     180
aggttcagtg gcagtggatc tggtactgat ttcacactca ccatcagcag cctgcagcct     240
gaagatattg ccacatatta ctgcttgcag catataagta ggccgcgcac gtttggaact     300
gggaccaagc tggagctgaa a                                               321
```

<210> SEQ ID NO 79
<211> LENGTH: 321
<212> TYPE: DNA
<213> ORGANISM: ARTIFICIAL
<220> FEATURE:
<223> OTHER INFORMATION: MR

<400> SEQUENCE: 79

```
gacatccaga tgacccagtc tccctcatcc ctgtctgcat ctgtgggaga cagagtcact      60
atcacctgca aagcaagtca gaatattgac aaatacttaa actggtatca gcaaaagccc     120
ggaaaagctc ccaaatccct gatatataat acaaacaatt tgcaaacggg cgtcccatca     180
aggttcagtg gcagtggatc tggtactgat ttcacactca ccatcagcag cctgcagcct     240
gaagatattg ccacatatta ctgcttgcag catataagta ggccgcgcac gtttggaact     300
gggaccaagc tggagctgaa a                                               321
```

<210> SEQ ID NO 80
<211> LENGTH: 321
<212> TYPE: DNA
<213> ORGANISM: ARTIFICIAL
<220> FEATURE:
<223> OTHER INFORMATION: MR

<400> SEQUENCE: 80

```
gacatccaga tgacccagtc tccctcatcc ctgtctgcat ctgtgggaga cagagtcact      60
atcacctgca aagcaagtca gaatattgac aaatacttaa actggtatca gcaaaagccc     120
ggaaaatctc ccaaactcct gatatataat acaaacaatt tgcaaacggg cgtcccatca     180
aggttcagtg gcagtggatc tggtactgat ttcacactca ccatcagcag cctgcagcct     240
gaagatattg ccacatatta ctgcttgcag catataagta ggccgcgcac gtttggaact     300
gggaccaagc tggagctgaa a                                               321
```

<210> SEQ ID NO 81
<211> LENGTH: 363
<212> TYPE: DNA
<213> ORGANISM: ARTIFICIAL
<220> FEATURE:
<223> OTHER INFORMATION: MR

<400> SEQUENCE: 81

```
gaggtgcaac tgcaggaatc tggaggaggc ttggtacagc cggggggttc tctgagactc      60
tcctgtgcag gttctggatt caccttcact gatttctaca tgaactggat cgccagcct     120
cccgggaaag cacctgagtg gattggtttt attagagaca agctaaagg ttacacaaca     180
gagtacaatc catctgtgaa ggggcggttc accatctcca gataattc caaaacacc       240
ctctatcttc aaatgaactc cctaagagct gaggacactg ccgtttacta ctgtgcaaga     300
```
gagggccaca ctgctgctcc ttttgattac tggggccaag aacactggt caccgtctcc    360 tca                                                                 363

<210> SEQ ID NO 82
<211> LENGTH: 363
<212> TYPE: DNA
<213> ORGANISM: ARTIFICIAL
<220> FEATURE:
<223> OTHER INFORMATION: MR

<400> SEQUENCE: 82
gaggtgcaac tgcaggaatc tggaggaggc ttggtacagc cggggggttc tctgagactc     60
tcctgtgcag gttctggatt caccttcact gatttctaca tgaactgggt ccgccaggct    120
ccagggaagg gacttgagtg ggtgggtttt attagagaca aagctaaagg ttacacaaca    180
gagtacaatc catctgtgaa ggggcggttc accatctcca gagataatgc caaaaactcc    240
ctctatcttc aaatgaactc cctaagagct gaggacactg ccgtttacta ctgtgcaaga    300
gagggccaca ctgctgctcc ttttgattac tggggccaag aacactggt caccgtctcc    360 tca                                                                 363

<210> SEQ ID NO 83
<211> LENGTH: 363
<212> TYPE: DNA
<213> ORGANISM: ARTIFICIAL
<220> FEATURE:
<223> OTHER INFORMATION: MR

<400> SEQUENCE: 83
gaggtgcaac tgcaggaatc tggaggaggc ttggtacagc cggggggttc tctgagactc     60
tcctgtgcag gttctggatt caccttcact gatttctaca tgaactggat tcgccagcct    120
cccgggaaag cacctgagtg gctgggtttt attagagaca aagctaaagg ttacacaaca    180
gagtacaatc catctgtgaa ggggcggttc accatctcca gagataattc caaaaacacc    240
ctctatcttc aaatgaactc cctaagagct gaggacactg ccgtttacta ctgtgcaaga    300
gagggccaca ctgctgctcc ttttgattac tggggccaag aacactggt caccgtctcc    360 tca                                                                 363

<210> SEQ ID NO 84
<211> LENGTH: 363
<212> TYPE: DNA
<213> ORGANISM: ARTIFICIAL
<220> FEATURE:
<223> OTHER INFORMATION: MR

<400> SEQUENCE: 84
gaggtgcaac tgttggaatc tggaggaggc ttggtacagc cggggggttc tctgagactc     60
tcctgtgcag gttctggatt caccttcact gatttctaca tgaactgggt ccgccagcct    120
cccgggaaag cacctgagtg gattggtttt attagagaca aagctaaagg ttacacaaca    180
gagtacaatc catctgtgaa ggggcggttc accatctcca gagataattc caaaaacacc    240
ctctatcttc aaatgaactc cctaagagct gaggacactg ccgtttacta ctgtgcaaga    300
gagggccaca ctgctgctcc ttttgattac tggggccaag aacactggt caccgtctcc    360 tca                                                                 363

<210> SEQ ID NO 85

```
<211> LENGTH: 363
<212> TYPE: DNA
<213> ORGANISM: ARTIFICIAL
<220> FEATURE:
<223> OTHER INFORMATION: MR

<400> SEQUENCE: 85
gaggtgaaac tgcaggaatc tggaggaggc ttggtacagc cggggggttc tatgagaatc      60
tcctgttcag gttctggatt caccttcact gatttctaca tgaactgggt ccgccagcct     120
cccgggaaag gacctgagtg gattggtttt attagagaca agctaaagg ttacacaaca      180
gagtacaatc catctgtgaa ggggcggttc accatctcca gagataatac ccaaaacacc     240
ctccatcttc aagctaacac cctaagagct gaggacactg ccgtttacta ctgtgcaaga     300
gagggccaca ctgctgctcc ttttgattac tggggccaag gaactaccgt caccgtctcc     360
tca                                                                   363

<210> SEQ ID NO 86
<211> LENGTH: 363
<212> TYPE: DNA
<213> ORGANISM: ARTIFICIAL
<220> FEATURE:
<223> OTHER INFORMATION: MR

<400> SEQUENCE: 86
gaggtgcaac tgttggaatc tggaggaggc ttggtacagc cggggggttc tctgagactc      60
tcctgtgcag gttctggatt caccttcact gatttctaca tgaactgggt ccgccagcct     120
cccgggaaag cacctgagtg gctgggtttt attagagaca agctaaagg ttacacaaca      180
gagtacaatc catctgtgaa ggggcggttc accatctcca gagataattc caaaacacc      240
ctctatcttc aaatgaactc cctaagagct gaggacactg ccgtttacta ctgtgcaaga     300
gagggccaca ctgctgctcc ttttgattac tggggccaag gaacactggt caccgtctcc     360
tca                                                                   363

<210> SEQ ID NO 87
<211> LENGTH: 363
<212> TYPE: DNA
<213> ORGANISM: ARTIFICIAL
<220> FEATURE:
<223> OTHER INFORMATION: MR

<400> SEQUENCE: 87
gaggtgcaac tgttggaatc tggaggaggc ttggtacagc cggggggttc tctgagactc      60
tcctgttcag gttctggatt caccttcact gatttctaca tgaactggat tcgccagcct     120
cccgggaaag cacctgagtg gattggtttt attagagaca agctaaagg ttacacaaca      180
gagtacaatc catctgtgaa ggggcggttc accatctcca gagataattc caaaacacc      240
ctctatcttc aaatgaactc cctaagagct gaggacactg ccgtttacta ctgtgcaaga     300
gagggccaca ctgctgctcc ttttgattac tggggccaag gaacactggt caccgtctcc     360
tca                                                                   363

<210> SEQ ID NO 88
<211> LENGTH: 363
<212> TYPE: DNA
<213> ORGANISM: ARTIFICIAL
<220> FEATURE:
<223> OTHER INFORMATION: MR

<400> SEQUENCE: 88
```

```
gaggtgcaac tgttggaatc tggaggaggc ttggtacagc cggggggttc tctgagactc    60
tcctgttcag gttctggatt caccttcact gatttctaca tgaactgggt ccgccaggct   120
ccagggaagg gacttgagtg ggtgggtttt attagagaca aagctaaagg ttacacaaca   180
gagtacaatc catctgtgaa ggggcggttc accatctcca gagataatgc caaaaactcc   240
ctctatcttc aaatgaactc cctaagagct gaggacactg ccgtttacta ctgtgcaaga   300
gagggccaca ctgctgctcc ttttgattac tggggccaag gaacactggt caccgtctcc   360
tca                                                                 363
```

<210> SEQ ID NO 89
<211> LENGTH: 363
<212> TYPE: DNA
<213> ORGANISM: ARTIFICIAL
<220> FEATURE:
<223> OTHER INFORMATION: MR

<400> SEQUENCE: 89

```
gaggtgcaac tgttggaatc tggaggaggc ttggtacagc cggggggttc tctgagactc    60
tcctgttcag gttctggatt caccttcact gatttctaca tgaactggat tcgccagcct   120
cccgggaaag cacctgagtg gctggttttt attagagaca aagctaaagg ttacacaaca   180
gagtacaatc catctgtgaa ggggcggttc accatctcca gagataattc caaaaacacc   240
ctctatcttc aaatgaactc cctaagagct gaggacactg ccgtttacta ctgtgcaaga   300
gagggccaca ctgctgctcc ttttgattac tggggccaag gaacactggt caccgtctcc   360
tca                                                                 363
```

<210> SEQ ID NO 90
<211> LENGTH: 363
<212> TYPE: DNA
<213> ORGANISM: ARTIFICIAL
<220> FEATURE:
<223> OTHER INFORMATION: MR

<400> SEQUENCE: 90

```
gaggtgcaac tgttggaatc tggaggaggc ttggtacagc cggggggttc tctgagactc    60
tcctgtgcag gttctggatt caccttcact gatttctaca tgaactggat tcgccaggct   120
cccgggaaag cacctgagtg gattggtttt attagagaca aagctaaagg ttacacaaca   180
gagtacaatc catctgtgaa ggggcggttc accatctcca gagataattc caaaaacacc   240
ctctatcttc aaatgaactc cctaagagct gaggacactg ccgtttacta ctgtgcaaga   300
gagggccaca ctgctgctcc ttttgattac tggggccaag gaacactggt caccgtctcc   360
tca                                                                 363
```

<210> SEQ ID NO 91
<211> LENGTH: 363
<212> TYPE: DNA
<213> ORGANISM: ARTIFICIAL
<220> FEATURE:
<223> OTHER INFORMATION: MR

<400> SEQUENCE: 91

```
gaggtgaaac tgcaggaatc tggaggaggc ttggtacagc cggggggttc tatgagaatc    60
tcctgttcag gttctggatt caccttcact gatttctaca tgaactggat tcgccaggct   120
cccgggaaag gacctgagtg gattggtttt attagagaca aagctaaagg ttacacaaca   180
```

| | |
|---|---|
| gagtacaatc catctgtgaa ggggcggttc accatctcca gagataatac ccaaaacacc | 240 |
| ctccatcttc aagctaacac cctaagagct gaggacactg ccgtttacta ctgtgcaaga | 300 |
| gagggccaca ctgctgctcc ttttgattac tggggccaag gaactaccgt caccgtctcc | 360 |
| tca | 363 |

<210> SEQ ID NO 92
<211> LENGTH: 363
<212> TYPE: DNA
<213> ORGANISM: ARTIFICIAL
<220> FEATURE:
<223> OTHER INFORMATION: MR

<400> SEQUENCE: 92

| | |
|---|---|
| gaggtgcaac tgttggaatc tggaggaggc ttggtacagc cggggggttc tctgagactc | 60 |
| tcctgtgcag gttctggatt caccttcact gatttctaca tgaactggat tcgccaggct | 120 |
| cccgggaaag cacctgagtg gctgggtttt attagagaca aagctaaagg ttacacaaca | 180 |
| gagtacaatc catctgtgaa ggggcggttc accatctcca gagataattc caaaaacacc | 240 |
| ctctatcttc aaatgaactc cctaagagct gaggacactg ccgtttacta ctgtgcaaga | 300 |
| gagggccaca ctgctgctcc ttttgattac tggggccaag gaacactggt caccgtctcc | 360 |
| tca | 363 |

<210> SEQ ID NO 93
<211> LENGTH: 363
<212> TYPE: DNA
<213> ORGANISM: ARTIFICIAL
<220> FEATURE:
<223> OTHER INFORMATION: MR

<400> SEQUENCE: 93

| | |
|---|---|
| gaggtgcaac tgttggaatc tggaggaggc ttggtacagc cggggggttc tctgagactc | 60 |
| tcctgtgcag gttctggatt caccttcact gatttctaca tgaactggat tcgccagcct | 120 |
| cccgggaaag cacctgagtg gattggtttt attagagaca aagctaaagg ttacacaaca | 180 |
| gagtacaatc catctgtgaa ggggcggttc accatctcca gagataattc caaaaacacc | 240 |
| ctctatcttc aagctaactc cctaagagct gaggacactg ccgtttacta ctgtgcaaga | 300 |
| gagggccaca ctgctgctcc ttttgattac tggggccaag gaacactggt caccgtctcc | 360 |
| tca | 363 |

<210> SEQ ID NO 94
<211> LENGTH: 363
<212> TYPE: DNA
<213> ORGANISM: ARTIFICIAL
<220> FEATURE:
<223> OTHER INFORMATION: MR

<400> SEQUENCE: 94

| | |
|---|---|
| gaggtgcaac tgttggaatc tggaggaggc ttggtacagc cggggggttc tctgagactc | 60 |
| tcctgtgcag gttctggatt caccttcact gatttctaca tgaactgggt ccgccaggct | 120 |
| ccagggaagg gacttgagtg ggtgggtttt attagagaca aagctaaagg ttacacaaca | 180 |
| gagtacaatc catctgtgaa ggggcggttc accatctcca gagataatgc caaaaactcc | 240 |
| ctctatcttc aagctaactc cctaagagct gaggacactg ccgtttacta ctgtgcaaga | 300 |
| gagggccaca ctgctgctcc ttttgattac tggggccaag gaacactggt caccgtctcc | 360 |
| tca | 363 |

<210> SEQ ID NO 95
<211> LENGTH: 363
<212> TYPE: DNA
<213> ORGANISM: ARTIFICIAL
<220> FEATURE:
<223> OTHER INFORMATION: MR

<400> SEQUENCE: 95

| | | | | | |
|---|---|---|---|---|---|
| gaggtgcaac | tgttggaatc | tggaggaggc | ttggtacagc | cgggggttc | tctgagactc | 60 |
| tcctgtgcag | gttctggatt | caccttcact | gatttctaca | tgaactggat | tcgccagcct | 120 |
| cccgggaaag | cacctgagtg | gctgggtttt | attagagaca | aagctaaagg | ttacacaaca | 180 |
| gagtacaatc | catctgtgaa | ggggcggttc | accatctcca | gagataattc | caaaaacacc | 240 |
| ctctatcttc | aagctaactc | cctaagagct | gaggacactg | ccgtttacta | ctgtgcaaga | 300 |
| gagggccaca | ctgctgctcc | ttttgattac | tggggccaag | gaacactggt | caccgtctcc | 360 |
| tca | | | | | | 363 |

<210> SEQ ID NO 96
<211> LENGTH: 363
<212> TYPE: DNA
<213> ORGANISM: ARTIFICIAL
<220> FEATURE:
<223> OTHER INFORMATION: MR

<400> SEQUENCE: 96

| | | | | | |
|---|---|---|---|---|---|
| gaggtgcaac | tgttggaatc | tggaggaggc | ttggtacagc | cgggggttc | tctgagactc | 60 |
| tcctgtgcag | gttctggatt | caccttcact | gatttctaca | tgaactggat | tcgccagcct | 120 |
| cccgggaaag | cacctgagtg | gattggtttt | attagagaca | aagctaaagg | ttacacaaca | 180 |
| gagtacaatc | catctgtgaa | ggggcggttc | accatctcca | gagataattc | ccaaaacacc | 240 |
| ctctatcttc | aaatgaactc | cctaagagct | gaggacactg | ccgtttacta | ctgtgcaaga | 300 |
| gagggccaca | ctgctgctcc | ttttgattac | tggggccaag | gaacactggt | caccgtctcc | 360 |
| tca | | | | | | 363 |

<210> SEQ ID NO 97
<211> LENGTH: 363
<212> TYPE: DNA
<213> ORGANISM: ARTIFICIAL
<220> FEATURE:
<223> OTHER INFORMATION: MR

<400> SEQUENCE: 97

| | | | | | |
|---|---|---|---|---|---|
| gaggtgcaac | tgttggaatc | tggaggaggc | ttggtacagc | cgggggttc | tctgagactc | 60 |
| tcctgtgcag | gttctggatt | caccttcact | gatttctaca | tgaactgggt | ccgccaggct | 120 |
| ccagggaagg | gacttgagtg | ggtgggtttt | attagagaca | aagctaaagg | ttacacaaca | 180 |
| gagtacaatc | catctgtgaa | ggggcggttc | accatctcca | gagataatgc | caaaactcc | 240 |
| ctctatcttc | aaatgaactc | cctaagagct | gaggacactg | ccgtttacta | ctgtgcaaga | 300 |
| gagggccaca | ctgctgctcc | ttttgattac | tggggccaag | gaacactggt | caccgtctcc | 360 |
| tca | | | | | | 363 |

<210> SEQ ID NO 98
<211> LENGTH: 363
<212> TYPE: DNA
<213> ORGANISM: ARTIFICIAL
<220> FEATURE:

<223> OTHER INFORMATION: MR

<400> SEQUENCE: 98

```
gaggtgcaac tgttggaatc tggaggaggc ttggtacagc cgggggggttc tctgagactc    60
tcctgtgcag gttctggatt caccttcact gatttctaca tgaactggat tcgccagcct   120
cccgggaaag cacctgagtg gctgggtttt attagagaca aagctaaagg ttacacaaca   180
gagtacaatc catctgtgaa ggggcggttc accatctcca gagataattc ccaaaacacc   240
ctctatcttc aaatgaactc cctaagagct gaggacactg ccgtttacta ctgtgcaaga   300
gagggccaca ctgctgctcc ttttgattac tggggccaag gaacactggt caccgtctcc   360
tca                                                                 363
```

<210> SEQ ID NO 99
<211> LENGTH: 363
<212> TYPE: DNA
<213> ORGANISM: ARTIFICIAL
<220> FEATURE:
<223> OTHER INFORMATION: MR

<400> SEQUENCE: 99

```
gaggtgcaac tgttggaatc tggaggaggc ttggtacagc cgggggggttc tctgagactc    60
tcctgtgcag gttctggatt caccttcact gatttctaca tgaactggat tcgccagcct   120
cccgggaaag cacctgagtg gattggtttt attagagaca aagctaaagg ttacacaaca   180
gagtacaatc catctgtgaa ggggcggttc accatctcca gagataatac caaaacacc    240
ctctatcttc aaatgaactc cctaagagct gaggacactg ccgtttacta ctgtgcaaga   300
gagggccaca ctgctgctcc ttttgattac tggggccaag gaacactggt caccgtctcc   360
tca                                                                 363
```

<210> SEQ ID NO 100
<211> LENGTH: 363
<212> TYPE: DNA
<213> ORGANISM: ARTIFICIAL
<220> FEATURE:
<223> OTHER INFORMATION: MR

<400> SEQUENCE: 100

```
gaggtgcaac tgttggaatc tggaggaggc ttggtacagc cgggggggttc tctgagactc    60
tcctgtgcag gttctggatt caccttcact gatttctaca tgaactgggt ccgccaggct   120
ccagggaagg gacttgagtg ggtgggtttt attagagaca aagctaaagg ttacacaaca   180
gagtacaatc catctgtgaa ggggcggttc accatctcca gagataatac caaaactcc    240
ctctatcttc aaatgaactc cctaagagct gaggacactg ccgtttacta ctgtgcaaga   300
gagggccaca ctgctgctcc ttttgattac tggggccaag gaacactggt caccgtctcc   360
tca                                                                 363
```

<210> SEQ ID NO 101
<211> LENGTH: 363
<212> TYPE: DNA
<213> ORGANISM: ARTIFICIAL
<220> FEATURE:
<223> OTHER INFORMATION: MR

<400> SEQUENCE: 101

```
gaggtgcaac tgttggaatc tggaggaggc ttggtacagc cgggggggttc tctgagactc    60
tcctgtgcag gttctggatt caccttcact gatttctaca tgaactggat tcgccagcct   120
```

```
cccgggaaag cacctgagtg gctgggtttt attagagaca aagctaaagg ttacacaaca      180
gagtacaatc catctgtgaa ggggcggttc accatctcca gagataatac caaaaacacc      240
ctctatcttc aaatgaactc cctaagagct gaggacactg ccgtttacta ctgtgcaaga      300
gagggccaca ctgctgctcc ttttgattac tggggccaag aacactggt caccgtctcc       360 tca                                                                    363
```

<210> SEQ ID NO 102
<211> LENGTH: 363
<212> TYPE: DNA
<213> ORGANISM: ARTIFICIAL
<220> FEATURE:
<223> OTHER INFORMATION: MR

<400> SEQUENCE: 102

```
gaggtgcaac tgttggaatc tggaggaggc ttggtacagc cgggggggttc tatgagactc      60 tcctgtgcag gttctggatt caccttcact gatttctaca tgaactggat tcgccagcct      120
cccgggaaag cacctgagtg gctgggtttt attagagaca aagctaaagg ttacacaaca      180
gagtacaatc catctgtgaa ggggcggttc accatctcca gagataattc caaaaacacc      240
ctctatcttc aaatgaactc cctaagagct gaggacactg ccgtttacta ctgtgcaaga      300
gagggccaca ctgctgctcc ttttgattac tggggccaag aacactggt caccgtctcc       360 tca                                                                    363
```

<210> SEQ ID NO 103
<211> LENGTH: 363
<212> TYPE: DNA
<213> ORGANISM: ARTIFICIAL
<220> FEATURE:
<223> OTHER INFORMATION: MR

<400> SEQUENCE: 103

```
gaggtgaaac tgcaggaatc tggaggaggc ttggtacagc cgggggggttc tatgagaatc      60 tcctgttcag gttctggatt caccttcact gatttctaca tgaactggat tcgccagcct      120
cccgggaaag gacctgagtg gctgggtttt attagagaca aagctaaagg ttacacaaca      180
gagtacaatc catctgtgaa ggggcggttc accatctcca gagataatac ccaaaacacc      240
ctccatcttc aagctaacac cctaagagct gaggacactg ccgtttacta ctgtgcaaga      300
gagggccaca ctgctgctcc ttttgattac tggggccaag aactaccgt caccgtctcc       360 tca                                                                    363
```

<210> SEQ ID NO 104
<211> LENGTH: 363
<212> TYPE: DNA
<213> ORGANISM: ARTIFICIAL
<220> FEATURE:
<223> OTHER INFORMATION: MR

<400> SEQUENCE: 104

```
gaggtgcaac tgttggaatc tggaggaggc ttggtacagc cgggggggttc tctgagactc      60 tcctgtgcag gttctggatt caccttcact gatttctaca tgaactgggt ccgccaggct      120
ccagggaagg gacttgagtg gctgggtttt attagagaca aagctaaagg ttacacaaca      180
gagtacaatc catctgtgaa ggggcggttc accatctcca gagataatgc caaaaactcc      240
ctctatcttc aaatgaactc cctaagagct gaggacactg ccgtttacta ctgtgcaaga      300
```

```
gagggccaca ctgctgctcc ttttgattac tggggccaag gaacactggt caccgtctcc    360
tca                                                                  363

<210> SEQ ID NO 105
<211> LENGTH: 363
<212> TYPE: DNA
<213> ORGANISM: ARTIFICIAL
<220> FEATURE:
<223> OTHER INFORMATION: MR

<400> SEQUENCE: 105
gaggtgcaac tgttggaatc tggaggaggc ttggtacagc cggggggttc tctgagactc    60
tcctgtgcag gttctggatt caccttcact gatttctaca tgaactggat tcgccagcct   120
cccgggaaag cacctgagtg gattggtttt attagagaca aagctaaagg ttacacaaca   180
gagtacaatc catctgtgaa ggggcggttc accatctcca gagataattc caaaaacacc   240
ctctatcttc aaatgaactc cctaagagct gaggacactg ccgtttacta ctgtgcaaga   300
gagggccaca ctgctgctcc ttttgattac tggggccaag gaacaaccgt caccgtctcc   360
tca                                                                 363

<210> SEQ ID NO 106
<211> LENGTH: 363
<212> TYPE: DNA
<213> ORGANISM: ARTIFICIAL
<220> FEATURE:
<223> OTHER INFORMATION: MR

<400> SEQUENCE: 106
gaggtgcaac tgttggaatc tggaggaggc ttggtacagc cggggggttc tctgagactc    60
tcctgtgcag gttctggatt caccttcact gatttctaca tgaactgggt ccgccaggct   120
ccagggaagg gacttgagtg ggtgggtttt attagagaca aagctaaagg ttacacaaca   180
gagtacaatc catctgtgaa ggggcggttc accatctcca gagataatgc caaaaactcc   240
ctctatcttc aaatgaactc cctaagagct gaggacactg ccgtttacta ctgtgcaaga   300
gagggccaca ctgctgctcc ttttgattac tggggccaag gaacaaccgt caccgtctcc   360
tca                                                                 363

<210> SEQ ID NO 107
<211> LENGTH: 363
<212> TYPE: DNA
<213> ORGANISM: ARTIFICIAL
<220> FEATURE:
<223> OTHER INFORMATION: MR

<400> SEQUENCE: 107
gaggtgcaac tgttggaatc tggaggaggc ttggtacagc cggggggttc tctgagactc    60
tcctgtgcag gttctggatt caccttcact gatttctaca tgaactggat tcgccagcct   120
cccgggaaag cacctgagtg gctgggtttt attagagaca aagctaaagg ttacacaaca   180
gagtacaatc catctgtgaa ggggcggttc accatctcca gagataattc caaaaacacc   240
ctctatcttc aaatgaactc cctaagagct gaggacactg ccgtttacta ctgtgcaaga   300
gagggccaca ctgctgctcc ttttgattac tggggccaag gaacaaccgt caccgtctcc   360
tca                                                                 363

<210> SEQ ID NO 108
<211> LENGTH: 363
```

<212> TYPE: DNA
<213> ORGANISM: ARTIFICIAL
<220> FEATURE:
<223> OTHER INFORMATION: MR

<400> SEQUENCE: 108
gaggtgcaac tgttggaatc tggaggaggc ttggtacagc cgggggggttc tctgagactc    60 tcctgtgcag gttctggatt caccttcact gatttctaca tgaactggat tcgccagcct   120
cccgggaaag cacctgagtg gctgggtttt attagagaca aagctaaagg ttacacaaca   180
gagtacaatc catctgtgaa ggggcggttc accatctcca gagataattc caaaaacacc   240
ctctatcttc aaatgaactc cctaagagct gaggacactg ccacctacta ctgtgcaaga   300
gagggccaca ctgctgctcc ttttgattac tggggccaag gaacactggt caccgtctcc   360
tca                                                                  363

<210> SEQ ID NO 109
<211> LENGTH: 321
<212> TYPE: DNA
<213> ORGANISM: ARTIFICIAL
<220> FEATURE:
<223> OTHER INFORMATION: MR

<400> SEQUENCE: 109
gacatccaga tgacccagtc tccctcagcc ctgtctgcat ctgtgggaga cagagtcact    60
cccacctgca gagcaagtca gaatattgac aaatacttaa actggtatca gcaaaagccc   120
ggaaaagctc ccaaatccct gatatataat acaaacaatt tgcaatctgg cgtcccatca   180
aggttcagtg gcagtggatc tggtactgat ttcacactca ccatcagcag cctgcagcct   240
gaagatattg ccacatatta ctgcttgcag catataagta ggccgcgcac gtttggaact   300
gggaccaagc tggagctgaa a                                              321

<210> SEQ ID NO 110
<211> LENGTH: 321
<212> TYPE: DNA
<213> ORGANISM: ARTIFICIAL
<220> FEATURE:
<223> OTHER INFORMATION: MR

<400> SEQUENCE: 110
gacatccaga tgacccagtc tccctcagcc ctgtctgcat ctgtgggaga cagagtcact    60
cccacctgca aagcaagtca gaatattgac aaatacttaa actggtatca gcaaaagccc   120
ggaaaagctc ccaaactcct gatatataat acaaacaatt tgcaaacggg cgtcccatca   180
aggttcagtg gcagtggatc tggtactgat ttcacactca ccatcagcag cctgcagcct   240
gaagatattg ccacatatta ctgcttgcag catataagta ggccgcgcac gtttggaact   300
gggaccaagc tggagctgaa a                                              321

<210> SEQ ID NO 111
<211> LENGTH: 321
<212> TYPE: DNA
<213> ORGANISM: ARTIFICIAL
<220> FEATURE:
<223> OTHER INFORMATION: MR

<400> SEQUENCE: 111
gacatccaga tgacccagtc tccctcagcc ctgtctgcat ctgtgggaga cagagtcact    60
cccacctgca gagcaagtca gaatattgac aaatacttaa actggtatca gcaaaagccc   120

-continued

```
ggaaaagctc ccaaactcct gatatataat acaaacaatt tgcaatctgg cgtcccatca      180
aggttcagtg gcagtggatc tggtactgat ttcacactca ccatcagcag cctgcagcct      240
gaagatattg ccacatatta ctgcttgcag catataagta ggccgcgcac gtttggaact      300
gggaccaagc tggagctgaa a                                                 321
```

<210> SEQ ID NO 112
<211> LENGTH: 321
<212> TYPE: DNA
<213> ORGANISM: ARTIFICIAL
<220> FEATURE:
<223> OTHER INFORMATION: MR

<400> SEQUENCE: 112

```
gacatccaga tgacccagtc tccctcagcc ctgtctgcat ctgtgggaga cagagtcact      60
cccacctgca aagcaagtca gaatattgac aaatacttaa actggtatca gcaaaagccc     120
ggaaaagctc ccaaatccct gatatataat acaaacaatt tgcaaacggg cgtcccatca     180
aggttcagtg gcagtggatc tggtactgat ttcacactca ccatcagcag cctgcagcct     240
gaagatattg ccacatatta ctgcttgcag catataagta ggccgcgcac gtttggaact     300
gggaccaagc tggagctgaa a                                                321
```

<210> SEQ ID NO 113
<211> LENGTH: 321
<212> TYPE: DNA
<213> ORGANISM: ARTIFICIAL
<220> FEATURE:
<223> OTHER INFORMATION: MR

<400> SEQUENCE: 113

```
gacatccaga tgacccagtc tccctcagcc ctgtctgcat ctgtgggaga cagagtcact      60
cccacctgca aagcaagtca gaatattgac aaatacttaa actggtatca gcaaaagccc     120
ggaaaatctc ccaaactcct gatatataat acaaacaatt tgcaaacggg cgtcccatca     180
aggttcagtg gcagtggatc tggtactgat ttcacactca ccatcagcag cctgcagcct     240
gaagatattg ccacatatta ctgcttgcag catataagta ggccgcgcac gtttggaact     300
gggaccaagc tggagctgaa a                                                321
```

<210> SEQ ID NO 114
<211> LENGTH: 321
<212> TYPE: DNA
<213> ORGANISM: ARTIFICIAL
<220> FEATURE:
<223> OTHER INFORMATION: MR

<400> SEQUENCE: 114

```
gacatccaga tgacccagtc tccctcagcc ctgtctgcat ctgtgggaga cagagtcact      60
atcacctgca gagcaagtca gaatattgac aaatacttaa actggtatca gcaaaagccc     120
ggaaaagctc ccaaatccct gatatataat acaaacaatt tgcaatctgg cgtcccatca     180
aggttcagtg gcagtggatc tggtactgat ttcacactca ccatcagcag cctgcagcct     240
gaagatattg ccacatatta ctgcttgcag catataagta ggccgcgcac gtttggaact     300
gggaccaagc tggagctgaa a                                                321
```

<210> SEQ ID NO 115
<211> LENGTH: 321
<212> TYPE: DNA
<213> ORGANISM: ARTIFICIAL

<220> FEATURE:
<223> OTHER INFORMATION: MR

<400> SEQUENCE: 115

| | | | | | |
|---|---|---|---|---|---|
| gacatccaga | tgacccagtc | tccctcagcc | ctgtctgcat | ctgtgggaga | cagagtcact | 60 |
| atcacctgca | aagcaagtca | gaatattgac | aaatacttaa | actggtatca | gcaaaagccc | 120 |
| ggaaaagctc | ccaaactcct | gatatataat | acaaacaatt | tgcaaacggg | cgtcccatca | 180 |
| aggttcagtg | gcagtggatc | tggtactgat | ttcacactca | ccatcagcag | cctgcagcct | 240 |
| gaagatattg | ccacatatta | ctgcttgcag | catataagta | ggccgcgcac | gtttggaact | 300 |
| gggaccaagc | tggagctgaa | a | | | | 321 |

<210> SEQ ID NO 116
<211> LENGTH: 321
<212> TYPE: DNA
<213> ORGANISM: ARTIFICIAL
<220> FEATURE:
<223> OTHER INFORMATION: MR

<400> SEQUENCE: 116

| | | | | | |
|---|---|---|---|---|---|
| gacatccaga | tgacccagtc | tccctcagcc | ctgtctgcat | ctgtgggaga | cagagtcact | 60 |
| atcacctgca | gagcaagtca | gaatattgac | aaatacttaa | actggtatca | gcaaaagccc | 120 |
| ggaaaagctc | ccaaactcct | gatatataat | acaaacaatt | tgcaatctgg | cgtcccatca | 180 |
| aggttcagtg | gcagtggatc | tggtactgat | ttcacactca | ccatcagcag | cctgcagcct | 240 |
| gaagatattg | ccacatatta | ctgcttgcag | catataagta | ggccgcgcac | gtttggaact | 300 |
| gggaccaagc | tggagctgaa | a | | | | 321 |

<210> SEQ ID NO 117
<211> LENGTH: 321
<212> TYPE: DNA
<213> ORGANISM: ARTIFICIAL
<220> FEATURE:
<223> OTHER INFORMATION: MR

<400> SEQUENCE: 117

| | | | | | |
|---|---|---|---|---|---|
| gacatccaga | tgacccagtc | tccctcagcc | ctgtctgcat | ctgtgggaga | cagagtcact | 60 |
| atcacctgca | aagcaagtca | gaatattgac | aaatacttaa | actggtatca | gcaaaagccc | 120 |
| ggaaaagctc | ccaaatccct | gatatataat | acaaacaatt | tgcaaacggg | cgtcccatca | 180 |
| aggttcagtg | gcagtggatc | tggtactgat | ttcacactca | ccatcagcag | cctgcagcct | 240 |
| gaagatattg | ccacatatta | ctgcttgcag | catataagta | ggccgcgcac | gtttggaact | 300 |
| gggaccaagc | tggagctgaa | a | | | | 321 |

<210> SEQ ID NO 118
<211> LENGTH: 321
<212> TYPE: DNA
<213> ORGANISM: ARTIFICIAL
<220> FEATURE:
<223> OTHER INFORMATION: MR

<400> SEQUENCE: 118

| | | | | | |
|---|---|---|---|---|---|
| gacatccaga | tgacccagtc | tccctcagcc | ctgtctgcat | ctgtgggaga | cagagtcact | 60 |
| atcacctgca | aagcaagtca | gaatattgac | aaatacttaa | actggtatca | gcaaaagccc | 120 |
| ggaaaatctc | ccaaactcct | gatatataat | acaaacaatt | tgcaaacggg | cgtcccatca | 180 |
| aggttcagtg | gcagtggatc | tggtactgat | ttcacactca | ccatcagcag | cctgcagcct | 240 |

```
gaagatattg ccacatatta ctgcttgcag catataagta ggccgcgcac gtttggaact        300
gggaccaagc tggagctgaa a                                                  321
```

<210> SEQ ID NO 119
<211> LENGTH: 321
<212> TYPE: DNA
<213> ORGANISM: ARTIFICIAL
<220> FEATURE:
<223> OTHER INFORMATION: MR

<400> SEQUENCE: 119

```
gacatccaga tgacccagtc tccctcatcc ctgtctgcat ctgtgggaga cagagtcact         60
cccacctgca gagcaagtca gaatattgac aaatacttaa actggtatca gcaaaagccc        120
ggaaaagctc ccaaatccct gatatataat acaaacaatt tgcaatctgg cgtcccatca        180
aggttcagtg gcagtggatc tggtactgat ttcacactca ccatcagcag cctgcagcct        240
gaagatattg ccacatatta ctgcttgcag catataagta ggccgcgcac gtttggaact        300
gggaccaagc tggagctgaa a                                                  321
```

<210> SEQ ID NO 120
<211> LENGTH: 321
<212> TYPE: DNA
<213> ORGANISM: ARTIFICIAL
<220> FEATURE:
<223> OTHER INFORMATION: MR

<400> SEQUENCE: 120

```
gacatccaga tgacccagtc tccctcatcc ctgtctgcat ctgtgggaga cagagtcact         60
cccacctgca aagcaagtca gaatattgac aaatacttaa actggtatca gcaaaagccc        120
ggaaaagctc ccaaactcct gatatataat acaaacaatt tgcaaacggg cgtcccatca        180
aggttcagtg gcagtggatc tggtactgat ttcacactca ccatcagcag cctgcagcct        240
gaagatattg ccacatatta ctgcttgcag catataagta ggccgcgcac gtttggaact        300
gggaccaagc tggagctgaa a                                                  321
```

<210> SEQ ID NO 121
<211> LENGTH: 321
<212> TYPE: DNA
<213> ORGANISM: ARTIFICIAL
<220> FEATURE:
<223> OTHER INFORMATION: MR

<400> SEQUENCE: 121

```
gacatccaga tgacccagtc tccctcatcc ctgtctgcat ctgtgggaga cagagtcact         60
cccacctgca gagcaagtca gaatattgac aaatacttaa actggtatca gcaaaagccc        120
ggaaaagctc ccaaactcct gatatataat acaaacaatt tgcaatctgg cgtcccatca        180
aggttcagtg gcagtggatc tggtactgat ttcacactca ccatcagcag cctgcagcct        240
gaagatattg ccacatatta ctgcttgcag catataagta ggccgcgcac gtttggaact        300
gggaccaagc tggagctgaa a                                                  321
```

<210> SEQ ID NO 122
<211> LENGTH: 321
<212> TYPE: DNA
<213> ORGANISM: ARTIFICIAL
<220> FEATURE:
<223> OTHER INFORMATION: MR

<400> SEQUENCE: 122

```
gacatccaga tgacccagtc tccctcatcc ctgtctgcat ctgtgggaga cagagtcact    60
cccacctgca aagcaagtca gaatattgac aaatactta a actggtatca gcaaaagccc   120
ggaaaagctc ccaaatccct gatatataat acaaacaatt tgcaaacggg cgtcccatca   180
aggttcagtg gcagtggatc tggtactgat ttcacactca ccatcagcag cctgcagcct   240
gaagatattg ccacatatta ctgcttgcag catataagta ggccgcgcac gtttggaact   300
gggaccaagc tggagctgaa a                                              321
```

<210> SEQ ID NO 123
<211> LENGTH: 321
<212> TYPE: DNA
<213> ORGANISM: ARTIFICIAL
<220> FEATURE:
<223> OTHER INFORMATION: MR

<400> SEQUENCE: 123

```
gacatccaga tgacccagtc tccctcatcc ctgtctgcat ctgtgggaga cagagtcact    60
cccacctgca aagcaagtca gaatattgac aaatacttaa actggtatca gcaaaagccc   120
ggaaaatctc ccaaactcct gatatataat acaaacaatt tgcaaacggg cgtcccatca   180
aggttcagtg gcagtggatc tggtactgat ttcacactca ccatcagcag cctgcagcct   240
gaagatattg ccacatatta ctgcttgcag catataagta ggccgcgcac gtttggaact   300
gggaccaagc tggagctgaa a                                              321
```

<210> SEQ ID NO 124
<211> LENGTH: 321
<212> TYPE: DNA
<213> ORGANISM: ARTIFICIAL
<220> FEATURE:
<223> OTHER INFORMATION: MR

<400> SEQUENCE: 124

```
gacatccaga tgacccagtc tccctcatcc ctgtctgcat ctgtgggaga cagagtcact    60
atcacctgca gagcaagtca gaatattgac aaatacttaa actggtatca gcaaaagtct   120
ggaaaagctc ccaaatccct gatatataat acaaacaatt tgcaatctgg cgtcccatca   180
aggttcagtg gcagtggatc tggtactgat ttcacactca ccatcagcag cctgcagcct   240
gaagatattg ccacatatta ctgcttgcag catataagta ggccgcgcac gtttggaact   300
gggaccaagc tggagctgaa a                                              321
```

<210> SEQ ID NO 125
<211> LENGTH: 321
<212> TYPE: DNA
<213> ORGANISM: ARTIFICIAL
<220> FEATURE:
<223> OTHER INFORMATION: MR

<400> SEQUENCE: 125

```
gacatccaga tgacccagtc tccctcatcc ctgtctgcat ctgtgggaga cagagtcact    60
atcacctgca aagcaagtca gaatattgac aaatacttaa actggtatca gcaaaagtct   120
ggaaaagctc ccaaactcct gatatataat acaaacaatt tgcaaacggg cgtcccatca   180
aggttcagtg gcagtggatc tggtactgat ttcacactca ccatcagcag cctgcagcct   240
gaagatattg ccacatatta ctgcttgcag catataagta ggccgcgcac gtttggaact   300
gggaccaagc tggagctgaa a                                              321
```

<210> SEQ ID NO 126
<211> LENGTH: 321
<212> TYPE: DNA
<213> ORGANISM: ARTIFICIAL
<220> FEATURE:
<223> OTHER INFORMATION: MR

<400> SEQUENCE: 126
gacatccaga tgacccagtc tccctcatcc ctgtctgcat ctgtgggaga cagagtcact      60
atcacctgca gagcaagtca gaatattgac aaatacttaa actggtatca gcaaaagtct     120
ggaaaagctc ccaaactcct gatatataat acaaacaatt tgcaatctgg cgtcccatca     180
aggttcagtg gcagtggatc tggtactgat ttcacactca ccatcagcag cctgcagcct     240
gaagatattg ccacatatta ctgcttgcag catataagta ggccgcgcac gtttggaact     300
gggaccaagc tggagctgaa a                                              321

<210> SEQ ID NO 127
<211> LENGTH: 321
<212> TYPE: DNA
<213> ORGANISM: ARTIFICIAL
<220> FEATURE:
<223> OTHER INFORMATION: MR

<400> SEQUENCE: 127
gacatccaga tgacccagtc tccctcatcc ctgtctgcat ctgtgggaga cagagtcact      60
atcacctgca aagcaagtca gaatattgac aaatacttaa actggtatca gcaaaagtct     120
ggaaaagctc ccaaatccct gatatataat acaaacaatt tgcaaacggg cgtcccatca     180
aggttcagtg gcagtggatc tggtactgat ttcacactca ccatcagcag cctgcagcct     240
gaagatattg ccacatatta ctgcttgcag catataagta ggccgcgcac gtttggaact     300
gggaccaagc tggagctgaa a                                              321

<210> SEQ ID NO 128
<211> LENGTH: 321
<212> TYPE: DNA
<213> ORGANISM: ARTIFICIAL
<220> FEATURE:
<223> OTHER INFORMATION: MR

<400> SEQUENCE: 128
gacatccaga tgacccagtc tccctcatcc ctgtctgcat ctgtgggaga cagagtcact      60
atcacctgca aagcaagtca gaatattgac aaatacttaa actggtatca gcaaaagtct     120
ggaaaatctc ccaaactcct gatatataat acaaacaatt tgcaaacggg cgtcccatca     180
aggttcagtg gcagtggatc tggtactgat ttcacactca ccatcagcag cctgcagcct     240
gaagatattg ccacatatta ctgcttgcag catataagta ggccgcgcac gtttggaact     300
gggaccaagc tggagctgaa a                                              321

<210> SEQ ID NO 129
<211> LENGTH: 321
<212> TYPE: DNA
<213> ORGANISM: ARTIFICIAL
<220> FEATURE:
<223> OTHER INFORMATION: MR

<400> SEQUENCE: 129
gacatccaga tgacccagtc tccctcatcc ctgtctgcat ctgtgggaga cagagtcact      60
atcacctgca gagcaagtca gaatattgac aaatacttaa actggtatca gcaaaagccc     120

```
ggaaaagctc ccaaatccct gatatataat acaaacaatt tgcaatctgg catgccatca      180
aggttcagtg gcagtggatc tggtactgat ttcacactca ccatcagcag cctgcagcct      240
gaagatattg ccacatatta ctgcttgcag catataagta ggccgcgcac gtttggaact      300
gggaccaagc tggagctgaa a                                                 321

<210> SEQ ID NO 130
<211> LENGTH: 321
<212> TYPE: DNA
<213> ORGANISM: ARTIFICIAL
<220> FEATURE:
<223> OTHER INFORMATION: MR

<400> SEQUENCE: 130
gacatccaga tgacccagtc tccctcatcc ctgtctgcat ctgtgggaga cagagtcact       60
atcacctgca aagcaagtca gaatattgac aaatacttaa actggtatca gcaaaagccc      120
ggaaaagctc ccaaactcct gatatataat acaaacaatt tgcaaacggg catgccatca      180
aggttcagtg gcagtggatc tggtactgat ttcacactca ccatcagcag cctgcagcct      240
gaagatattg ccacatatta ctgcttgcag catataagta ggccgcgcac gtttggaact      300
gggaccaagc tggagctgaa a                                                 321

<210> SEQ ID NO 131
<211> LENGTH: 321
<212> TYPE: DNA
<213> ORGANISM: ARTIFICIAL
<220> FEATURE:
<223> OTHER INFORMATION: MR

<400> SEQUENCE: 131
gacatccaga tgacccagtc tccctcatcc ctgtctgcat ctgtgggaga cagagtcact       60
atcacctgca gagcaagtca gaatattgac aaatacttaa actggtatca gcaaaagccc      120
ggaaaagctc ccaaactcct gatatataat acaaacaatt tgcaatctgg catgccatca      180
aggttcagtg gcagtggatc tggtactgat ttcacactca ccatcagcag cctgcagcct      240
gaagatattg ccacatatta ctgcttgcag catataagta ggccgcgcac gtttggaact      300
gggaccaagc tggagctgaa a                                                 321

<210> SEQ ID NO 132
<211> LENGTH: 321
<212> TYPE: DNA
<213> ORGANISM: ARTIFICIAL
<220> FEATURE:
<223> OTHER INFORMATION: MR

<400> SEQUENCE: 132
gacatccaga tgacccagtc tccctcatcc ctgtctgcat ctgtgggaga cagagtcact       60
atcacctgca aagcaagtca gaatattgac aaatacttaa actggtatca gcaaaagccc      120
ggaaaagctc ccaaatccct gatatataat acaaacaatt tgcaaacggg catgccatca      180
aggttcagtg gcagtggatc tggtactgat ttcacactca ccatcagcag cctgcagcct      240
gaagatattg ccacatatta ctgcttgcag catataagta ggccgcgcac gtttggaact      300
gggaccaagc tggagctgaa a                                                 321

<210> SEQ ID NO 133
<211> LENGTH: 321
<212> TYPE: DNA
```

<213> ORGANISM: ARTIFICIAL
<220> FEATURE:
<223> OTHER INFORMATION: MR

<400> SEQUENCE: 133

| | | |
|---|---|---|
| gacatccaga tgacccagtc tccctcatcc ctgtctgcat ctgtgggaga cagagtcact | 60 |
| atcacctgca aagcaagtca gaatattgac aaatacttaa actggtatca gcaaaagccc | 120 |
| ggaaaatctc ccaaactcct gatatataat acaaacaatt tgcaaacggg catgccatca | 180 |
| aggttcagtg gcagtggatc tggtactgat ttcacactca ccatcagcag cctgcagcct | 240 |
| gaagatattg ccacatatta ctgcttgcag catataagta ggccgcgcac gtttggaact | 300 |
| gggaccaagc tggagctgaa a | 321 |

<210> SEQ ID NO 134
<211> LENGTH: 321
<212> TYPE: DNA
<213> ORGANISM: ARTIFICIAL
<220> FEATURE:
<223> OTHER INFORMATION: MR

<400> SEQUENCE: 134

| | | |
|---|---|---|
| gacatccaga tgacccagtc tccctcatcc ctgtctgcat ctgtgggaga cagagtcact | 60 |
| atcacctgca gagcaagtca gaatattgac aaatacttaa actggtatca gcaaaagtct | 120 |
| ggaaaagctc ccaaatccct gatatataat acaaacaatt tgcaatctgg catgccatca | 180 |
| aggttcagtg gcagtggatc tggtactgat ttcacactca ccatcagcag cctgcagcct | 240 |
| gaagatattg ccacatatta ctgcttgcag catataagta ggccgcgcac gtttggaact | 300 |
| gggaccaagc tggagctgaa a | 321 |

<210> SEQ ID NO 135
<211> LENGTH: 321
<212> TYPE: DNA
<213> ORGANISM: ARTIFICIAL
<220> FEATURE:
<223> OTHER INFORMATION: MR

<400> SEQUENCE: 135

| | | |
|---|---|---|
| gacatccaga tgacccagtc tccctcatcc ctgtctgcat ctgtgggaga cagagtcact | 60 |
| atcacctgca aagcaagtca gaatattgac aaatacttaa actggtatca gcaaaagtct | 120 |
| ggaaaagctc ccaaactcct gatatataat acaaacaatt tgcaaacggg catgccatca | 180 |
| aggttcagtg gcagtggatc tggtactgat ttcacactca ccatcagcag cctgcagcct | 240 |
| gaagatattg ccacatatta ctgcttgcag catataagta ggccgcgcac gtttggaact | 300 |
| gggaccaagc tggagctgaa a | 321 |

<210> SEQ ID NO 136
<211> LENGTH: 321
<212> TYPE: DNA
<213> ORGANISM: ARTIFICIAL
<220> FEATURE:
<223> OTHER INFORMATION: MR

<400> SEQUENCE: 136

| | | |
|---|---|---|
| gacatccaga tgacccagtc tccctcatcc ctgtctgcat ctgtgggaga cagagtcact | 60 |
| atcacctgca gagcaagtca gaatattgac aaatacttaa actggtatca gcaaaagtct | 120 |
| ggaaaagctc ccaaactcct gatatataat acaaacaatt tgcaatctgg catgccatca | 180 |
| aggttcagtg gcagtggatc tggtactgat ttcacactca ccatcagcag cctgcagcct | 240 |

```
gaagatattg ccacatatta ctgcttgcag catataagta ggccgcgcac gtttggaact    300
gggaccaagc tggagctgaa a                                              321
```

<210> SEQ ID NO 137
<211> LENGTH: 321
<212> TYPE: DNA
<213> ORGANISM: ARTIFICIAL
<220> FEATURE:
<223> OTHER INFORMATION: MR

<400> SEQUENCE: 137

```
gacatccaga tgacccagtc tccctcatcc ctgtctgcat ctgtgggaga cagagtcact     60
atcacctgca aagcaagtca gaatattgac aaatacttaa actggtatca gcaaaagtct    120
ggaaaagctc ccaaatccct gatatataat acaaacaatt tgcaaacggg catgccatca    180
aggttcagtg gcagtggatc tggtactgat ttcacactca ccatcagcag cctgcagcct    240
gaagatattg ccacatatta ctgcttgcag catataagta ggccgcgcac gtttggaact    300
gggaccaagc tggagctgaa a                                              321
```

<210> SEQ ID NO 138
<211> LENGTH: 321
<212> TYPE: DNA
<213> ORGANISM: ARTIFICIAL
<220> FEATURE:
<223> OTHER INFORMATION: MR

<400> SEQUENCE: 138

```
gacatccaga tgacccagtc tccctcatcc ctgtctgcat ctgtgggaga cagagtcact     60
atcacctgca aagcaagtca gaatattgac aaatacttaa actggtatca gcaaaagtct    120
ggaaaatctc ccaaactcct gatatataat acaaacaatt tgcaaacggg catgccatca    180
aggttcagtg gcagtggatc tggtactgat ttcacactca ccatcagcag cctgcagcct    240
gaagatattg ccacatatta ctgcttgcag catataagta ggccgcgcac gtttggaact    300
gggaccaagc tggagctgaa a                                              321
```

<210> SEQ ID NO 139
<211> LENGTH: 330
<212> TYPE: PRT
<213> ORGANISM: Homo Sapiens

<400> SEQUENCE: 139

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
```

-continued

```
                 115                 120                 125
Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 140
<211> LENGTH: 106
<212> TYPE: PRT
<213> ORGANISM: Homo Sapiens

<400> SEQUENCE: 140

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Leu Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 141
<211> LENGTH: 20
<212> TYPE: DNA
<213> ORGANISM: ARTIFICIAL
<220> FEATURE:
<223> OTHER INFORMATION: SYNTHESIZED

<400> SEQUENCE: 141
```
tccacaggtg tccactccga                                            20

<210> SEQ ID NO 142
<211> LENGTH: 41
<212> TYPE: DNA
<213> ORGANISM: ARTIFICIAL
<220> FEATURE:
<223> OTHER INFORMATION: SYNTHESIZED

<400> SEQUENCE: 142
ccagattcca acagtttcac ctcggagtgg acacctgtgg a                    41

<210> SEQ ID NO 143
<211> LENGTH: 39
<212> TYPE: DNA
<213> ORGANISM: ARTIFICIAL
<220> FEATURE:
<223> OTHER INFORMATION: SYNTHESIZED

<400> SEQUENCE: 143
ggtgaaactg ttggaatctg gaggaggctt ggtacagcc                       39

<210> SEQ ID NO 144
<211> LENGTH: 40
<212> TYPE: DNA
<213> ORGANISM: ARTIFICIAL
<220> FEATURE:
<223> OTHER INFORMATION: SYNTHESIZED

<400> SEQUENCE: 144
ggagagtctc atagaacccc ccggctgtac caagcctcct                      40

<210> SEQ ID NO 145
<211> LENGTH: 41
<212> TYPE: DNA
<213> ORGANISM: ARTIFICIAL
<220> FEATURE:
<223> OTHER INFORMATION: SYNTHESIED

<400> SEQUENCE: 145 gggggttct atgagactct cctgtgcagg ttctggattc a                     41

<210> SEQ ID NO 146
<211> LENGTH: 39
<212> TYPE: DNA
<213> ORGANISM: ARTIFICIAL
<220> FEATURE:
<223> OTHER INFORMATION: SYNTHESIZED

<400> SEQUENCE: 146
catgtagaaa tcagtgaagg tgaatccaga acctgcaca                       39

<210> SEQ ID NO 147
<211> LENGTH: 40
<212> TYPE: DNA
<213> ORGANISM: ARTIFICIAL
<220> FEATURE:
<223> OTHER INFORMATION: SYNTHESIZED

<400> SEQUENCE: 147
ccttcactga tttctacatg aactggattc gccagcctgc                      40

<210> SEQ ID NO 148
<211> LENGTH: 40
<212> TYPE: DNA

<213> ORGANISM: ARTIFICIAL
<220> FEATURE:
<223> OTHER INFORMATION: SYNTHESIZED

<400> SEQUENCE: 148
gccactcagg tgccttccct gcaggctggc gaatccagtt                    40

<210> SEQ ID NO 149
<211> LENGTH: 40
<212> TYPE: DNA
<213> ORGANISM: ARTIFICIAL
<220> FEATURE:
<223> OTHER INFORMATION: SYNTHESIZED

<400> SEQUENCE: 149
agggaaggca cctgagtggc tgggttttat tagagacaaa                    40

<210> SEQ ID NO 150
<211> LENGTH: 40
<212> TYPE: DNA
<213> ORGANISM: ARTIFICIAL
<220> FEATURE:
<223> OTHER INFORMATION: SYNTHESIZED

<400> SEQUENCE: 150
tctgttgtgt aacctttagc tttgtctcta ataaaaccca                    40

<210> SEQ ID NO 151
<211> LENGTH: 42
<212> TYPE: DNA
<213> ORGANISM: ARTIFICIAL
<220> FEATURE:
<223> OTHER INFORMATION: SYNTHESIZED

<400> SEQUENCE: 151
gctaaaggtt acacaacaga gtacaatcca tctgtgaagg gg                 42

<210> SEQ ID NO 152
<211> LENGTH: 40
<212> TYPE: DNA
<213> ORGANISM: ARTIFICIAL
<220> FEATURE:
<223> OTHER INFORMATION: SYNTHESIZED

<400> SEQUENCE: 152
tctggagatg gtgaaccgcc ccttcacaga tggattgtac                    40

<210> SEQ ID NO 153
<211> LENGTH: 38
<212> TYPE: DNA
<213> ORGANISM: ARTIFICIAL
<220> FEATURE:
<223> OTHER INFORMATION: SYNTHESIZED

<400> SEQUENCE: 153
cggttcacca tctccagaga taatacccaa aacatgct                      38

<210> SEQ ID NO 154
<211> LENGTH: 40
<212> TYPE: DNA
<213> ORGANISM: ARTIFICIAL
<220> FEATURE:
<223> OTHER INFORMATION: SYNTHESIZED

<400> SEQUENCE: 154
gggtgttcat ttgaagatag agcatgtttt gggtattatc                    40

<210> SEQ ID NO 155
<211> LENGTH: 40
<212> TYPE: DNA
<213> ORGANISM: ARTIFICIAL
<220> FEATURE:
<223> OTHER INFORMATION: SYNTHESIZED

<400> SEQUENCE: 155
ctatcttcaa atgaacaccc taagagctga ggacactgcc                                      40

<210> SEQ ID NO 156
<211> LENGTH: 40
<212> TYPE: DNA
<213> ORGANISM: ARTIFICIAL
<220> FEATURE:
<223> OTHER INFORMATION: SYNTHESIZED

<400> SEQUENCE: 156
tctcttgcac agtagtaagt ggcagtgtcc tcagctctta                                      40

<210> SEQ ID NO 157
<211> LENGTH: 42
<212> TYPE: DNA
<213> ORGANISM: ARTIFICIAL
<220> FEATURE:
<223> OTHER INFORMATION: SYNTHESIZED

<400> SEQUENCE: 157
acttactact gtgcaagaga gggccacact gctgctcctt tt                                   42

<210> SEQ ID NO 158
<211> LENGTH: 41
<212> TYPE: DNA
<213> ORGANISM: ARTIFICIAL
<220> FEATURE:
<223> OTHER INFORMATION: SYNTHESIZED

<400> SEQUENCE: 158
ctccttggcc ccagtaatca aaaggagcag cagtgtggcc c                                    41

<210> SEQ ID NO 159
<211> LENGTH: 39
<212> TYPE: DNA
<213> ORGANISM: ARTIFICIAL
<220> FEATURE:
<223> OTHER INFORMATION: SYNTHESIZED

<400> SEQUENCE: 159
gattactggg gccaaggagt catggtcacc gtctcctca                                       39

<210> SEQ ID NO 160
<211> LENGTH: 20
<212> TYPE: DNA
<213> ORGANISM: ARTIFICIAL
<220> FEATURE:
<223> OTHER INFORMATION: SYNTHESIZED

<400> SEQUENCE: 160
tgaggagacg gtgaccatga                                                            20

<210> SEQ ID NO 161
<211> LENGTH: 38
<212> TYPE: DNA
<213> ORGANISM: ARTIFICIAL
<220> FEATURE:

-continued

<223> OTHER INFORMATION: SYNTHESIZED

<400> SEQUENCE: 161
gcatgttgac cctgacgcaa gcttgccgcc accatggg        38

<210> SEQ ID NO 162
<211> LENGTH: 27
<212> TYPE: DNA
<213> ORGANISM: ARTIFICIAL
<220> FEATURE:
<223> OTHER INFORMATION: SYNTHESIZED

<400> SEQUENCE: 162
ggagtggaca cctgtggaga gaaaggc        27

<210> SEQ ID NO 163
<211> LENGTH: 36
<212> TYPE: DNA
<213> ORGANISM: ARTIFICIAL
<220> FEATURE:
<223> OTHER INFORMATION: SYNTHESIZED

<400> SEQUENCE: 163
gcgatagctg gactgaatgg atcctataaa tctctg        36

<210> SEQ ID NO 164
<211> LENGTH: 21
<212> TYPE: DNA
<213> ORGANISM: ARTIFICIAL
<220> FEATURE:
<223> OTHER INFORMATION: SYNTHESIZED

<400> SEQUENCE: 164
tccacaggtg tccactccga c        21

<210> SEQ ID NO 165
<211> LENGTH: 39
<212> TYPE: DNA
<213> ORGANISM: ARTIFICIAL
<220> FEATURE:
<223> OTHER INFORMATION: SYNTHESIZED

<400> SEQUENCE: 165
agactgggtc atcttgatgt cggagtggac acctgtgga        39

<210> SEQ ID NO 166
<211> LENGTH: 40
<212> TYPE: DNA
<213> ORGANISM: ARTIFICIAL
<220> FEATURE:
<223> OTHER INFORMATION: SYNTHESIZED

<400> SEQUENCE: 166
atcaagatga cccagtctcc ctcattcctg tctgcatctg        40

<210> SEQ ID NO 167
<211> LENGTH: 41
<212> TYPE: DNA
<213> ORGANISM: ARTIFICIAL
<220> FEATURE:
<223> OTHER INFORMATION: SYNTHESIZED

<400> SEQUENCE: 167
agagtgactc tgtctcccac agatgcagac aggaatgagg g        41

```
<210> SEQ ID NO 168
<211> LENGTH: 40
<212> TYPE: DNA
<213> ORGANISM: ARTIFICIAL
<220> FEATURE:
<223> OTHER INFORMATION: SYNTHESIZED

<400> SEQUENCE: 168
tgggagacag agtcactctc aactgcaaag caagtcagaa                    40

<210> SEQ ID NO 169
<211> LENGTH: 40
<212> TYPE: DNA
<213> ORGANISM: ARTIFICIAL
<220> FEATURE:
<223> OTHER INFORMATION: SYNTHESIZED

<400> SEQUENCE: 169
gtttaagtat ttgtcaatat tctgacttgc tttgcagttg                    40

<210> SEQ ID NO 170
<211> LENGTH: 40
<212> TYPE: DNA
<213> ORGANISM: ARTIFICIAL
<220> FEATURE:
<223> OTHER INFORMATION: SYNTHESIZED

<400> SEQUENCE: 170
tattgacaaa tacttaaact ggtatcagca aaagctggga                    40

<210> SEQ ID NO 171
<211> LENGTH: 40
<212> TYPE: DNA
<213> ORGANISM: ARTIFICIAL
<220> FEATURE:
<223> OTHER INFORMATION: SYNTHESIZED

<400> SEQUENCE: 171
tcaggagttt gggagattct cccagctttt gctgatacca                    40

<210> SEQ ID NO 172
<211> LENGTH: 40
<212> TYPE: DNA
<213> ORGANISM: ARTIFICIAL
<220> FEATURE:
<223> OTHER INFORMATION: SYNTHESIZED

<400> SEQUENCE: 172
gaatctccca aactcctgat atataataca aacaatttgc                    40

<210> SEQ ID NO 173
<211> LENGTH: 41
<212> TYPE: DNA
<213> ORGANISM: ARTIFICIAL
<220> FEATURE:
<223> OTHER INFORMATION: SYNTHESIZED

<400> SEQUENCE: 173
ccttgatggg atgcccgttt gcaaattgtt tgtattatat a                  41

<210> SEQ ID NO 174
<211> LENGTH: 40
<212> TYPE: DNA
<213> ORGANISM: ARTIFICIAL
<220> FEATURE:
<223> OTHER INFORMATION: SYNTHESIZED
```

<400> SEQUENCE: 174
aaacgggcat cccatcaagg ttcagtggca gtggatctgg                              40

<210> SEQ ID NO 175
<211> LENGTH: 39
<212> TYPE: DNA
<213> ORGANISM: ARTIFICIAL
<220> FEATURE:
<223> OTHER INFORMATION: SYNTHESIZED

<400> SEQUENCE: 175
ggtgagtgtg aaatcagtac cagatccact gccactgaa                               39

<210> SEQ ID NO 176
<211> LENGTH: 40
<212> TYPE: DNA
<213> ORGANISM: ARTIFICIAL
<220> FEATURE:
<223> OTHER INFORMATION: SYNTHESIZED

<400> SEQUENCE: 176
tactgatttc acactcacca tcagcagcct gcagcctgaa                              40

<210> SEQ ID NO 177
<211> LENGTH: 41
<212> TYPE: DNA
<213> ORGANISM: ARTIFICIAL
<220> FEATURE:
<223> OTHER INFORMATION: SYNTHESIZED

<400> SEQUENCE: 177
cagaaatatg tggcaacatc ttcaggctgc aggctgctga t                            41

<210> SEQ ID NO 178
<211> LENGTH: 39
<212> TYPE: DNA
<213> ORGANISM: ARTIFICIAL
<220> FEATURE:
<223> OTHER INFORMATION: SYNTHESIZED

<400> SEQUENCE: 178
gatgttgcca catatttctg cttgcagcat ataagtagg                               39

<210> SEQ ID NO 179
<211> LENGTH: 40
<212> TYPE: DNA
<213> ORGANISM: ARTIFICIAL
<220> FEATURE:
<223> OTHER INFORMATION: SYNTHESIZED

<400> SEQUENCE: 179
cccagttcca aacgtgcgcg gcctacttat atgctgcaag                              40

<210> SEQ ID NO 180
<211> LENGTH: 40
<212> TYPE: DNA
<213> ORGANISM: ARTIFICIAL
<220> FEATURE:
<223> OTHER INFORMATION: SYNTHESIZED

<400> SEQUENCE: 180
ccgcgcacgt ttggaactgg gaccaagctg gagctgaaac                              40

<210> SEQ ID NO 181
<211> LENGTH: 39

```
<212> TYPE: DNA
<213> ORGANISM: ARTIFICIAL
<220> FEATURE:
<223> OTHER INFORMATION: SYNTHESIZED

<400> SEQUENCE: 181
aaagtttaaa ttctactcac gtttcagctc cagcttggt                              39

<210> SEQ ID NO 182
<211> LENGTH: 38
<212> TYPE: DNA
<213> ORGANISM: ARTIFICIAL
<220> FEATURE:
<223> OTHER INFORMATION: SYNTHESIZED

<400> SEQUENCE: 182
gtgagtagaa tttaaacttt gcttcgtcga ctggatcc                               38

<210> SEQ ID NO 183
<211> LENGTH: 18
<212> TYPE: DNA
<213> ORGANISM: ARTIFICIAL
<220> FEATURE:
<223> OTHER INFORMATION: SYNTHESIZED

<400> SEQUENCE: 183
ggatccagtc gacgaagc                                                    18

<210> SEQ ID NO 184
<211> LENGTH: 38
<212> TYPE: DNA
<213> ORGANISM: ARTIFICIAL
<220> FEATURE:
<223> OTHER INFORMATION: SYNTHESIZED

<400> SEQUENCE: 184
gcatgttgac cctgacgcaa gcttgccgcc accatggg                              38

<210> SEQ ID NO 185
<211> LENGTH: 27
<212> TYPE: DNA
<213> ORGANISM: ARTIFICIAL
<220> FEATURE:
<223> OTHER INFORMATION: SYNTHESIZED

<400> SEQUENCE: 185
ggagtggaca cctgtggaga gaaaggc                                          27

<210> SEQ ID NO 186
<211> LENGTH: 36
<212> TYPE: DNA
<213> ORGANISM: ARTIFICIAL
<220> FEATURE:
<223> OTHER INFORMATION: SYNTHESIZED

<400> SEQUENCE: 186
gcgatagctg gactgaatgg atccagtcga cgaagc                                36

<210> SEQ ID NO 187
<211> LENGTH: 38
<212> TYPE: DNA
<213> ORGANISM: ARTIFICIAL
<220> FEATURE:
<223> OTHER INFORMATION: SYNTHESIZED

<400> SEQUENCE: 187
```

-continued gcatgttgac cctgacgcaa gcttgccgcc accatggg   38

<210> SEQ ID NO 188
<211> LENGTH: 30
<212> TYPE: DNA
<213> ORGANISM: ARTIFICIAL
<220> FEATURE:
<223> OTHER INFORMATION: SYNTHESIZED

<400> SEQUENCE: 188
ccactccgag gtgcaactgt tggaatctgg   30

<210> SEQ ID NO 189
<211> LENGTH: 30
<212> TYPE: DNA
<213> ORGANISM: ARTIFICIAL
<220> FEATURE:
<223> OTHER INFORMATION: SYNTHESIZED

<400> SEQUENCE: 189
ccagattcca acagttgcac ctcggagtgg   30

<210> SEQ ID NO 190
<211> LENGTH: 30
<212> TYPE: DNA
<213> ORGANISM: ARTIFICIAL
<220> FEATURE:
<223> OTHER INFORMATION: SYNTHESIZED

<400> SEQUENCE: 190
agccgggggg ttctctgaga ctctcctgtg   30

<210> SEQ ID NO 191
<211> LENGTH: 30
<212> TYPE: DNA
<213> ORGANISM: ARTIFICIAL
<220> FEATURE:
<223> OTHER INFORMATION: SYNTHESIZED

<400> SEQUENCE: 191
cacaggagag tctcagagaa cccccggct   30

<210> SEQ ID NO 192
<211> LENGTH: 35
<212> TYPE: DNA
<213> ORGANISM: ARTIFICIAL
<220> FEATURE:
<223> OTHER INFORMATION: SYNTHESIZED

<400> SEQUENCE: 192
agggaaggga cttgagtggg tgggttttat tagag   35

<210> SEQ ID NO 193
<211> LENGTH: 35
<212> TYPE: DNA
<213> ORGANISM: ARTIFICIAL
<220> FEATURE:
<223> OTHER INFORMATION: SYNTHESIZED

<400> SEQUENCE: 193
cgggaaagca cctgagtgga ttggttttat tagag   35

<210> SEQ ID NO 194
<211> LENGTH: 43
<212> TYPE: DNA
<213> ORGANISM: ARTIFICIAL

```
<220> FEATURE:
<223> OTHER INFORMATION: SYNTHESIZED

<400> SEQUENCE: 194
ccactcaagt cccttccctg gagcctggcg gacccagttc atg                    43

<210> SEQ ID NO 195
<211> LENGTH: 35
<212> TYPE: DNA
<213> ORGANISM: ARTIFICIAL
<220> FEATURE:
<223> OTHER INFORMATION: SYNTHESIZED

<400> SEQUENCE: 195
ccactcaggt gctttcccgg gaggctggcg aatcc                             35

<210> SEQ ID NO 196
<211> LENGTH: 48
<212> TYPE: DNA
<213> ORGANISM: ARTIFICIAL
<220> FEATURE:
<223> OTHER INFORMATION: SYNTHESIZED

<400> SEQUENCE: 196
tcttcaaatg aactccctaa gagctgagga cactgccgtt tactactg               48

<210> SEQ ID NO 197
<211> LENGTH: 46
<212> TYPE: DNA
<213> ORGANISM: ARTIFICIAL
<220> FEATURE:
<223> OTHER INFORMATION: SYNTHESIZED

<400> SEQUENCE: 197
agggagttca tttgaagata gagggtgttt ttggaattat ctctgg                 46

<210> SEQ ID NO 198
<211> LENGTH: 35
<212> TYPE: DNA
<213> ORGANISM: ARTIFICIAL
<220> FEATURE:
<223> OTHER INFORMATION: SYNTHESIZED

<400> SEQUENCE: 198
tggggccaag gaacactggt caccgtctcc tcagg                             35

<210> SEQ ID NO 199
<211> LENGTH: 31
<212> TYPE: DNA
<213> ORGANISM: ARTIFICIAL
<220> FEATURE:
<223> OTHER INFORMATION: SYNTHESIZED

<400> SEQUENCE: 199
ggagactgtg accagtgttc cttggcccca g                                 31

<210> SEQ ID NO 200
<211> LENGTH: 33
<212> TYPE: DNA
<213> ORGANISM: ARTIFICIAL
<220> FEATURE:
<223> OTHER INFORMATION: SYNTHESIZED

<400> SEQUENCE: 200
tccgaggtga aactgcagga atctggagga ggc                               33
```

<210> SEQ ID NO 201
<211> LENGTH: 30
<212> TYPE: DNA
<213> ORGANISM: ARTIFICIAL
<220> FEATURE:
<223> OTHER INFORMATION: SYNTHESIZED

<400> SEQUENCE: 201
ccagattcct gcagtttcac ctcggagtgg                              30

<210> SEQ ID NO 202
<211> LENGTH: 35
<212> TYPE: DNA
<213> ORGANISM: ARTIFICIAL
<220> FEATURE:
<223> OTHER INFORMATION: SYNTHESIZED

<400> SEQUENCE: 202
gggggttcta tgagaatctc ctgttcaggt tctgg                        35

<210> SEQ ID NO 203
<211> LENGTH: 35
<212> TYPE: DNA
<213> ORGANISM: ARTIFICIAL
<220> FEATURE:
<223> OTHER INFORMATION: SYNTHESIZED

<400> SEQUENCE: 203
gaacctgaac aggagattct catagaaccc cccgg                        35

<210> SEQ ID NO 204
<211> LENGTH: 35
<212> TYPE: DNA
<213> ORGANISM: ARTIFICIAL
<220> FEATURE:
<223> OTHER INFORMATION: SYNTHESIZED

<400> SEQUENCE: 204
cgggaaagga cctgagtgga ttggttttat tagag                        35

<210> SEQ ID NO 205
<211> LENGTH: 35
<212> TYPE: DNA
<213> ORGANISM: ARTIFICIAL
<220> FEATURE:
<223> OTHER INFORMATION: SYNTHESIZED

<400> SEQUENCE: 205
ccaatccact caggtccttt cccgggaggc tggcg                        35

<210> SEQ ID NO 206
<211> LENGTH: 41
<212> TYPE: DNA
<213> ORGANISM: ARTIFICIAL
<220> FEATURE:
<223> OTHER INFORMATION: SYNTHESIZED

<400> SEQUENCE: 206
gctaacaccc taagagctga ggacactgcc gtttactact g                 41

<210> SEQ ID NO 207
<211> LENGTH: 39
<212> TYPE: DNA
<213> ORGANISM: ARTIFICIAL
<220> FEATURE:
<223> OTHER INFORMATION: SYNTHESIZED

```
<400> SEQUENCE: 207
ctcttagggt gttagcttga agatggaggg tgttttggg                          39

<210> SEQ ID NO 208
<211> LENGTH: 35
<212> TYPE: DNA
<213> ORGANISM: ARTIFICIAL
<220> FEATURE:
<223> OTHER INFORMATION: SYNTHESIZED

<400> SEQUENCE: 208
tggggccaag gaactaccgt caccgtctcc tcagg                              35

<210> SEQ ID NO 209
<211> LENGTH: 31
<212> TYPE: DNA
<213> ORGANISM: ARTIFICIAL
<220> FEATURE:
<223> OTHER INFORMATION: SYNTHESIZED

<400> SEQUENCE: 209
ggagacggtg acggtagttc cttggcccca g                                  31

<210> SEQ ID NO 210
<211> LENGTH: 36
<212> TYPE: DNA
<213> ORGANISM: ARTIFICIAL
<220> FEATURE:
<223> OTHER INFORMATION: SYNTHESIZED

<400> SEQUENCE: 210
gataatgcca aaaactccct ctatcttcaa atgaac                             36

<210> SEQ ID NO 211
<211> LENGTH: 35
<212> TYPE: DNA
<213> ORGANISM: ARTIFICIAL
<220> FEATURE:
<223> OTHER INFORMATION: SYNTHESIZED

<400> SEQUENCE: 211
atagagggag ttttttggcat tatctctgga gatgg                             35

<210> SEQ ID NO 212
<211> LENGTH: 35
<212> TYPE: DNA
<213> ORGANISM: ARTIFICIAL
<220> FEATURE:
<223> OTHER INFORMATION: SYNTHESIZED

<400> SEQUENCE: 212
cgggaaagca cctgagtggc tgggttttat tagag                              35

<210> SEQ ID NO 213
<211> LENGTH: 36
<212> TYPE: DNA
<213> ORGANISM: ARTIFICIAL
<220> FEATURE:
<223> OTHER INFORMATION: SYNTHESIZED

<400> SEQUENCE: 213
gcgatagctg gactgaatgg atcctataaa tctctg                             36

<210> SEQ ID NO 214
```

```
<211> LENGTH: 38
<212> TYPE: DNA
<213> ORGANISM: ARTIFICIAL
<220> FEATURE:
<223> OTHER INFORMATION: SYNTHESIZED

<400> SEQUENCE: 214
gcatgttgac cctgacgcaa gcttgccgcc accatggg                              38

<210> SEQ ID NO 215
<211> LENGTH: 32
<212> TYPE: DNA
<213> ORGANISM: ARTIFICIAL
<220> FEATURE:
<223> OTHER INFORMATION: SYNTHESIZED

<400> SEQUENCE: 215
atgacccagt ctccctcatc cctgtctgca tc                                   32

<210> SEQ ID NO 216
<211> LENGTH: 35
<212> TYPE: DNA
<213> ORGANISM: ARTIFICIAL
<220> FEATURE:
<223> OTHER INFORMATION: SYNTHESIZED

<400> SEQUENCE: 216
gagggagact gggtcatctg gatgtcggag tggac                                35

<210> SEQ ID NO 217
<211> LENGTH: 34
<212> TYPE: DNA
<213> ORGANISM: ARTIFICIAL
<220> FEATURE:
<223> OTHER INFORMATION: SYNTHESIZED

<400> SEQUENCE: 217
cagagtcact atcacctgca aagcaagtca gaat                                 34

<210> SEQ ID NO 218
<211> LENGTH: 34
<212> TYPE: DNA
<213> ORGANISM: ARTIFICIAL
<220> FEATURE:
<223> OTHER INFORMATION: SYNTHESIZED

<400> SEQUENCE: 218
cagagtcact atcacctgca gagcaagtca gaat                                 34

<210> SEQ ID NO 219
<211> LENGTH: 35
<212> TYPE: DNA
<213> ORGANISM: ARTIFICIAL
<220> FEATURE:
<223> OTHER INFORMATION: SYNTHESIZED

<400> SEQUENCE: 219
attctgactt gctttgcagg tgatagtgac tctgt                                35

<210> SEQ ID NO 220
<211> LENGTH: 35
<212> TYPE: DNA
<213> ORGANISM: ARTIFICIAL
<220> FEATURE:
<223> OTHER INFORMATION: SYNTHESIZED

<400> SEQUENCE: 220
```
attctgactt gctctgcagg tgatagtgac tctgt 35

<210> SEQ ID NO 221
<211> LENGTH: 35
<212> TYPE: DNA
<213> ORGANISM: ARTIFICIAL
<220> FEATURE:
<223> OTHER INFORMATION: SYNTHESIZED

<400> SEQUENCE: 221
cccggaaaag ctcccaaact cctgatatat aatac 35

<210> SEQ ID NO 222
<211> LENGTH: 35
<212> TYPE: DNA
<213> ORGANISM: ARTIFICIAL
<220> FEATURE:
<223> OTHER INFORMATION: SYNTHESIZED

<400> SEQUENCE: 222
cccggaaaat ctcccaaact cctgatatat aatac 35

<210> SEQ ID NO 223
<211> LENGTH: 35
<212> TYPE: DNA
<213> ORGANISM: ARTIFICIAL
<220> FEATURE:
<223> OTHER INFORMATION: SYNTHESIZED

<400> SEQUENCE: 223
cccggaaaag ctcccaaatc cctgatatat aatac 35

<210> SEQ ID NO 224
<211> LENGTH: 32
<212> TYPE: DNA
<213> ORGANISM: ARTIFICIAL
<220> FEATURE:
<223> OTHER INFORMATION: SYNTHESIZED

<400> SEQUENCE: 224
tttgggagct tttccgggct ttgctgata cc 32

<210> SEQ ID NO 225
<211> LENGTH: 32
<212> TYPE: DNA
<213> ORGANISM: ARTIFICIAL
<220> FEATURE:
<223> OTHER INFORMATION: SYNTHESIZED

<400> SEQUENCE: 225
tttgggagat tttccgggct ttgctgata cc 32

<210> SEQ ID NO 226
<211> LENGTH: 27
<212> TYPE: DNA
<213> ORGANISM: ARTIFICIAL
<220> FEATURE:
<223> OTHER INFORMATION: SYNTHESIZED

<400> SEQUENCE: 226
cgtcccatca aggttcagtg gcagtgg 27

<210> SEQ ID NO 227
<211> LENGTH: 31
<212> TYPE: DNA

```
<213> ORGANISM: ARTIFICIAL
<220> FEATURE:
<223> OTHER INFORMATION: SYNTHESIZED

<400> SEQUENCE: 227
gccactgaac cttgatggga cgcccgtttg c                                    31

<210> SEQ ID NO 228
<211> LENGTH: 35
<212> TYPE: DNA
<213> ORGANISM: ARTIFICIAL
<220> FEATURE:
<223> OTHER INFORMATION: SYNTHESIZED

<400> SEQUENCE: 228
cactgaacct tgatgggacg ccagattgca aattg                                35

<210> SEQ ID NO 229
<211> LENGTH: 35
<212> TYPE: DNA
<213> ORGANISM: ARTIFICIAL
<220> FEATURE:
<223> OTHER INFORMATION: SYNTHESIZED

<400> SEQUENCE: 229
gcctgaagat attgccacat attactgctt gcagc                                35

<210> SEQ ID NO 230
<211> LENGTH: 35
<212> TYPE: DNA
<213> ORGANISM: ARTIFICIAL
<220> FEATURE:
<223> OTHER INFORMATION: SYNTHESIZED

<400> SEQUENCE: 230
tgcaagcagt aatatgtggc aatatcttca ggctg                                35

<210> SEQ ID NO 231
<211> LENGTH: 36
<212> TYPE: DNA
<213> ORGANISM: ARTIFICIAL
<220> FEATURE:
<223> OTHER INFORMATION: SYNTHESIZED

<400> SEQUENCE: 231
gcgatagctg gactgaatgg atccagtcga cgaagc                               36
```

MODIFIED ANTI-CD52 ANTIBODY

This application claims priority to U.S. provisional application 60/516,210, filed Nov. 1, 2003, the entire contents of which are hereby incorporated by reference.

FIELD OF THE INVENTION

The present invention relates to polypeptides to be administered, especially to humans and in particular for therapeutic use. The polypeptides are modified polypeptides, whereby the modification results in a reduced number of potential T-cell epitopes that provides a reduced propensity for the polypeptide to elicit an immune response upon administration to a human subject. The invention in particular relates to the modification of antibodies reactive to the CD52 human leukocyte antigen to provide anti-CD52 antibodies that have a reduced number of potential T-cell epitopes, but retain the ability to bind to CD52.

BACKGROUND OF THE INVENTION

There are many instances whereby the efficacy of a therapeutic protein is limited by an unwanted immune reaction to the therapeutic protein. Several mouse monoclonal antibodies have shown promise as therapies in a number of human disease settings but in certain cases have failed due to the induction of significant degrees of a human anti-murine antibody (HAMA) response [Schroff et al. (1985) Cancer Res. 45: 879-885; Shawler et al. (1985) J. Immunol. 135: 1530-1535]. For monoclonal antibodies, a number of techniques have been developed in attempt to reduce the HAMA response [WOA8909622; EPA0239400; EPA0438310; WOA9106667; EPA0699755]. These recombinant DNA approaches have generally reduced the mouse genetic information in the final antibody construct whilst increasing the human genetic information in the final construct. Notwithstanding, the resultant "humanised" antibodies have, in several cases, still elicited an immune response in patients [Issacs J. D. (1990) Sem. Immunol. 2: 449, 456; Rebello et al. (1999) Transplantation 68: 1417-1420].

Antibodies are not the only class of polypeptide molecule administered as a therapeutic agent against which an immune response may be mounted. Even proteins of human origin and with the same amino acid sequences as occur within humans can still induce an immune response in humans. Notable examples include therapeutic use of granulocyte-macrophage colony stimulating factor [Wadhwa et al., (1999) Clin. Cancer Res. 5: 1353-1361] and interferon α2 [Russo et al. (1996) Bri. J. Haem. 94: 300-305; Stein et al. (1988) New Engl. J. Med. 318: 1409-1413] amongst others.

Key to the induction of an immune response is the presence within the protein of peptides that can stimulate the activity of T-cells via presentation on MHC class II molecules, so-called "T-cell epitopes." Such T-cell epitopes are commonly defined as any amino acid residue sequence with the ability to bind to MHC Class II molecules. Implicitly, a "T-cell epitope" means an epitope which when bound to MHC molecules can be recognized by a T-cell receptor (TCR), and which can, at least in principle, cause the activation of these T-cells by engaging a TCR to promote a T-cell response.

MHC Class II molecules are a group of highly polymorphic proteins which play a central role in helper T-cell selection and activation. The human leukocyte antigen group DR (HLA-DR) are the predominant isotype of this group of proteins however, isotypes HLA-DQ and HLA-DP perform similar functions. In the human population, individuals bear two to four DR alleles, two DQ and two DP alleles. The structure of a number of DR molecules has been solved and these appear as an open-ended peptide binding groove with a number of hydrophobic pockets which engage hydrophobic residues (pocket residues) of the peptide [Brown et al., Nature (1993) 364: 33; Stern et al. (1994) Nature 368: 215]. Polymorphism identifying the different allotypes of class II molecule contributes to a wide diversity of different binding surfaces for peptides within the peptide binding grove and at the population level ensures maximal flexibility with regard to the ability to recognise foreign proteins and mount an immune response to pathogenic organisms.

An immune response to a therapeutic protein proceeds via the MHC class II peptide presentation pathway. Here exogenous proteins are engulfed and processed for presentation in association with MHC class II molecules of the DR, DQ or DP type. MHC Class II molecules are expressed by professional antigen presenting cells (APCs), such as macrophages and dendritic cells amongst others. Engagement of a MHC class II peptide complex by a cognate T-cell receptor on the surface of the T-cell, together with the cross-binding of certain other co-receptors such as the CD4 molecule, can induce an activated state within the T-cell. Activation leads to the release of cytokines further activating other lymphocytes such as B cells to produce antibodies or activating T killer cells as a full cellular immune response.

T-cell epitope identification is the first step to epitope elimination as recognised in WO98/52976 and WO00/34317. In these teachings, predicted T-cell epitopes are removed by the use of judicious amino acid substitutions within the protein of interest. Besides computational techniques, there are in vitro methods for measuring the ability of synthetic peptides to bind MHC class II molecules. An exemplary method uses B-cell lines of defined MHC allotype as a source of MHC class II binding surface and may be applied to MHC class II ligand identification [Marshall et al. (1994) J. Immunol. 152:4946-4956; O'Sullivan et al. (1990) J. Immunol. 145: 1799-1808; Robadey et al. (1997) J. Immunol 159: 3238-3246]. However, such techniques are not adapted for the screening multiple potential epitopes to a wide diversity of MHC allotypes, nor can they confirm the ability of a binding peptide to function as a T-cell epitope.

Recently, techniques exploiting soluble complexes of recombinant MHC molecules in combination with synthetic peptides have come into use [Kern et al. (1998) Nature Medicine 4:975-978; Kwok et al. (2001) TRENDS in Immunol. 22:583-588]. These reagents and procedures are used to identify the presence of T-cell clones from peripheral blood samples from human or experimental animal subjects that are able to bind particular MHC-peptide complexes and are not adapted for the screening multiple potential epitopes to a wide diversity of MHC allotypes.

As depicted above and as consequence thereof, it would be desirable to identify and to remove or at least to reduce potential T-cell epitopes from a given in principal therapeutically valuable but originally immunogenic peptide, polypeptide or protein. One of these therapeutically valuable molecules is a monoclonal antibody with binding specificity for the CD52 human leukocyte antigen. The preferred monoclonal antibody of the present invention is a modified form of the rat antibody termed "CAMPATH". It is an objective of the invention to provide for modified forms of the CAMPATH antibody with one or more potential T-cell epitopes removed.

The CD52 molecule has a molecule weight of 21-28 kDa, and the mature protein comprises a 12 amino acid peptide with a N-linked oligosaccharide being attached to the membrane by its glycophosphatidylinositol anchor. The antigen is present on at least 95% of human peripheral blood lymphocytes and also cells of the monocyte/macrophage series and in addition spermatozoa. It is not present on erythrocytes, platelets, tissue dendritic cells or bone marrow stem cells (Hale et al. (1990) *Tissue Antigens* 35:873; Buggins et al. (2002) *Blood*, 100:1715).

The first CD52 antibodies were raised in a rat immunized with human lymphocytes in an attempt to obtain antibodies that activated complement for use to deplete donor marrow of T-cells prior to transplantation [Hale et al. (1983) *Blood* 62: 873-882]. The majority of lytic antibodies were anti-CD52 IgM antibodies. Although useful ex vivo, CD52 IgM (CAMPATH-1M) mediated complement activation was not effective in eliminating T-cells in vivo. CAMPATH-1G, a rat IgG2b monoclonal antibody, obtained by isotype switching from an IgG2a antibody clone, binds human Fc receptors, mediates cell death antibody-mediated cellular toxicity (ADCCD) and is effective in eliminating cells in vivo [Friend et al. (1991) *Transplant. Proc.* 23: 2253-2254; Hale et al. (1998) *Blood* 92: 4581-4590]. However, use of CAMPATH-IG is limited by the immune response elicited in patients [Cobbold, J. S. (1990) *J. Immunol. Methods* 127: 19-24; Dyer, M. J. S. (1989) *Blood* 73: 1431-1439]. To reduce immunogenicity, a humanized IgG1 antibody, CAMPATH-1H, was engineered by cloning the Kabat hypervariable regions into a framework provided from human NEW and Rei myeloma proteins [Riechmann et al., (1988) *Nature* 332: 323-327]. Although reducing the immunogenicity compared to CAMPTH-1G, the humanized antibody still elicits immune responses in some patients. In an early report of treatment for rheumatoid arthritis, no antiglobulin response was reported in the 8 patients treated by a first course of i.v. administration, but 3 of 4 patients who received a second course of CAMPATH-1H developed antiglobulin antibodies (Issacs et al. (1992) *Lancet*, 21:1103-06). In a subsequent single-dose escalation i.v. study in rheumatoid arthritis patients, 63% of subjects developed antiglobulin responses, which were primarily anti-idiotypic responses [Weinblatt et al. (1995) *Arthritis. Rheum.* 38: 1589-1594]. Antiglobulin responses were also reported for all 10 rheumatoid arthritis patients who received escalating doses of CAMPATH-1H by subcutaneous administration (Schnitzer et al., *J. Rheumatol.* (1997) 24:1031-36).

Thus, it is desirable to provide anti-CD52 antibodies with a reduced number of potential T-cell epitopes which may result in a reduced or absent potential to induce an immune response in the human subject. Such proteins may be expected to display an increased circulation time within a human subject capable of mounting an immune response to the non-modified antibody and may be of particular benefit in chronic or recurring disease settings such as is the case for a number of indications for CAMPATH. The present invention accordingly provides for modified forms of an anti-CD52 antibody with reduced numbers of potential T-cell epitopes that are expected to display decreased immunogenicity while however, substantially retaining the beneficial therapeutic features associated with the efficacy of the parental non-modified antibody.

The invention discloses sequences identified within the variable region sequences of the heavy and light chains of an anti-CD52 antibody that are potential T cell epitopes by virtue of MHC class II binding potential.

While others have provided anti-CD52 antibody molecules including "humanised" forms [U.S. Pat. Nos. 5,846,543; 6,120,766; 6,569,430; WO0230460] none of these teachings recognise the importance of T cell epitopes to the immunogenic properties of the protein nor have been conceived to directly influence said properties in a specific and controlled way according to the scheme of the present invention.

SUMMARY AND DESCRIPTION OF THE INVENTION

Figure 1:
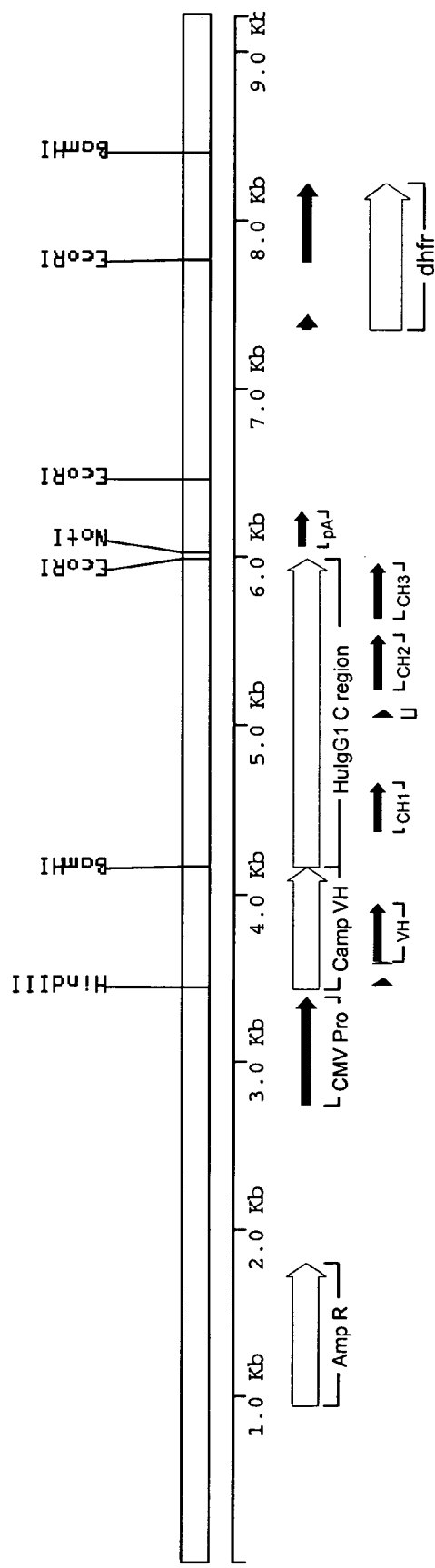
FIG. 1 depicts an exemplified vector for a modified heavy chain, "camp VH." dhfr is dihydrofolate reductase selection; CMV pro is the CMV IE promoter; pA is Poly A; and Amp R is ampicillin resistance.

The present invention provides for a modified antibody in which the immune characteristic is modified by means of reduced numbers of potential T-cell epitopes. Disclosed are sequences identified within the CAMPATH-1G variable region sequences of both the heavy chain and light chain that are potential T-cell epitopes by virtue of MHC class II binding potential. The invention discloses the major regions of the antibody V-region sequence that may be immunogenic in man and modified sequences to eliminate or reduce the potential immunogenic effectiveness of these sites.

In one aspect, the invention provides a modified antibody molecule having specificity for the CD52 antigen recognised by the rat antibody CAMPATH-1G wherein one or more amino acids in the variable region of the CAMPATH-1G antibody is substituted to reduce MHC class II recognition of peptides derived from this region. Implicit in the terms "anti-CD52 antibody" and "CAMPATH antibody," when applied to modified antibodies of the present invention, is an ability for such modified antibodies to retain an ability to bind to CD52. Embodiments of the invention encompass an anti-CD52 antibody comprising a heavy chain V-region comprising a substituted variant of SEQ ID NO: 1 with one or more of the substitutions listed in Table 1, wherein the numbering of amino acid residues relates to those of SEQ ID NO: 1, and comprising a light chain V-region comprising a substituted variant of SEQ ID NO: 2 with one or more of the substitutions listed in Table 2, wherein the numbering of amino acid residues relates to those of SEQ ID NO: 1. In some embodiments the anti-CD52 antibody heavy chain further comprise a human IgG1 constant region domain and the light chain further comprises a human kappa constant region domain.

TABLE 1

Substitutions within potential T-cell epitopes in the CAMPATH-1G variable heavy chain (SEQ ID NO: 1)

| VH Residue # | WT residue | Substitution |
|---|---|---|
| 3 | K | Q |
| 5 | L | A C B Z G H K P R S T |
| 12 | V | B E H K P Q R S T |
| 13 | Q | A F H K N P Q R S T |
| 15 | G | D H P Q R S T |
| 17 | S | G M P W |
| 18 | M | A G P L |
| 19 | R | A C F G I L M P V W Y |
| 20 | L | A C F G H I K B M Z P R S T V W Y |
| 21 | S | P |
| 23 | A | B Z G H K P R S T |
| 25 | S | F G L P W Y |
| 26 | G | B Z H K P R S T W Y |
| 31 | D | A F G I M P V W Y |

TABLE 1-continued

Substitutions within potential T-cell epitopes in the CAMPATH-1G variable heavy chain (SEQ ID NO: 1)

| VH Residue # | WT residue | Substitution |
|---|---|---|
| 33 | Y | A G M P |
| 35 | N | P |
| 36 | W | A D E G H K N P Q R S T |
| 37 | I | V |
| 38 | R | F H P Y |
| 40 | P | A |
| 41 | A | B Z H K P R S T W |
| 42 | G | I P T Y |
| 44 | A | G H N P Q S T W Y |
| 45 | P | L |
| 48 | L | V I |
| 71 | T | F L P W Y |
| 72 | I | D E H K N P Q R S T |
| 73 | S | A G P |
| 74 | R | A F G I M P W Y |
| 76 | N | A G M P W Y |
| 77 | T | A H I P S |
| 78 | Q | K |
| 79 | N | A F G I M P V W Y |
| 80 | M | A D E G H K N P Q R T S |
| 82 | Y | A D E G H K N P Q R S T |
| 84 | Q | A F G I L M P V W Y |
| 85 | M | A D E G H K N P Q R S T |
| 87 | T | S |
| 88 | L | D E G H K N P Q R S T |
| 89 | R | F P W Y |
| 90 | A | B Z H K P R S T W Y |
| 91 | E | P |
| 92 | D | A F G I L M P V W Y |
| 95 | T | V |
| 109 | D | A F G I L M P V W Y |
| 111 | W | A D E G H K N P Q R S T |
| 114 | G | H P S T |
| 115 | V | T |

TABLE 1-continued

Substitutions within potential T-cell epitopes in the CAMPATH-1G variable heavy chain (SEQ ID NO: 1)

| VH Residue # | WT residue | Substitution |
|---|---|---|
| 116 | M | L F I P T V W Y |
| 117 | V | A F G I M P W Y |

TABLE 2

Substitutions within potential T-cell epitopes in the CAMPATH-1G light chain (SEQ ID NO: 2)

| VK Residue # | WT residue | Substitution |
|---|---|---|
| 3 | K | Q |
| 10 | F | A B Z G H K P R S T |
| 15 | V | A G H P |
| 17 | D | P |
| 19 | V | P W |
| 21 | L | P I |
| 22 | N | T |
| 24 | K | R |
| 33 | L | A B Z G H K P R S T |
| 40 | L | B Z G H K P R S T |
| 42 | E | K |
| 43 | S | A |
| 46 | L | S |
| 56 | T | A F G I M P S W Y |
| 58 | I | A G M P V |
| 60 | S | A F G I M P W Y |
| 61 | R | P |
| 63 | S | F L P W Y |
| 64 | G | B Z H K P R S T |
| 78 | L | B Z G H K P R S T |
| 83 | V | A B Z G H I K P R S T |
| 87 | F | Y |

In various embodiments, more than 2 amino acid substitutions, or more than 3 amino acid substitutions, or more than 4 amino acid substitutions, or more than 5 amino acid substitutions, or more than 6 amino acid substitutions, or more than 7 amino acid, or more than 8, or more than 9, or more than 10, or more than 11 or more than 12 substitutions are made in the heavy chain and/or the light chain. In some embodiments, between 5 and 20, or between 7 and 14, amino acid substitutions are made in the heavy and/or light chain.

In some embodiments, the anti-CD52 antibody comprises a V-region heavy chain comprising a substituted variant of SEQ ID NO: 1 with one or more of the following substitutions, wherein the numbering of amino acid residues relates to those of SEQ ID NO: 1:
  substitution of Lys at amino acid residue 3 with Gln;
  Leu at amino acid residue 5 with Ala, Cys, Asn, Asp, Gln, Glu, Gly, His, Lys, Pro, Arg, Ser, or Thr;
  Met at amino acid residue 18 with Arg, Gly, Pro, Leu;
  Leu at amino acid residue 20 with Ala, Cys, Phe, Gly, His, Ile, Lys, Asn, Asp, Met, Gln, Glu, Pro, Arg, Ser, Thr, Val Trp, or Tyr;
  Ala at amino acid residue 23 with Asp, Asn, Glu, Gln, Gly, His, Lys, Pro, Arg, Ser, Thr;
  Ile at amino acid residue 37 with Val;
  Pro at amino acid residue 40 with Ala;
  Ala at amino acid residue 41 with Pro;
  Ala at amino acid residue 44 with Gly, His, Asn, Pro, Gln, Ser, Thr, Trp, Tyr;
  Pro at amino acid residue 45 with Leu;
  Leu at amino acid residue 48 with Ile or Val;
  Thr at amino acid residue 77 with Ala, His, Ile, Pro or Ser;
  Gln at amino acid residue 78 with Lys;
  Met at amino acid residue 80 with Ala, Asp, Glu, Gly, His, Lys, Asn, Pro, Gln, Arg, Thr, or Ser;
  Tyr at amino acid residue 82 with Ala, Asp, Glu, Gly, His, Lys, Asn, Pro, Gln, Arg, Ser or Thr;
  Met at amino acid residue 85 with Ala, Asp, Glu, Gly, His, Lys, Asn, Pro, Gln, Arg, Ser or Thr;
  Thr at amino acid residue 87 with Ser;
  Thr at amino acid residue 95 with Val;
  Val at amino acid residue 115 with Thr;
  Met at amino acid residue 116 with Thr, Phe, Ile, Leu, Pro, Val, Trp or Tyr;
  and comprising a V-region light chain comprising a substituted variant of SEQ ID NO: 2 with one or more of the following substitutions, wherein the numbering of amino acid residues relates to those of SEQ ID NO: 2: substitution of Lys at amino acid residue 3 with Gln
  Phe at amino acid residue 10 with Ala, Asp, Asn, Glu, Gln, Gly, His, Lys, Pro, Arg, Ser or Thr;
  Leu at amino acid residue 21 with Pro or Ile;
  Asn at amino acid residue 22 with Thr;
  Lys at amino acid residue 24 with Arg;
  Leu at amino acid residue 40 with Asp, Asn, Gln, Glu, Gly, His, Lys, Pro, Arg, Ser or Thr;
  Glu at amino acid residue 42 with Lys;
  Ser at amino acid residue 43 with Ala;
  Leu at amino acid residue 46 with Ser;
  Thr at amino acid residue 56 with Ala, Phe, Gly, Ile, Met, Pro, Ser, Trp or Tyr;
  Ile at amino acid residue 58 with Ala; Gly, Met, Pro or Val;
  Val at amino acid residue 83 with Ala, Asp, Asn, Glu, Gln, Gly, His, Ile, Lys, Pro, Arg, Ser, Thr; and
  Phe at amino acid residue 87 with Tyr.

In some embodiments of the present invention, the anti-CD52 antibody comprises a V-region heavy chain comprising a substituted variant of SEQ ID NO: 1 with one or more of the following substitutions, wherein the numbering of amino acid residues relates to those of SEQ ID NO: 1:
  substitution of Lys at amino acid residue 3 with Gln;
  Leu at amino acid residue 5 with Gln;
  Met at amino acid residue 18 with Leu;

Leu at amino acid residue 20 with Ile;
Ala at amino acid residue 23 with Ser;
Ile at amino acid residue 37 with Val;
Pro at amino acid residue 40 with Ala;
Ala at amino acid residue 41 with Pro;
Ala at amino acid residue 44 with Gly;
Pro at amino acid residue 45 with Leu;
Leu at amino acid residue 48 with Ile or Val;
Thr at position 77 with Ala or Ser;
Gln at amino acid residue 78 with Lys;
Met at amino acid position 80 with Thr, or Ser;
Tyr at amino acid residue 82 with His;
Met at amino acid residue 85 with Ala;
Thr at amino acid residue 87 with Ser;
Thr at amino acid residue 95 with Val;
Val at amino acid residue 115 with Thr;
Met at amino acid residue 116 with Leu;
and comprising a V-region light chain comprising a substituted variant of SEQ ID NO: 2 with one or more of the following substitutions, wherein the numbering of amino acid residues relates to those of SEQ ID NO: 2:
substitution of Lys at amino acid residue 3 with Gln;
Phe at amino acid residue 10 with Ser;
Leu at amino acid residue 21 with Ile;
Asn at amino acid residue 22 with Thr;
Lys at amino acid residue 24 with Arg;
Leu at amino acid residue 40 with Pro;
Glu at amino acid residue 42 with Lys;
Ser at amino acid residue 43 with Ala;
Leu at amino acid residue 46 with Ser;
Thr at amino acid residue 56 with Ser;
Ile at amino acid residue 58 with Val;
Val at amino acid residue 83 with Ile;
Phe at amino acid residue 87 with Tyr.

In a further aspect of the invention, there are provided variant monoclonal antibodies with a reduced number of potential T-cell epitopes, said variants comprising a combination of heavy chain V-region comprising a sequence selected from SEQ ID NO: 3 through SEQ ID NO: 7 or SEQ ID NO: 13 through SEQ ID NO: 40 and light chain V-regions comprising a sequence selected from SEQ ID NO: 8 through SEQ ID NO: 12 or SEQ ID NO: 41 through SEQ ID NO: 70. In some preferred embodiments, the invention provides for variant monoclonal antibodies with a reduced number of potential T-cell epitopes, said variants comprising a combination of heavy chain V-region comprising a sequence selected from SEQ ID NO: 3 through SEQ ID NO:7 and light chain V-region comprising a sequence selected from SEQ ID NO: 8 through SEQ ID NO: 12. In some embodiments the anti-CD52 antibody further comprises a human IgG1 constant region domain and a human kappa constant region domain. In further embodiments, the anti-CD52 antibody comprising a human IgG1 constant region and a human kappa constant region comprises a heavy chain V-region comprising SEQ ID NO: 4 and a light chain V-region comprising SEQ ID NO: 12, or a heavy chain V-region comprising SEQ ID NO: 7 and a light chain V-region comprising SEQ ID NO: 12, or a heavy chain V-region comprising SEQ ID NO: 7 and a light chain V-region comprising SEQ ID NO: 10, or a heavy chain V-region comprising SEQ ID NO: 3 and a light chain V-region comprising SEQ ID NO: 10, or a heavy chain V-region comprising SEQ ID NO: 6 and a light chain V-region comprising SEQ ID NO: 10.

The present invention also encompasses an accordingly specified molecule, wherein the alteration of the amino acid residues is substitution, addition or deletion of originally present amino acid(s) residue(s) by other amino acid residue(s) at specific position(s); an accordingly specified molecule, wherein, if necessary, additionally further alteration usually by substitution, addition or deletion of specific amino acid(s) is conducted to restore a biological activity of said molecule; an accordingly specified molecule wherein alteration is conducted at one or more residues from any or all of the string of contiguous residues of sequences (A)-(S) as below wherein said sequences are derived from the CAMPATH-1G antibody V-region sequence domains of the molecule and where using single letter code;

A. = KLLESGGGLVQPG (amino acids 3-15 of SEQ ID NO:1);

B. = GLVQPGGSMRLSC (amino acids 10-22 of SEQ ID NO:1);

C. = GSMRLSCAGSGFT (amino acids 16-28 of SEQ ID NO:1);

D. = DFYMNWIRQPAGK (amino acids 31-43 of SEQ ID NO:1);

E. = MNWIRQPAGKAPE (amino acids 34-46 of SEQ ID NO:1);

F. = FTISRDNTQNMLY (amino acids 70-82 of SEQ ID NO:1);

G. = QNMLYLQMNTLRA (amino acids 78-90 of SEQ ID NO:1);

H. = MLYLQMNTLRAED (amino acids 80-92 of SEQ ID NO:1);

I. = LQMNTLRAEDTAT (amino acids 83-95 of SEQ ID NO:1);

J. = NTLRAEDTATYYC (amino acids 86-98 of SEQ ID NO:1);

K. = DYWGQGVMVTVSS (amino acids 109-121 of SEQ ID NO:1);

L. = PSFLSASVGDRVT (amino acids 8-20 of SEQ ID NO:2);

M. = ASVGDRVTLNCKA (amino acids 13-25 of SEQ ID NO:2);

N. = DRVTLNCKASQNI (amino acids 17-29 of SEQ ID NO:2);

O. = KYLNWYQQKLGES (amino acids 31-43 of SEQ ID NO:2);

P. = QKLGESPKLLIYN (amino acids 38-50 of SEQ ID NO:2);

Q. = TGIPSRFSGSGSG (amino acids 56-68 of SEQ ID NO:2);

R. = SSLQPEDVATYFC (amino acids 76-88 of SEQ ID NO:2);

S. = EDVATYFCLQHIS (amino acids 81-93 of SEQ ID NO:2).

One aspect of the present invention is a pharmaceutical composition comprising a modified CAMPATH-1G molecule modified so as to reduce the number of potential T-cell epitopes and having the ability to bind to CD52, wherein said composition comprises a pharmaceutically acceptable carrier.

Figure 2:
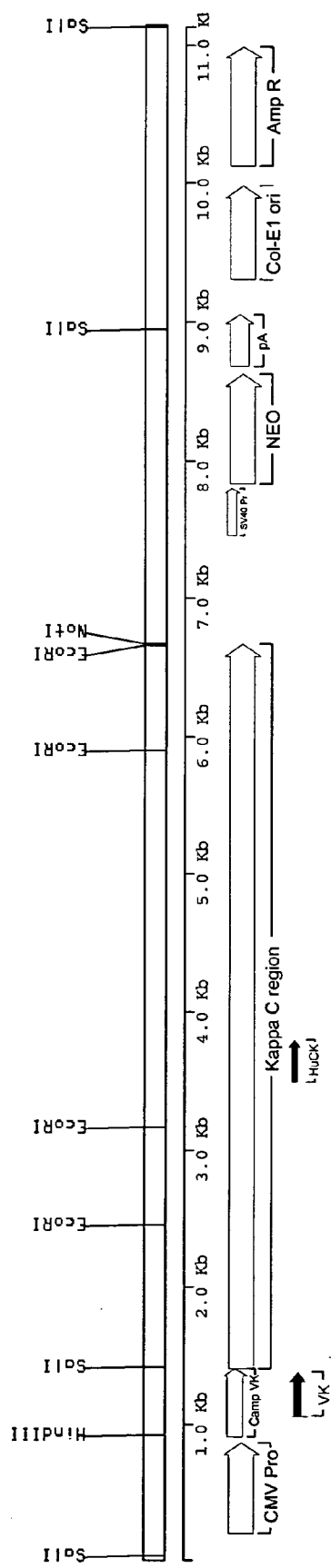
FIG. 2 depicts an exemplified vector for a modified light chain, "camp VL". Neo is neomycin (G148) selection; CMV pro is the CMV IE promoter; pA is Poly A; and Amp R is ampicillin resistance
Figure 3:
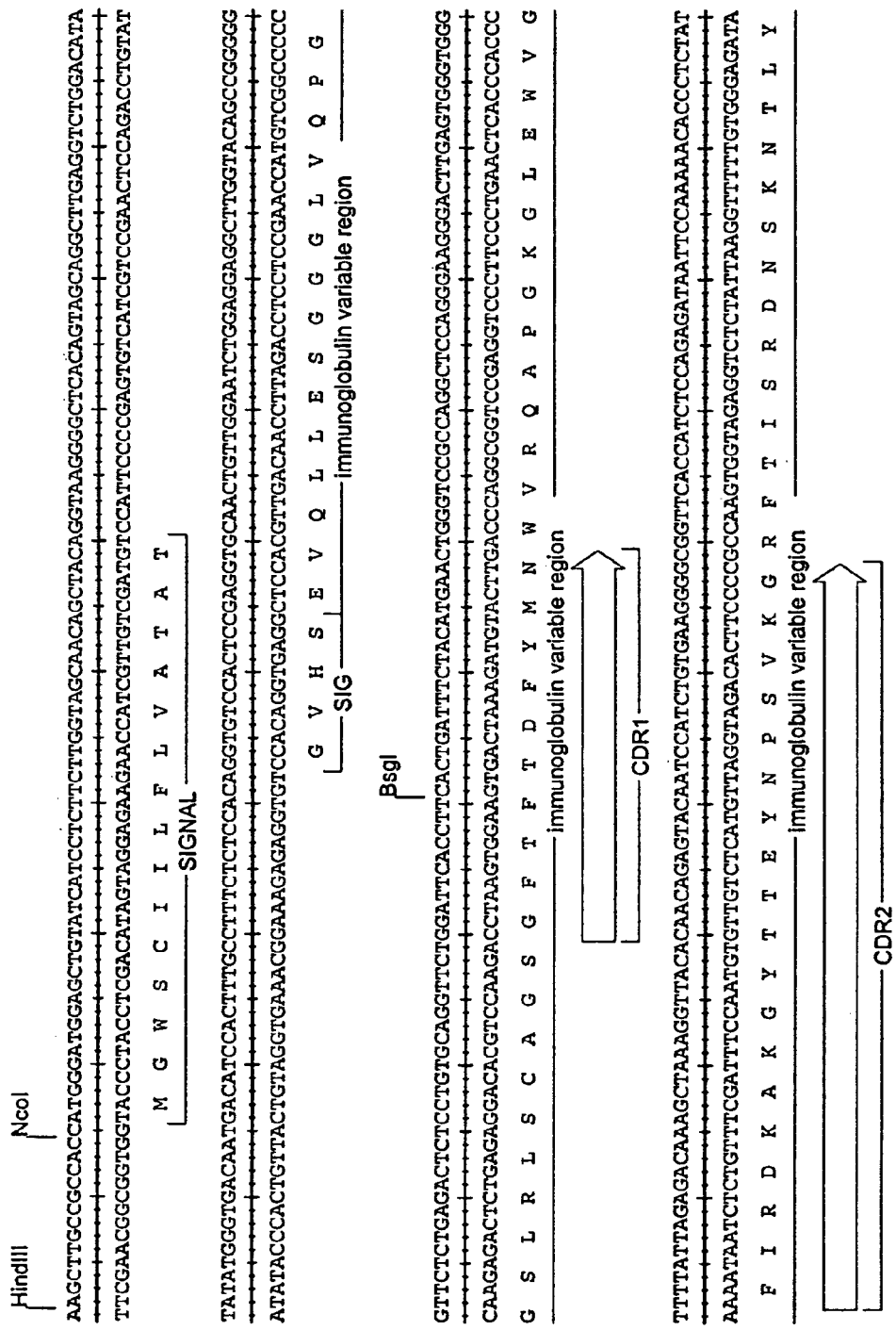
FIG. 3 depicts the DNA and amino acid sequences of modified heavy chain variable region DIVHv1 (SEQ ID NO:71 and SEQ ID NO:3, respectively).
Figure 3:
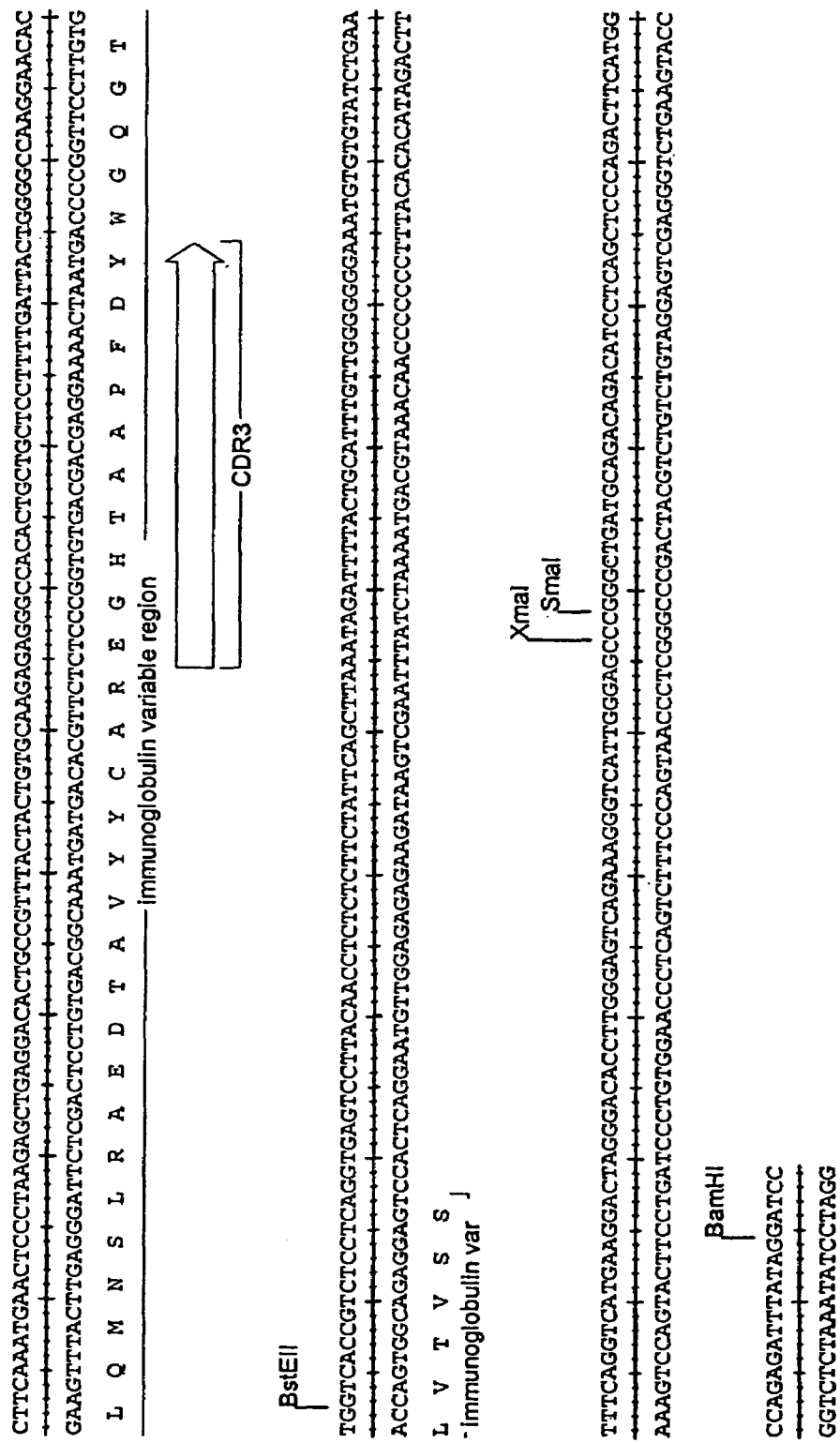
Figure 4:
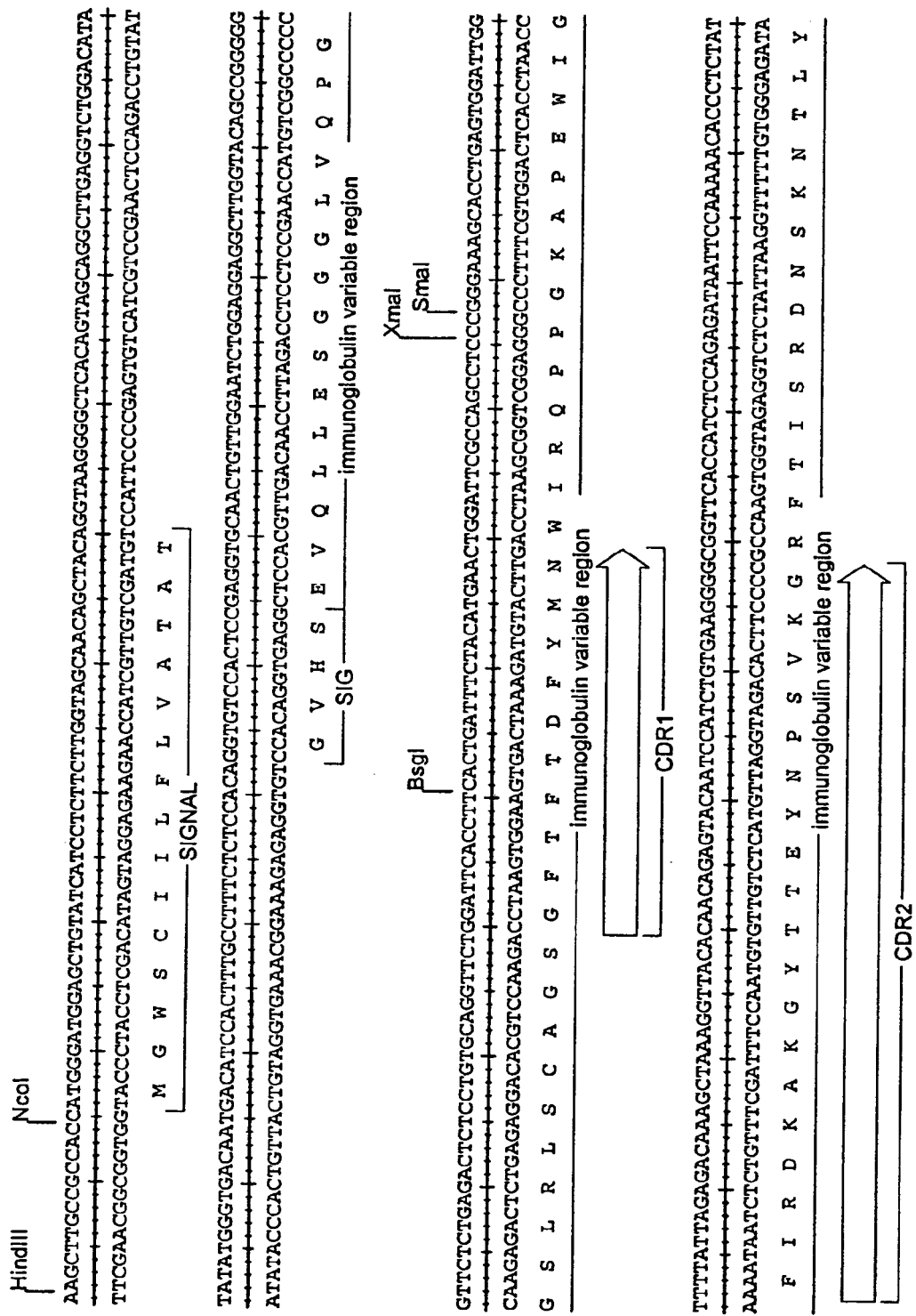
FIG. 4 depicts the DNA and amino acid sequences of modified heavy chain variable region DIVHv2 (SEQ ID NO:72 and SEQ ID NO:4, respectively).
Figure 4:
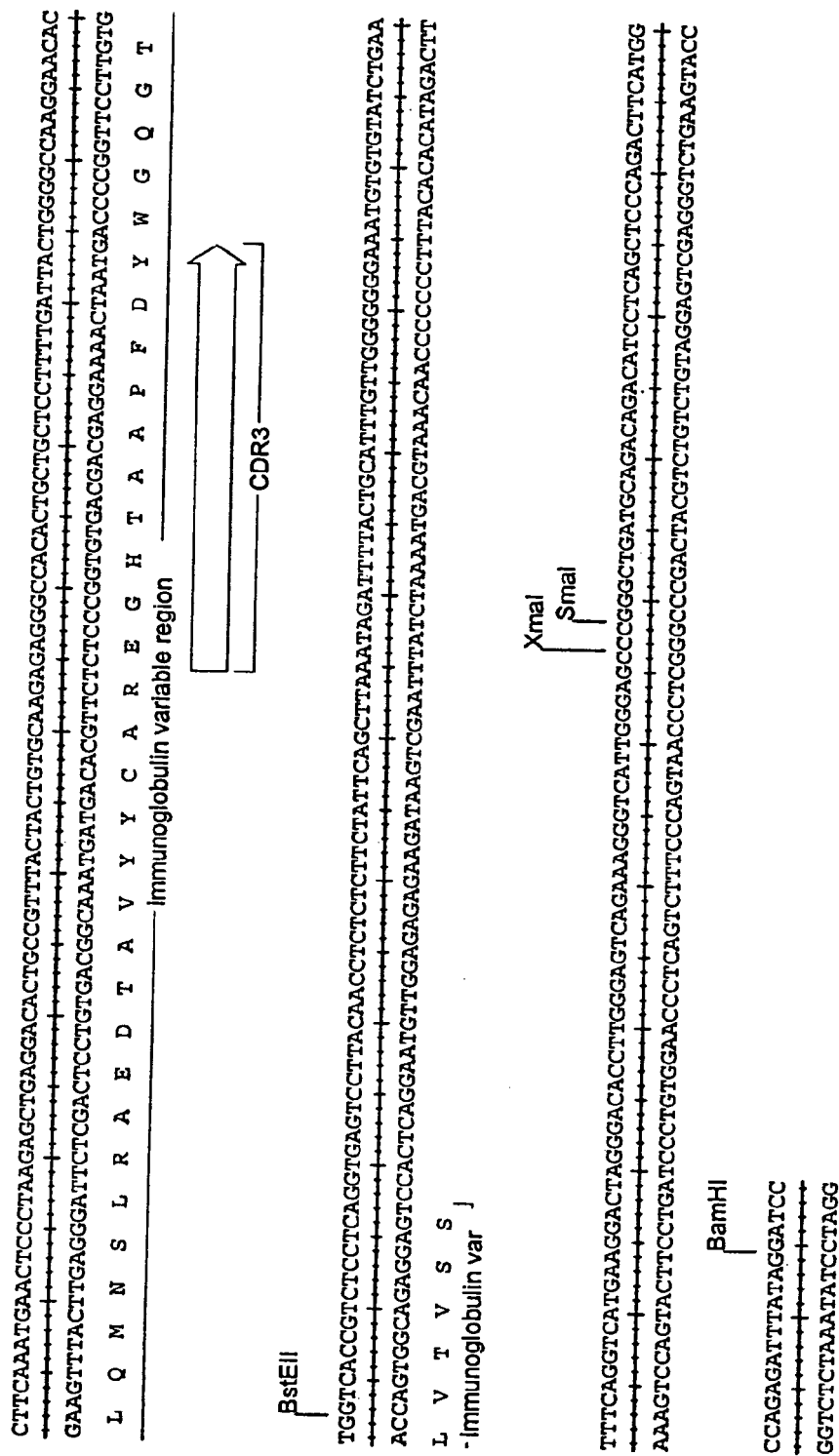
Figure 5:
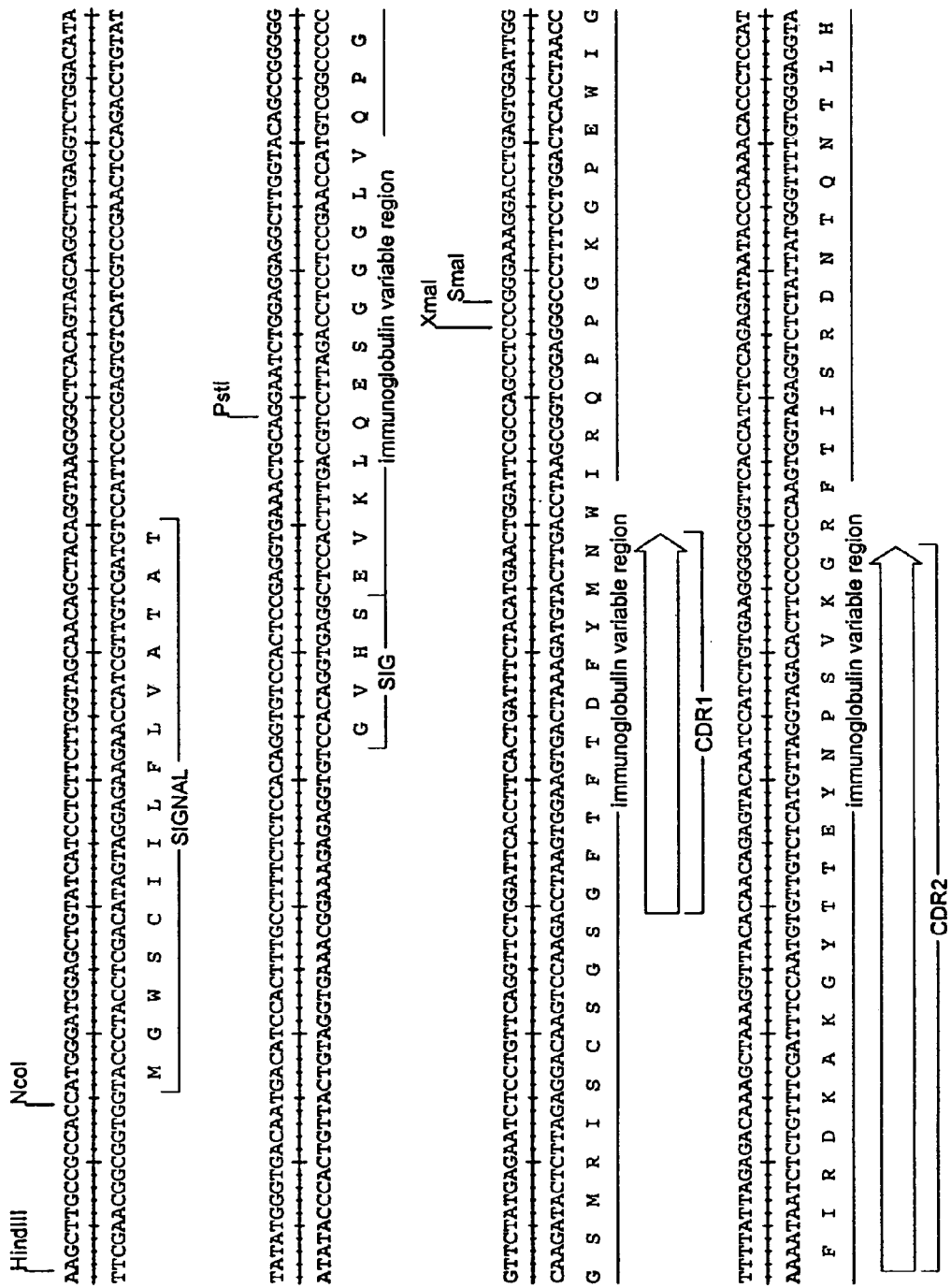
FIG. 5 depicts the DNA and amino acid sequences of modified heavy chain variable region DIVHv3 (SEQ ID NO:73 and SEQ ID NO:5, respectively).
Figure 5:
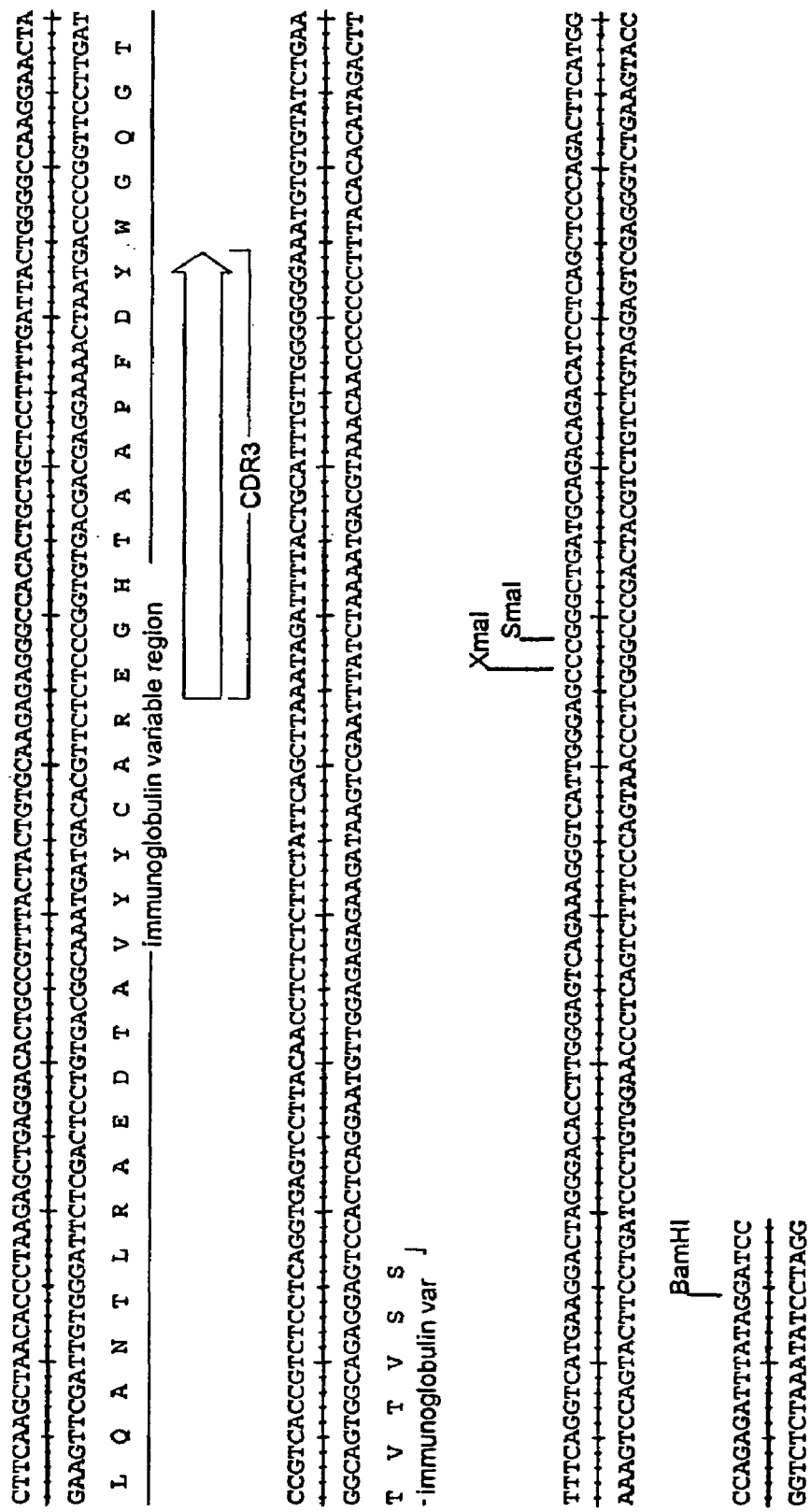
Figure 6:
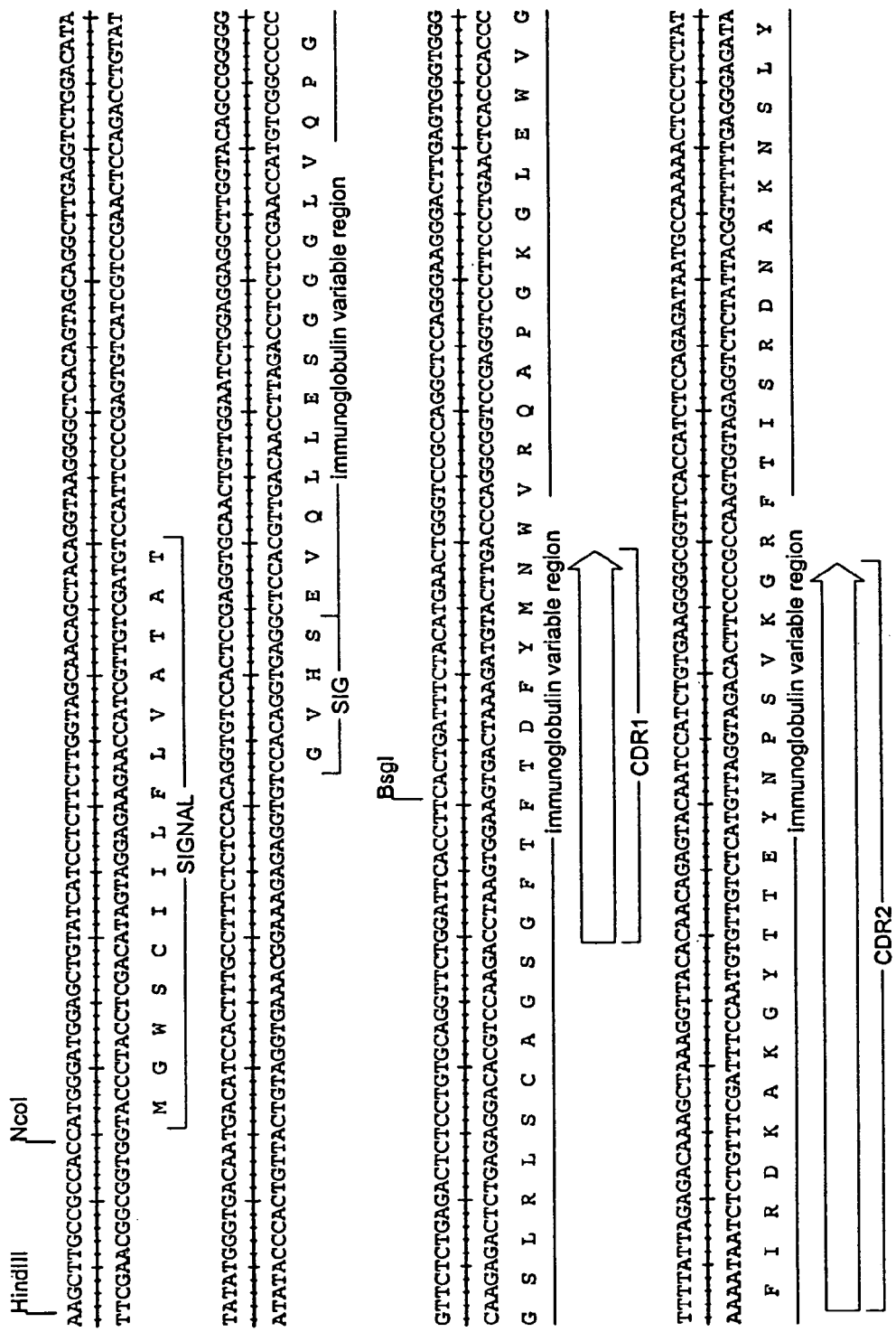
FIG. 6 depicts the DNA and amino acid sequences of modified heavy chain variable region DIVHv4 (SEQ ID NO:74 and SEQ ID NO:6, respectively).
Figure 6:
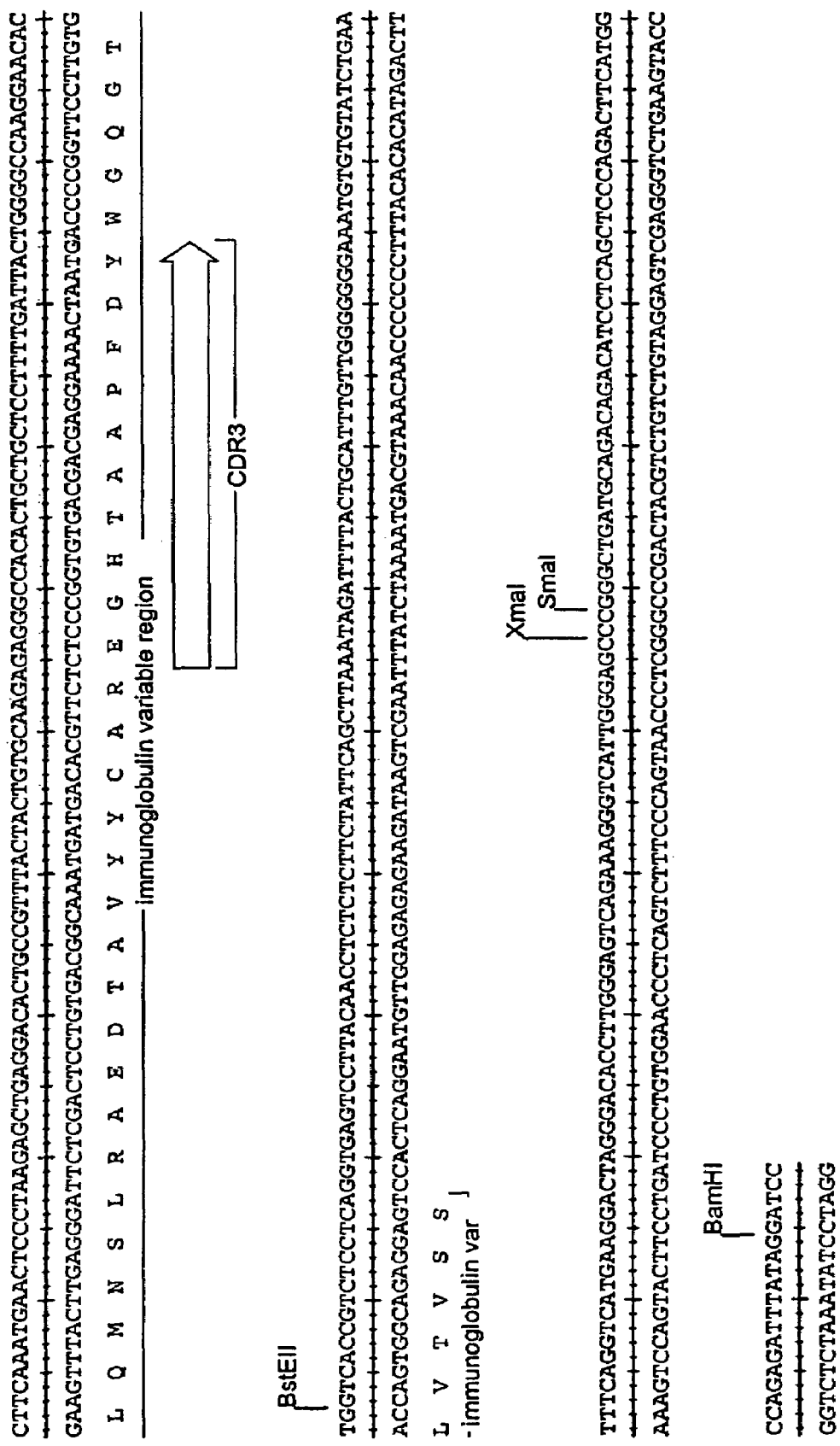
Figure 7:
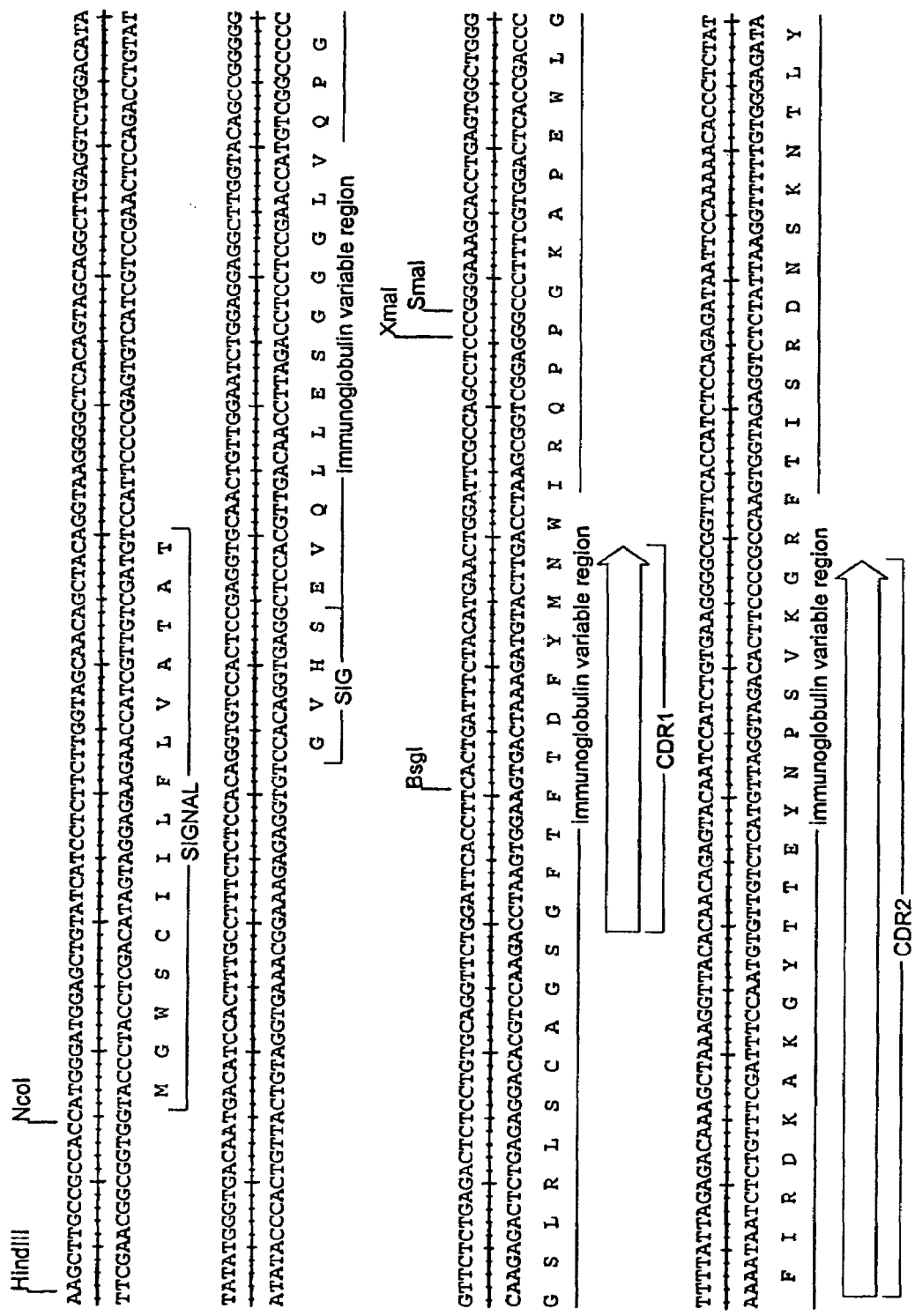
FIG. 7 depicts the DNA and amino acid sequences of modified heavy chain variable region DIVHv5 (SEQ ID NO:75 and SEQ ID NO:7, respectively).
Figure 7:
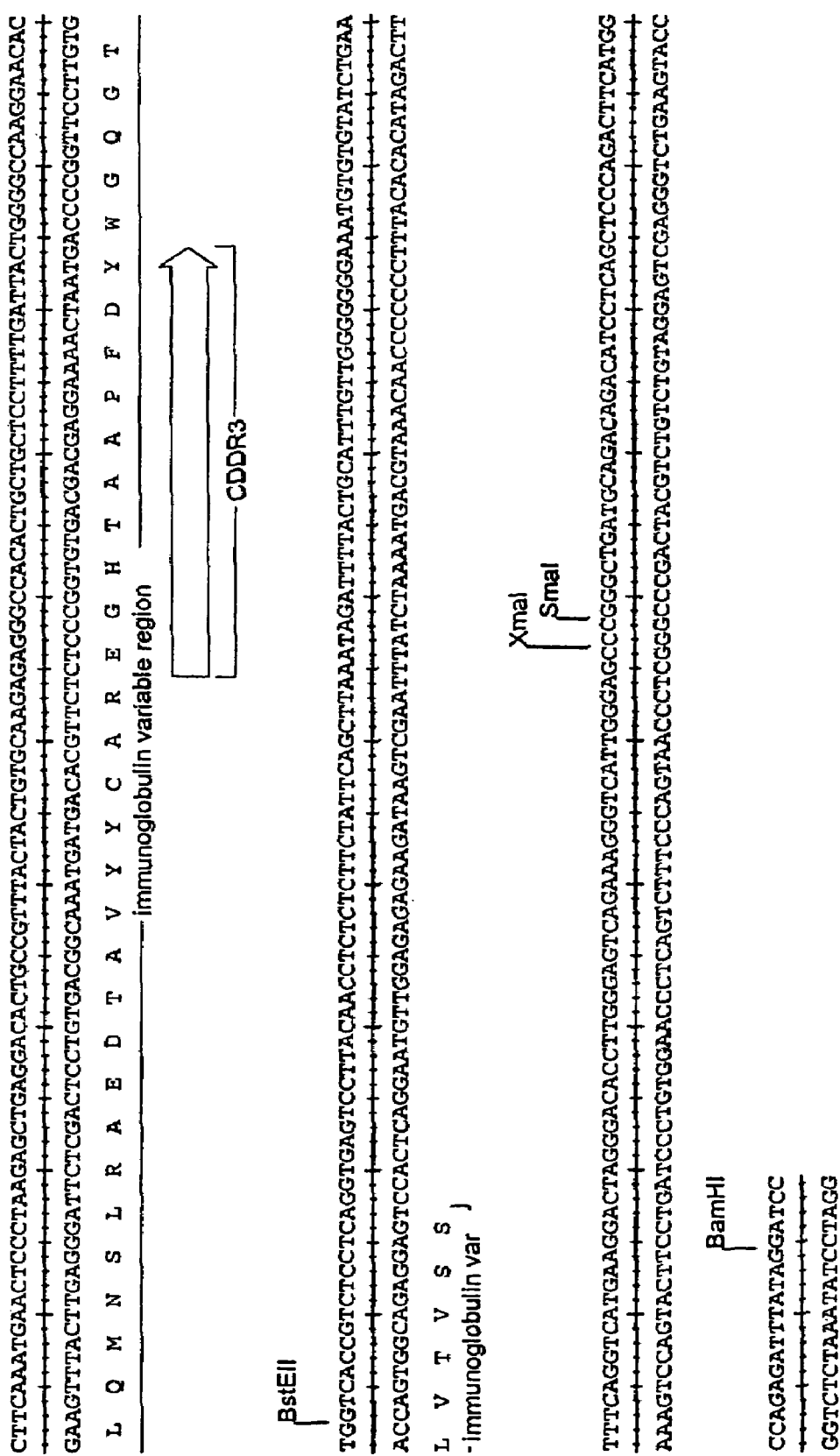
Figure 8:
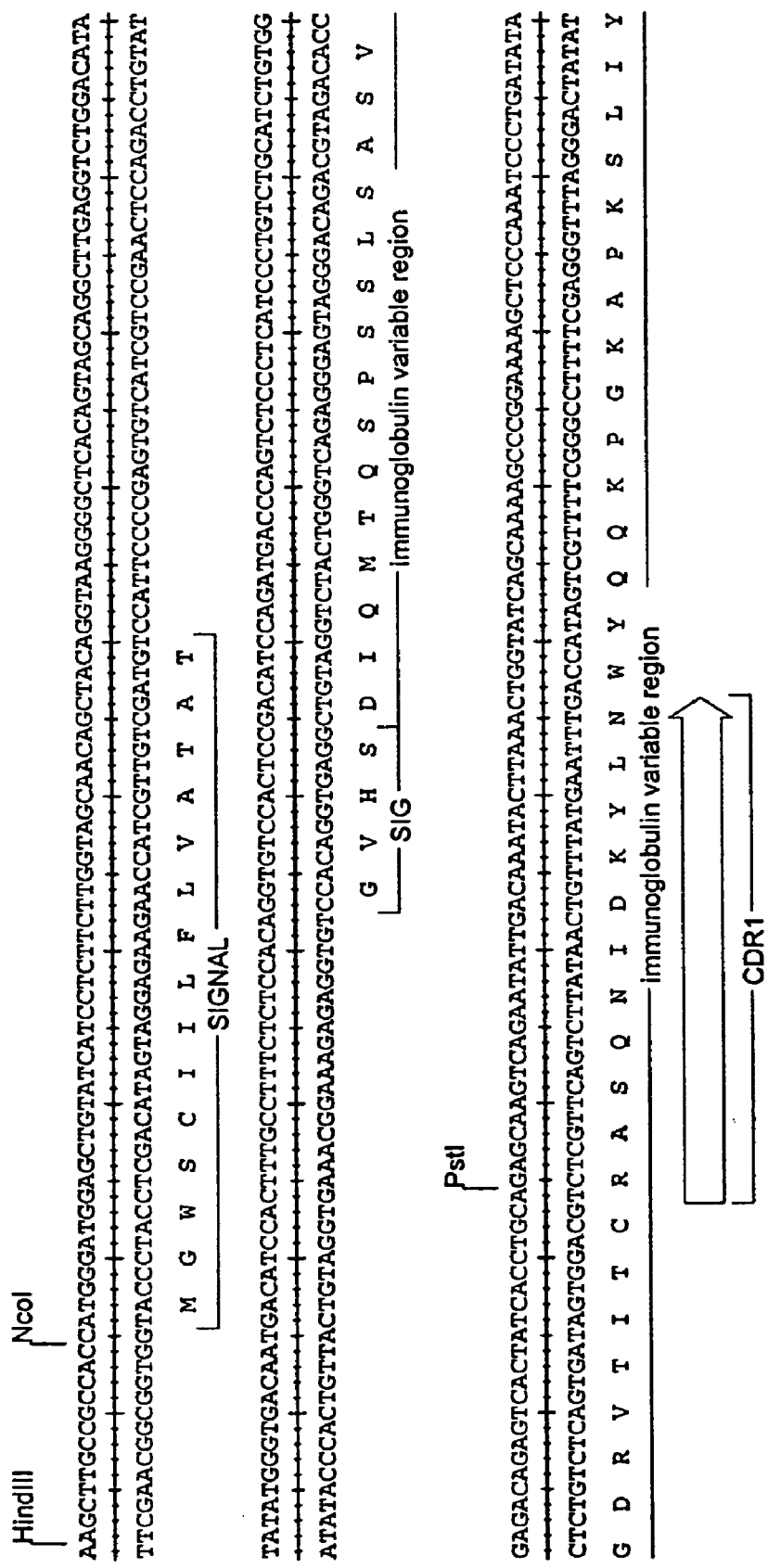
FIG. 8 depicts the DNA and amino acid sequences of modified light chain variable region DIVKv1 (SEQ ID NO:76 and SEQ ID NO:8, respectively).
Figure 8:
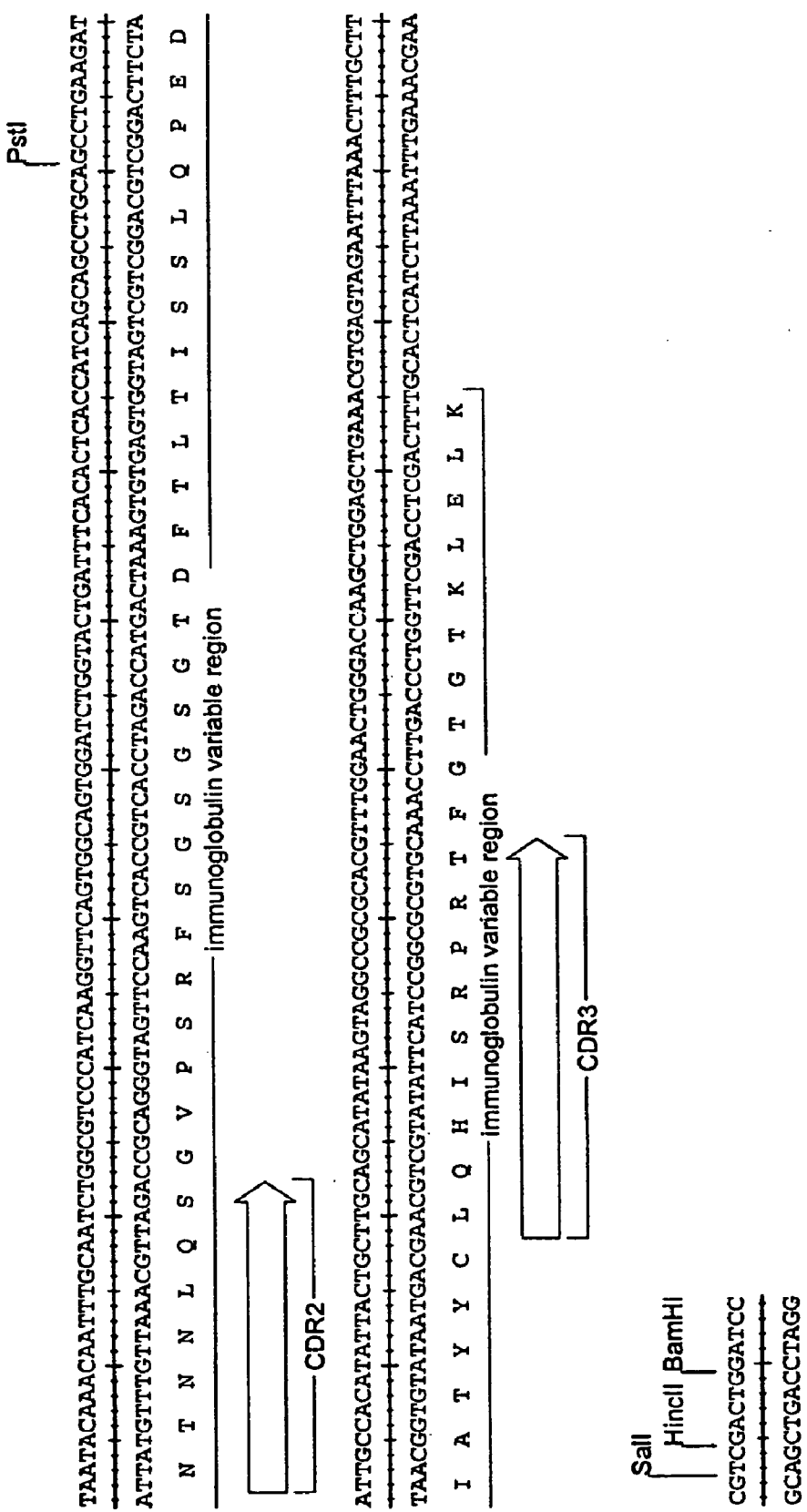
Figure 9:
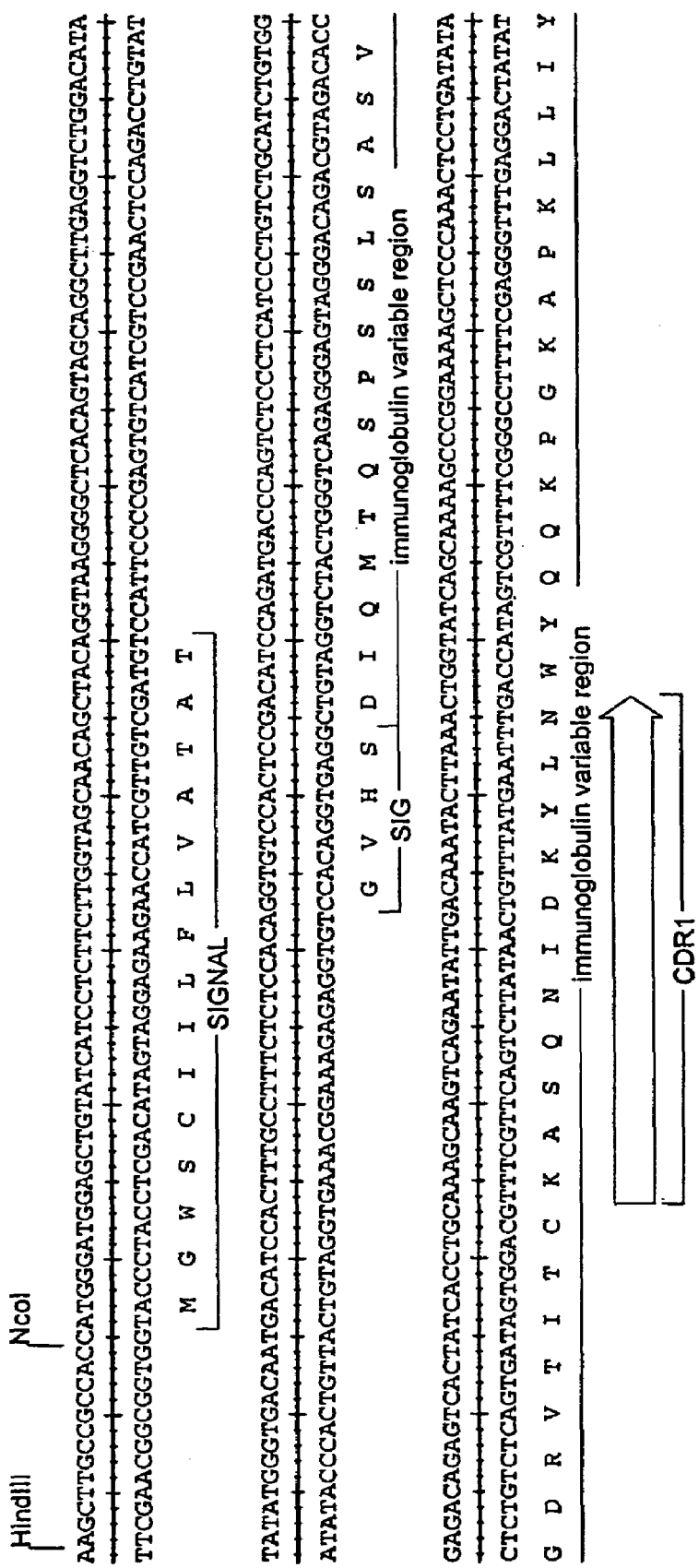
FIG. 9 depicts the DNA and amino acid sequences of modified light chain variable region DIVKv2 (SEQ ID NO:77 and SEQ ID NO:9, respectively).
Figure 9:
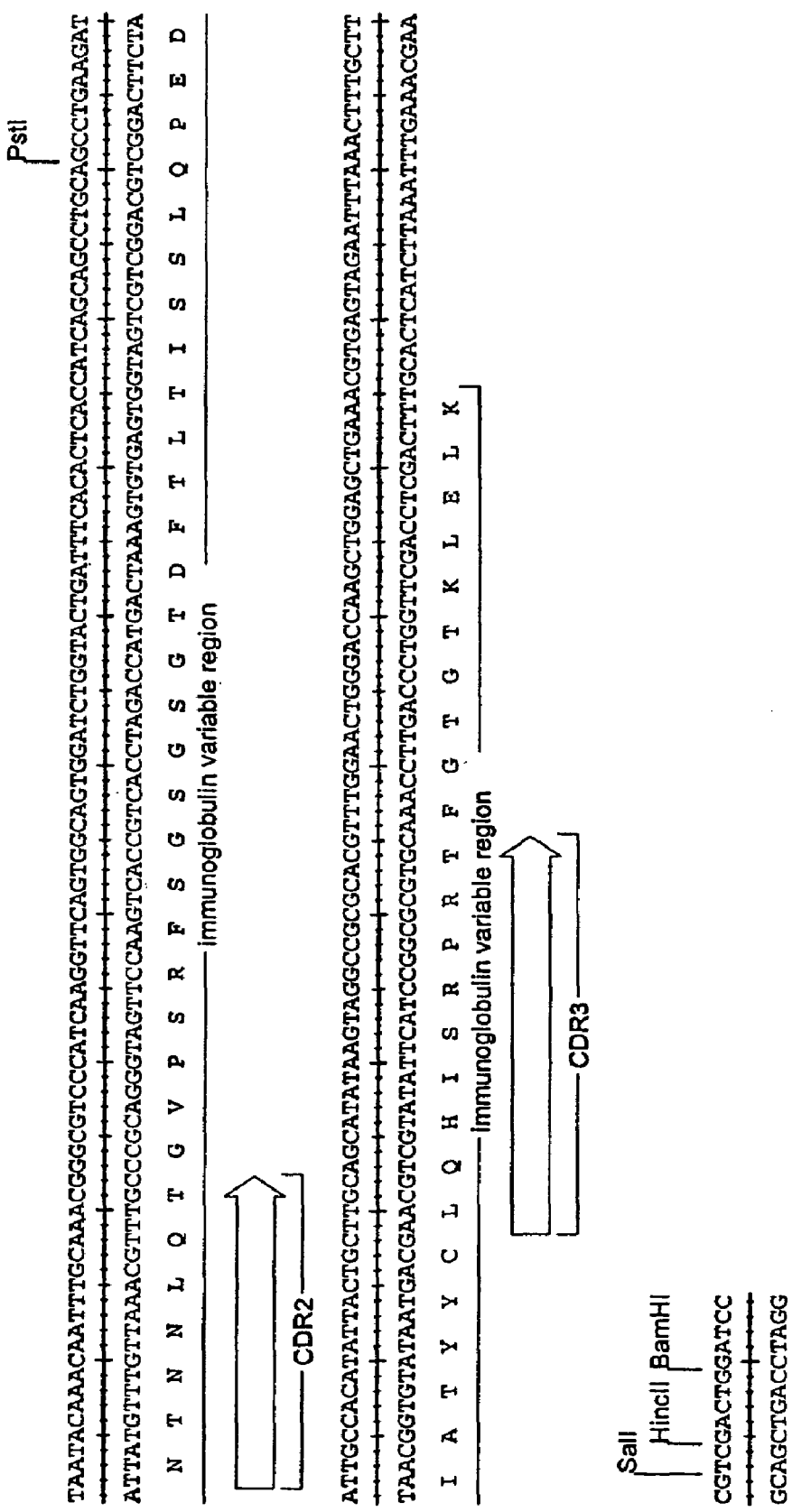
Figure 10:
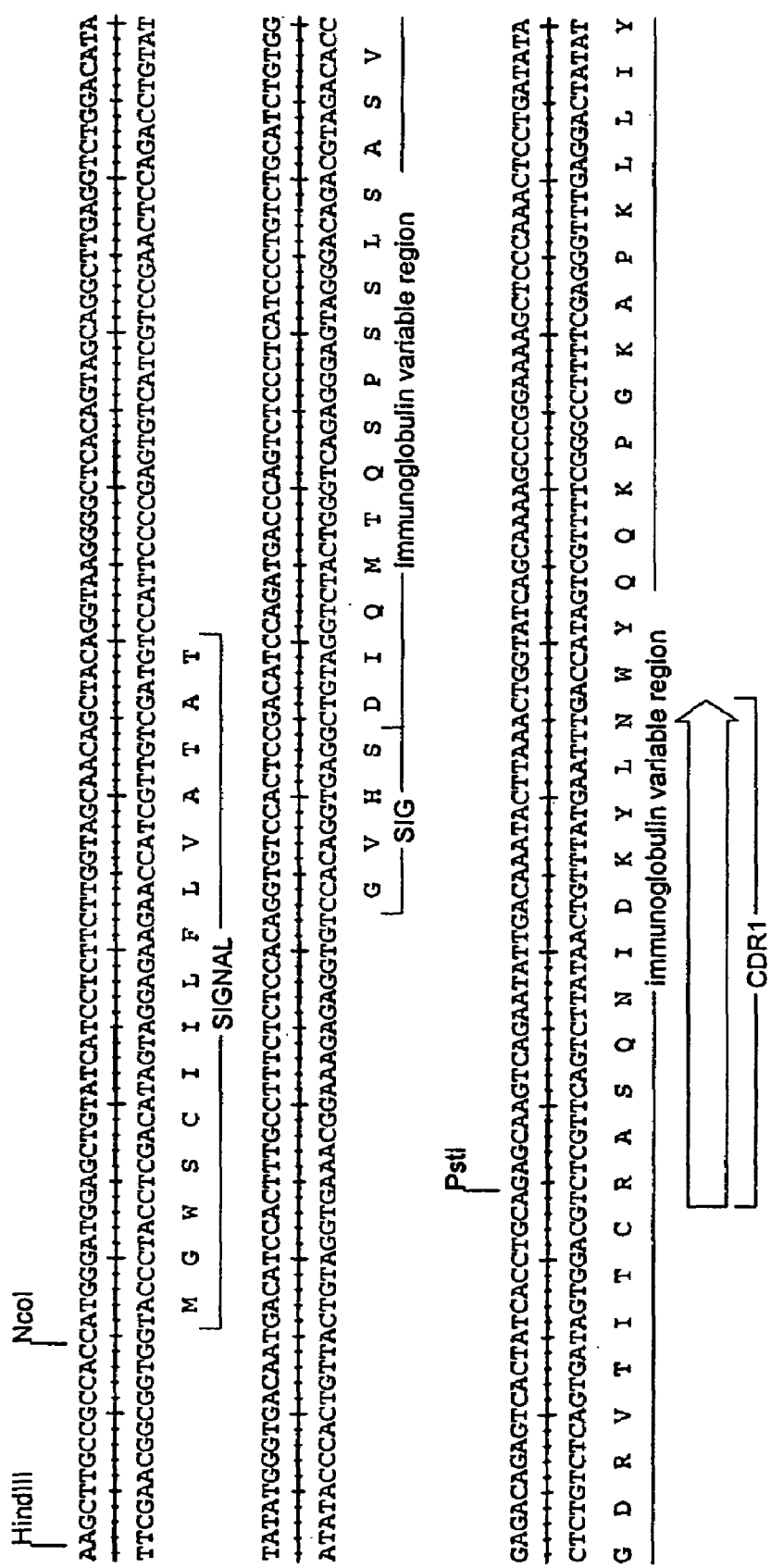
FIG. 10 depicts the DNA and amino acid sequences of modified light chain variable region DIVKv3 (SEQ ID NO:78 and SEQ ID NO:10, respectively).
Figure 10:
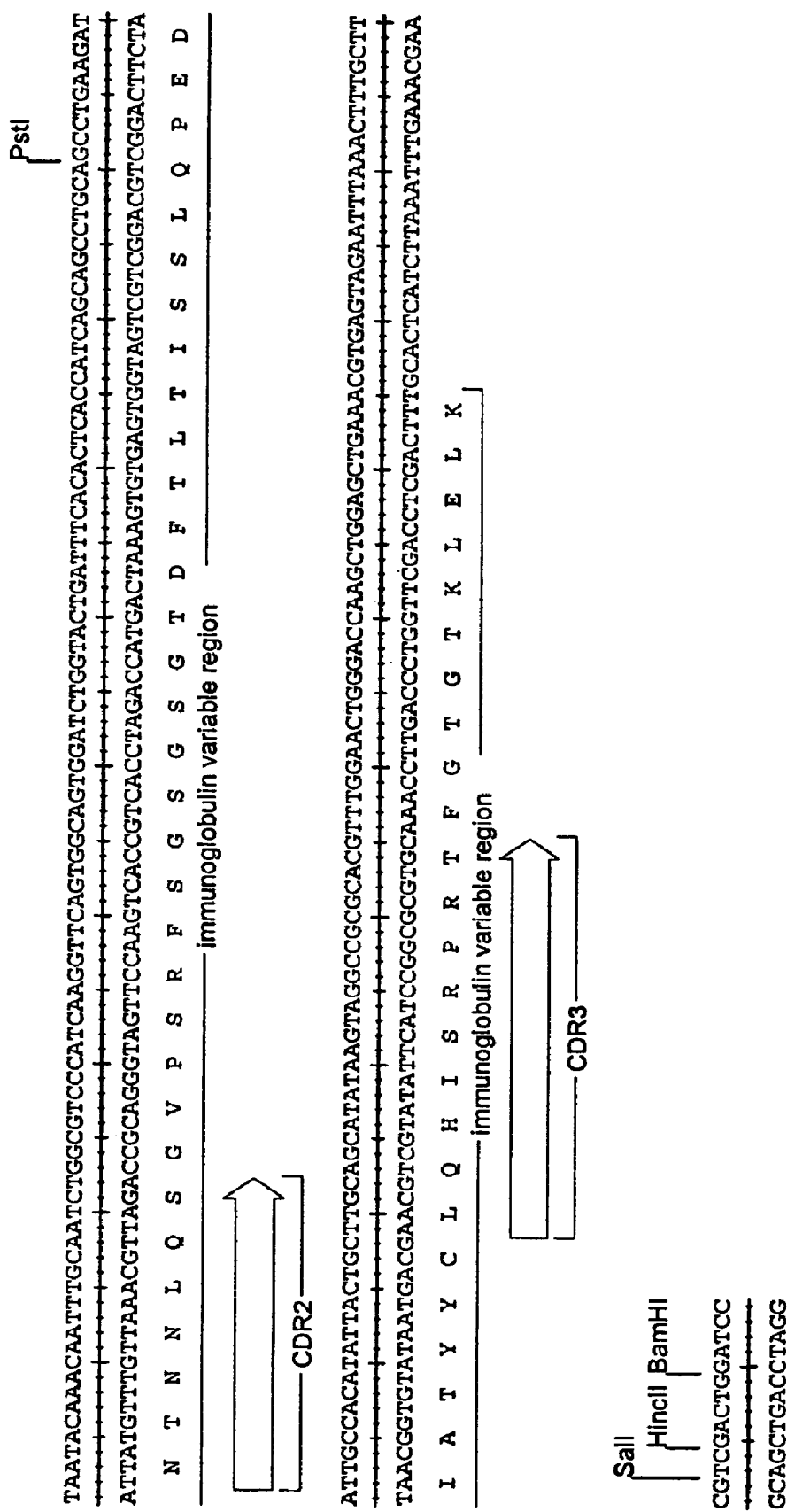
Figure 11:
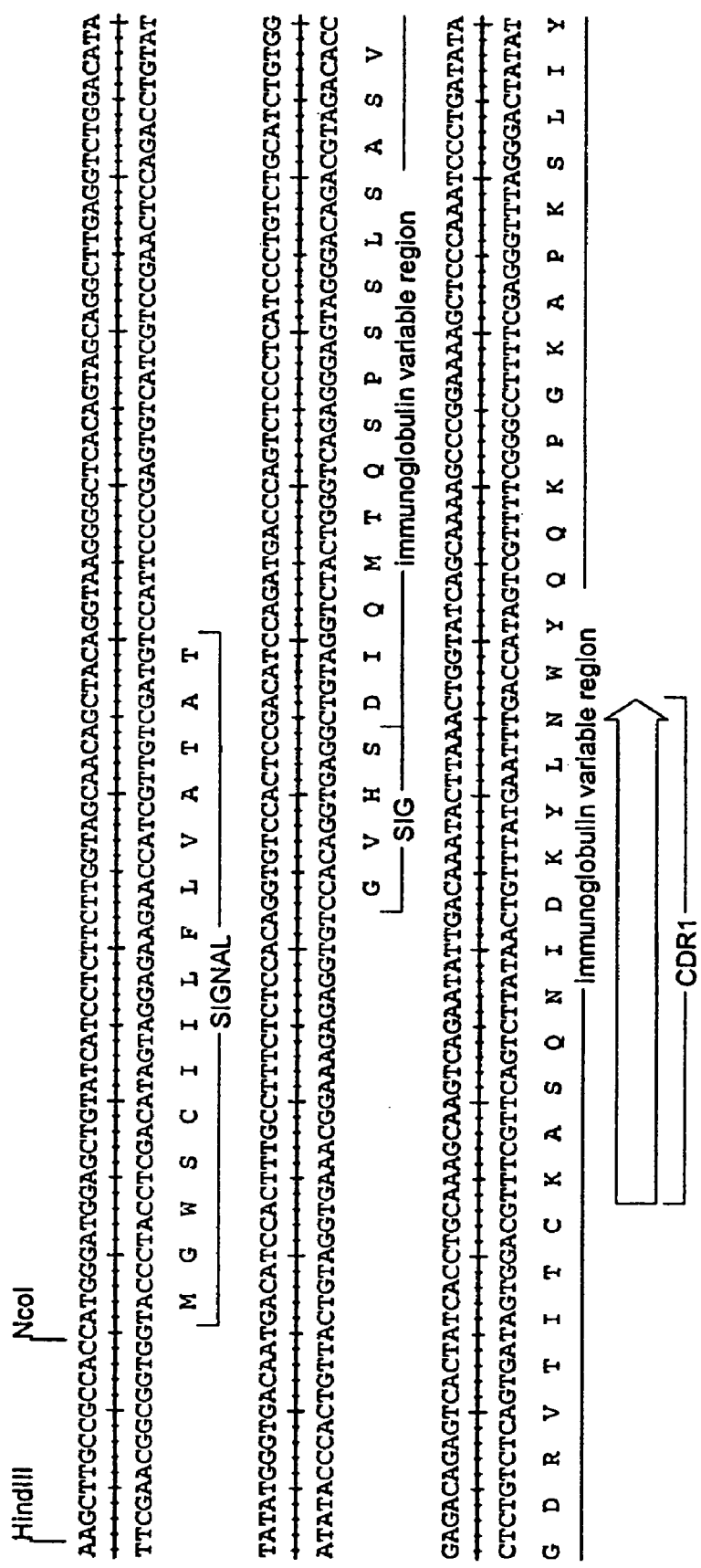
FIG. 11 depicts the DNA and amino acid sequences of modified light chain variable region DIVKv4 (SEQ ID NO:79 and SEQ ID NO:11, respectively).
Figure 11:
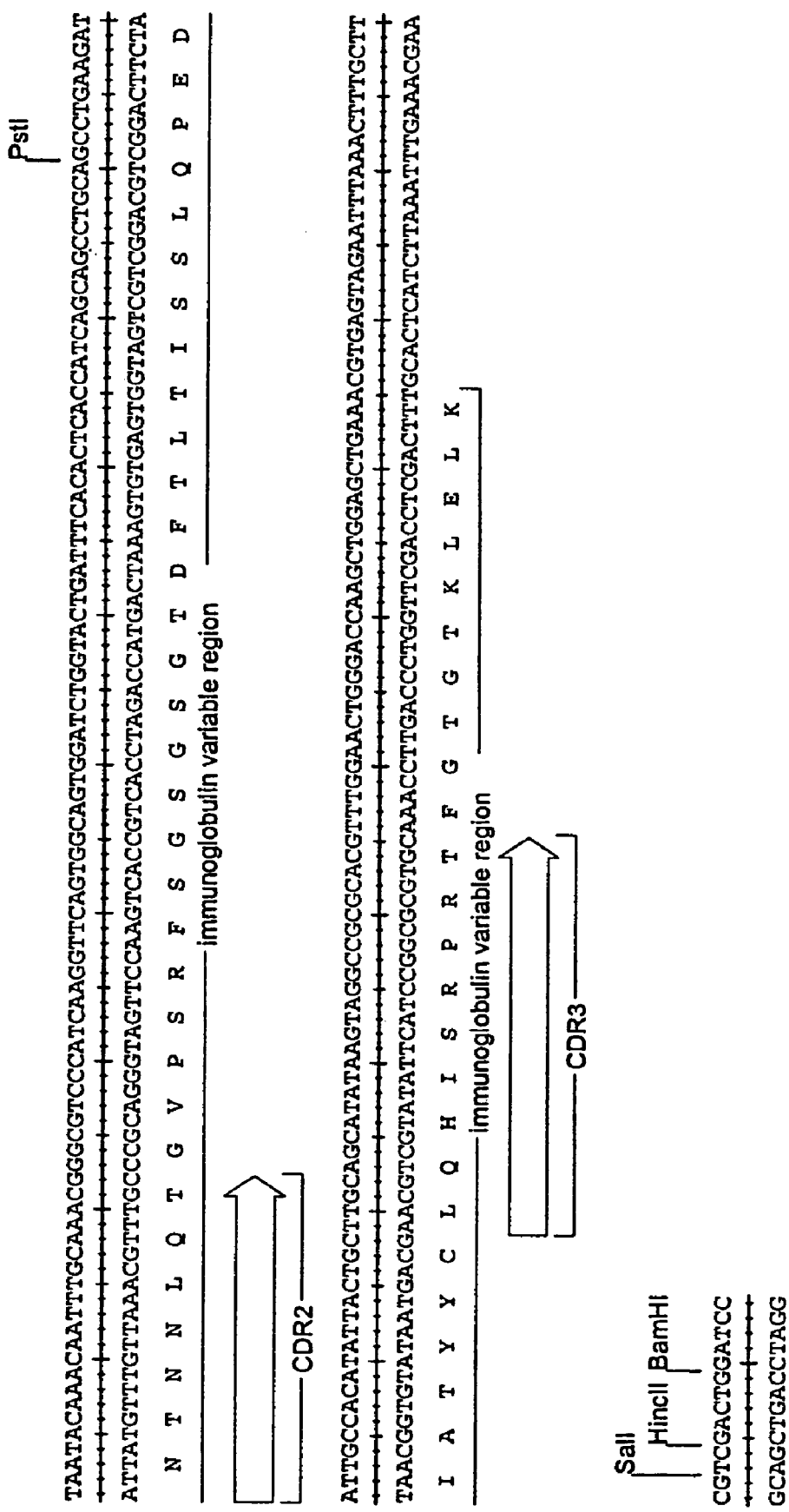
Figure 12:
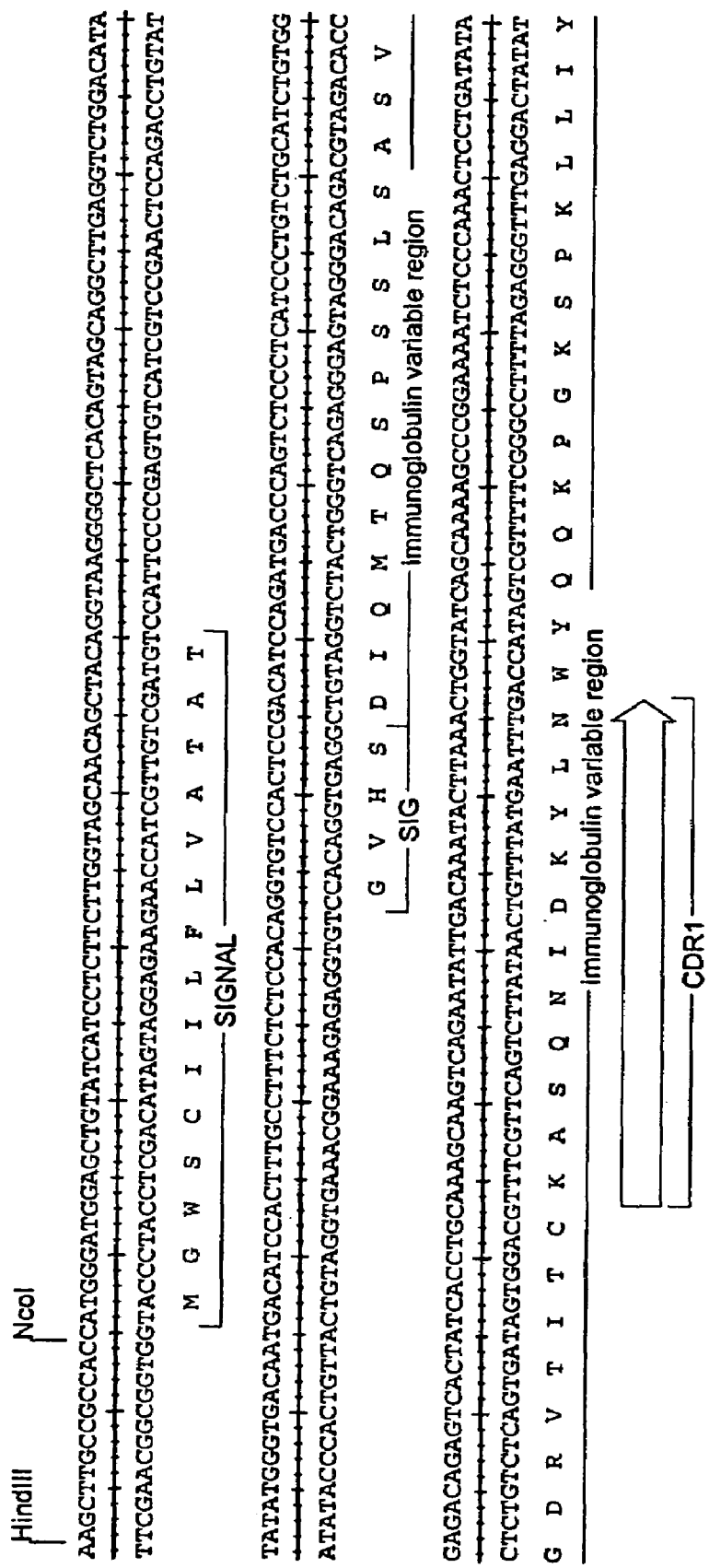
FIG. 12 depicts the DNA and amino acid sequences of modified light chain variable region DIVKv5 (SEQ ID NO:80 and SEQ ID NO:12, respectively).
Figure 12:
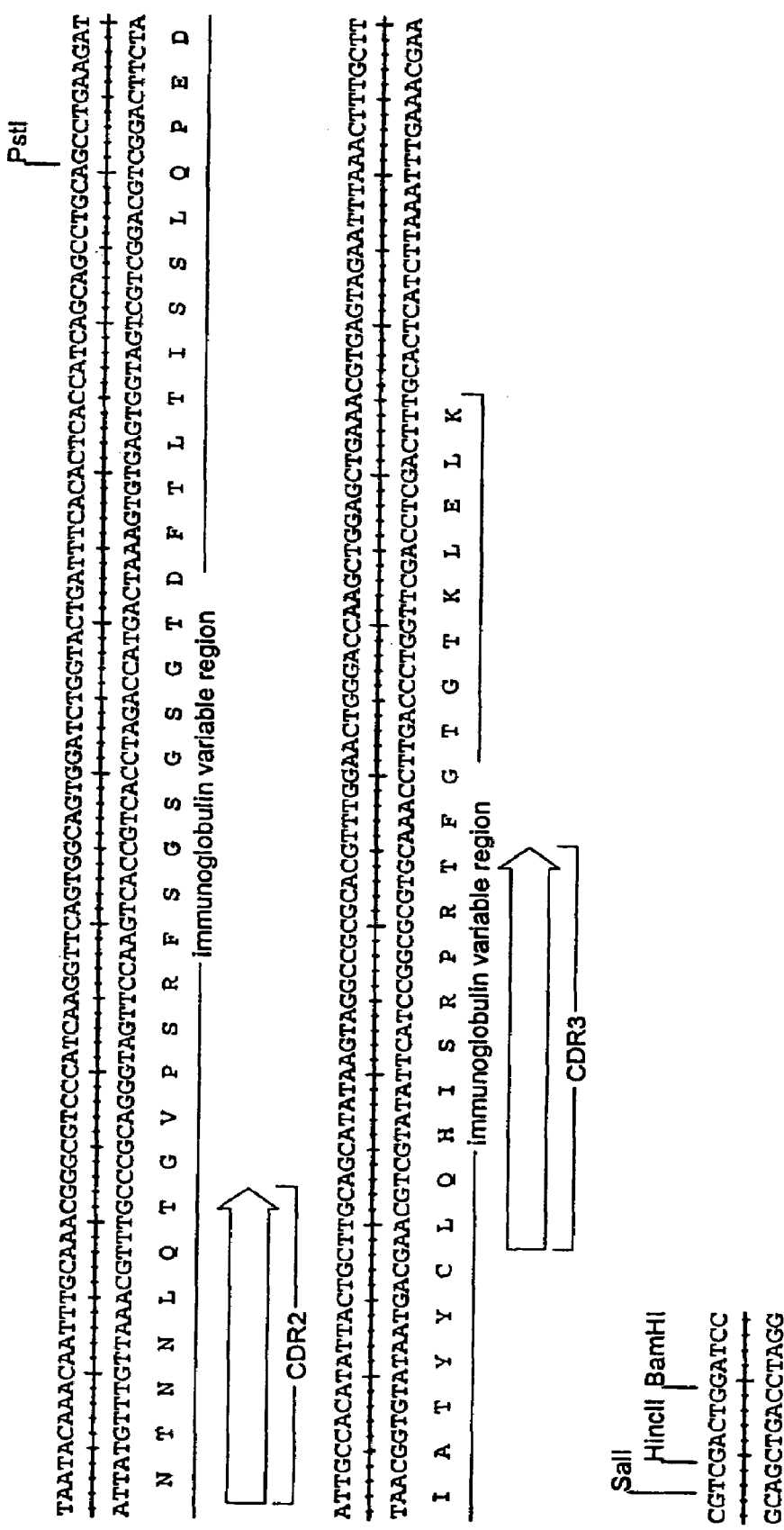

Another aspect of the present invention is an expression vector comprising a nucleic acid sequence coding a modified heavy or light chain of the present invention. In some embodiments, the expression vector comprises a nucleic acid sequence encoding a V-region heavy chain comprising a modified substituted variant of SEQ ID NO: 1 with a reduced number of potential T-cell epitopes, operably linked to an expression control sequence. In various embodiments, the expression vector comprises a nucleic acid sequence selected from the group consisting of SEQ ID NO: 71 through SEQ ID NO: 75 and SEQ ID NO: 81 through SEQ ID NO: 108, or a degenerate variant thereof. Degeneracy in relation to polynucleotides refers to the fact well recognized in the art that in the genetic code many amino acids are specified by more than one codon. The degeneracy of the code accounts for 20 different amino acids encoded by 64 possible triplet sequences of the four different bases. In some embodiments, the expression vector comprises a nucleic acid sequence encoding a V-region light chain comprising a modified substituted variant of SEQ ID NO: 2 with a reduced number of potential T-cell epitopes, operably linked to an expression control sequence. In various embodiments, the expression vector comprises a nucleic acid sequence selected from the group consisting of SEQ ID NO: 76 through SEQ ID NO: 80 and SEQ ID NO: 109 through SEQ ID NO: 138, or degenerate variant thereof. An example of a suitable expression vector for a heavy chain of the present invention is shown in FIG. 1 and an example of a suitable expression vector for a light chain of the present invention is shown FIG. 2. Another aspect of the present invention is a cultured cell comprising one or more of the aforementioned vectors. A further aspect of the present invention is a method of preparing an immunoglobulin, comprising culturing the aforementioned cell under conditions permitting expression under the control of suitable expression control sequence(s), and purifying the immunoglobulin from the medium of the cell.

Other aspects of the present invention are methods of therapeutic treatment. Embodiments encompass a method of treating lymphoid malignancies comprising administering to a patient an effective amount of a modified antibody according to the present invention. In some embodiments, the lymphoid malignancy is leukemia or lymphoma. Other embodiments include a method of treating autoimmune conditions in a patient comprising administering an effective amount of a modified antibody according to the present invention. In various embodiments the autoimmune condition is multiple sclerosis, rheumatoid arthritis, systemic vasiculitis, uveitis, inflammatory bowel disease or scleroderma.

Embodiments also include a method of immunosuppressing a patient prior to or subsequent to transplantation of an organ comprising administering to said patient an effective amount of an antibody according to the present invention. In some embodiments, the transplantation of on organ is a renal transplant.

Reference to "substantially non-immunogenic" or "reduced immunogenic potential" includes reduced immunogenicity compared to a parent antibody, i.e., a non-modified rodent or chimeric (rodent V-regions; human constant regions) monoclonal antibody or the humanized monoclonal antibody CAMPATH-1H. The term "immunogenicity" includes an ability to provoke, induce or otherwise facilitate a humoral and or T-cell mediated response in a host animal and in particular where the "host animal" is a human or the ability to elicit a response in a suitable in vitro assay, e.g., the dendritic cell/T-cell assay described herein.

A preferred feature of the modified antibodies of the present is that they substantially retain the functional activities of the non-modified or "parental" antibody CAMPATH-1G or the humanized antibody CAMAPATH-1H. Embodiments of the invention therefore encompass modified antibodies in which one or more of the beneficial technical features associated with the therapeutic efficacy of CAMPATH-1H or the parental non-modified antibody are exhibited. Such modified antibodies are useful in a number of important diseases in man including especially lymphoid malignancies such as leukemia and lymphoma, autoimmune conditions including, but not limited to, multiple sclerosis, rheumatoid arthritis, systemic vasiculitis, uveitis, inflammatory bowel disease and scleroderma and also for use in transplantations.

Accordingly, the modified antibody of the present exhibits an ability to bind to CD52 and in preferred embodiments the affinity for its target antigen CD52 is within an order of magnitude higher or lower than the affinity exhibited by the monoclonal antibody CAMPATH-1H.

The therapeutic efficacy of the parental molecule is believed also to be mediated by the ability of the antibody to induce antibody-dependent cell mediated cytotoxicity (ADCC) and complement dependent cytotoxicity (CDC). The phenomena of ADCC and CDC are mediated by the heavy chain constant region domain of whole antibody molecules, and the present invention contemplates production of a whole antibody molecules comprising a constant region domain compatible with ADCC and CDC induction. In preferred embodiments, the modified antibody comprises a human IgG1 constant region and a human kappa constant region domain.

By "antibody" is meant a protein of the immunoglobulin family that is capable of combining, interacting or otherwise associating with an antigen. The term "antigen" is used herein to refer to a substance that is capable of interacting with the antibody and in the context of the present invention is meant to be CD52.

The term "immunoglobulin" is used herein to refer to a protein consisting of one or more polypeptides substantially encoded by immunoglobulin genes. The recognised immunoglobulin genes include the κ, λ, α, γ (IgG1, IgG2, IgG3, IgG4), σ, ε and μ constant region genes and in nature multiple immunoglobulin variable region genes. One natural form of immunoglobulin is a tetramer comprising two identical pairs in which each pair has one light chain and one heavy chain. In each pair the heavy and light chain variable regions together provide the binding surface capable of interacting with the antigen. The term Vh is used herein to refer to the heavy chain variable region, and the term Vk is used herein to refer to the light chain variable region and in this instance in common with numerous monoclonal antibodies the light chain is a "kappa" (k) type chain.

As used herein, Vh means a polypeptide that is about 110 to 125 amino acid residues in length, the sequence of which corresponds to any of the specified Vh chains herein which in combination with a Vk are capable of binding CD52 antigen. Similarly, Vk means a polypeptide that is about 95-130 amino acid residues in length the sequence of which corresponds to any of the specified Vk chains herein which in combination with a Vh are capable of binding the CD52 antigen. Full-length immunoglobulin heavy chains are about 50 kDa molecular weight and are encoded by a Vh gene at the N-terminus and one of the constant region genes (e.g., γ) at the C-terminus. Similarly, full-length light chains are about 25 kDa molecular weight and are encoded by a V-region gene at the N-terminus and a κ or λ constant region gene at the C-terminus.

In addition to whole antibody (tetramers), immunoglobulins may exist in a number of other forms derived by application of recombinant DNA techniques or protein biochemistry. These forms include for example Fv, Fab, Fab' and (Fab)2 molecules and could all contain any of the Vh or Vk sequences of the present invention. A further example may include a "bi-specific" antibody comprising a Vh/Vk combination of the present invention in combination with a second Vh/Vk combination with a different antigen specificity.

The term "potential T-cell epitope" means according to the understanding of this invention an amino acid sequence which has potential to bind MHC class II. Such sequences may stimulate T-cells and/or bind (without necessarily measurably activating) T-cells in complex with MHC class II.

The term "peptide" as used herein and in the appended claims, is a compound that includes two or more amino acids. The amino acids are linked together by a peptide bond (defined herein below). There are 20 different naturally occurring amino acids involved in the biological production of peptides, and any number of them may be linked in any order to form a peptide chain or ring. The naturally occurring amino acids employed in the biological production of peptides all have the L-configuration. Synthetic peptides can be prepared employing conventional synthetic methods, utilizing L-amino acids, D-amino acids, or various combinations of amino acids of the two different configurations. Some peptides contain only a few amino acid units. Short peptides, e.g., having less than ten amino acid units, are sometimes referred to as "oligopeptides". Other peptides contain a large number of amino acid residues, e.g., up to 100 or more, and are referred to as "polypeptides". By convention, a "polypeptide" may be considered as any peptide chain containing three or more amino acids, whereas a "oligopeptide" is usually considered as a particular type of "short" polypeptide. Thus, as used herein, it is understood that any reference to a "polypeptide" also includes an oligopeptide. Further, any reference to a "peptide" includes polypeptides, oligopeptides, and proteins. Each different arrangement of amino acids forms different polypeptides or proteins. The number of polypeptides—and hence the number of different proteins—that can be formed is practically unlimited.

The general method of the present invention leading to the modified anti-CD52 antibody comprises the following steps:
  (a) Determining the amino acid sequence of the polypeptide or part thereof.
  (b) Identifying one or more potential T cell epitopes within the amino acid sequence of the protein by any method including determination of the binding of the peptides to MHC molecules using in vitro or in silico techniques or biological assays.
  (c) Designing new sequence variants with one or more amino acids within the identified potential T cell epitopes modified in such a way to substantially reduce or eliminate binding of the peptides to MHC molecules measured by in vitro or in silico techniques or biological assays. Such sequence variants are created in such a way to avoid creation of new potential T cell epitopes by the sequence variations unless such new potential T cell epitopes are, in turn, modified in such a way to substantially reduce or eliminate binding of peptides to MHC class II molecules.
  (d) Constructing such sequence variants by recombinant DNA techniques and testing said variants in order to identify one or more variants with desirable properties.

The identification of potential T-cell epitopes according to step (b) can be carried out according to methods described previously in the art. Suitable methods are disclosed in WO 98/59244; WO 00/34317; U.S. Application 20030153043, all incorporated herein by reference.

In practice a number of variant anti-CD52 antibodies may be produced and tested for the desired immune and functional characteristic. It is particularly important when conducting alterations to the protein sequence that the contemplated changes do not introduce new immunogenic epitopes. This event is avoided in practice by re-testing the contemplated sequence for the presence of epitopes and or of MHC class II ligands by any suitable means.

In various embodiments, the modified antibodies of the present invention are generated by expression of different combinations of the Vh and Vk genes specified herein. All such combinations of heavy and light chain are encompassed by the present invention.

The invention relates to an anti-CD52 antibody in which substitutions of at least one amino acid residue have been made at positions within the V-regions of the molecule to result in the elimination of one or more potential T-cell epitopes from the protein. It is most preferred to provide modified antibody molecules in which amino acid modification (e.g., a substitution) is conducted within the most immunogenic regions of the parent molecule. The various embodiments of the present invention comprise modified antibody molecules for which any of the MHC class II ligands are altered such as to eliminate binding or otherwise reduce the numbers of MHC allotypes to which the peptide can bind. The inventors have discovered and herein disclose, the immunogenic regions of the CAMPATH antibody molecule in man. It is understood that under certain circumstances additional regions of sequence to those disclosed herein can become immunogenic epitopes, for example in the event of infection with a pathogen expressing a protein or peptide with a similar sequence to that of the present case.

MHC class II epitope removal has involved amino acid substitution to create modified variants depleted of potential T-cell epitopes. The amino acid substitutions have been made at appropriate points within the peptide sequence predicted to achieve substantial reduction or elimination of the activity of the undesired potential T cell epitope. Examples of particularly useful substitutions in this respect are provided in Tables 1 and 2, wherein Table 1 relates to Vh region substitutions and Table 2 relates to Vk region substitutions.

As will be clear to the person skilled in art, multiple alternative sets of substitutions could be arrived at which achieve the objective of removing un-desired epitopes. The resulting sequences would however remain broadly homologous with the specific compositions disclosed herein and therefore fall under the scope of the present invention. It would be typical to arrive at sequences that were around 70%, or around 90%, or around 95%, or around 99% or more homologous with the present specified sequences over their least homologous region and yet remain operationally equivalent. Such sequences would equally fall under the scope of the present.

It is understood that single amino acid substitutions within a given potential T cell epitope are the most preferred route by which the epitope may be eliminated. Combinations of substitution within a single epitope may be contemplated and for example can be particularly appropriate where individually defined epitopes are in overlap with each other. Moreover, amino acid substitutions either singly within a given epitope or in combination within a single epitope may be made at positions not equating to the "pocket residues" with respect to the MHC class II binding groove, but at any point within the peptide sequence. All such substitutions fall within the scope of the present.

In as far as this invention relates to modified anti-CD52 antibodies, compositions containing such modified antibodies or fragments of modified antibodies and related compositions should be considered within the scope of the invention. The invention therefore contemplates the use and generation of antibody fragments including for example Fv, Fab, Fab' and F(ab')2 fragments. Such fragments may be prepared by standard methods [for example; Coligan et al., *Current Protocols in Immunology*, John Wiley & Sons 1991-1997, incorporated herein by reference]. The present invention also contemplates the various recombinant forms of antibody derived molecular species well known in the art. Such species include stabilised Fv fragments including single chain Fv forms (e.g., scFv) comprising a peptide linker joining the Vh and Vk domains, or an Fv stabilised by interchain di-sulphide linkage (dsFv) and which contain additional cysteine residues engineered to facilitate the conjoining of the Vh and Vk domains. Equally, other compositions are familiar in the art and could include species referred to as "minibodies"; and single variable domain "dAbs." Other species still may incorporate means for increasing the valency of the modified antibody V-region domain, i.e. species having multiple antigen binding sites for example by the engineering of dimerisation domains (e.g., "leucine zippers") or also chemical modification strategies.

Under the scheme of the present there are provided a number of different H-chain V-region and L-chain V-region sequences. The present disclosure provides no limit to the possible combinations of H-chain and L-chain that may be provided to constitute a complete antibody molecule. Constitution of the complete antibody molecule may be achieved by recombinant DNA techniques and methods for purifying and manipulating antibody molecules well known in the art. Necessary techniques are explained fully in the literature, such as, "Molecular Cloning: A Laboratory Manual," second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology" (D. M. Weir & C. C. Blackwell, eds.); "Gene Transfer Vectors for Mammalian Cells" (J. M. Miller & M. P. Calos, eds., 1987); "Current Protocols in Molecular Biology" (Ausubel et al., eds., 1987); "PCR: The Polymerase Chain Reaction," (Mullis et al., eds., 1994); "Current Protocols in Immunology" (Coligan et al., eds., 1991).

The preferred molecules of this invention can be prepared in any of several ways but is most preferably conducted exploiting routine recombinant methods. It is a relatively facile procedure to use the protein sequences and information provided herein to deduce a polynucleotide (DNA) encoding any of the preferred antibody V-regions. This can be achieved for example using computer software tools such as the DNAstar software suite [DNAstar Inc, Madison, Wis., USA] or similar. Any such DNA sequence with the capability of encoding the preferred polypeptides of the present or significant homologues thereof, should be considered as embodiments of this invention.

As a general scheme any of the Vh or Vk chain genes can be made using gene synthesis and cloned into a suitable expression vector. In turn the expression vector is introduced into a host cell and cells selected and cultured. The antibody molecules are readily purified from the culture medium and formulated into a preparation suitable for therapeutic administration.

By way of a non-limiting example, one such scheme involves a gene synthesis process using panels of synthetic oligonucleotides. The genes are assembled using a ligase chain reaction (LCR) wherein the oligonucleotides featuring complementary ends are allowed to anneal followed by amplification and fill-in using a polymerase chain reaction (PCR). The PCR is driven by addition of an increased concentration of the flanking oligonucleotides to act as primers. The PCR products are assembled into full-length antibody genes by further PCR from vectors containing 5' and 3' immunoglobulin gene flanking regions and sub-cloning into expression vectors for expression of whole antibody. The assembled Vh and Vk genes can serve as templates for mutagenesis and construction of multiple variant antibody sequences such as any of those disclosed herein. It is particularly convenient to use the strategy of "overlap extension PCR" as described by Higuchi et al. [1988, *Nucleic Acids Res*. 16: 7351], although other methodologies and systems could be readily applied.

Full-length immunoglobulin genes containing the variable region cassettes are most conveniently assembled using overlapping PCR and sub-cloned into expression vectors containing the desired immunoglobulin constant region domains. The expression vectors may be introduced into a mammalian or other host cell for example using electroporation techniques. The NS0 cell line is a non-immunoglobulin producing mouse myeloma, obtained from the European Collection of Animal Cell Cultures (ECACC) and is particularly suitable example host cell line for this procedure. Cell lines secreting antibody are expanded and antibody can be readily purified for example by use of protein A affinity chromatography [Harlow & Lane, ibid]. The concentration of the purified antibody can be determined using an enzyme linked immunosorbent assay (ELISA) detecting the human kappa constant region of the antibodies of interest.

In a further aspect the present invention relates to methods for therapeutic treatment of humans using the modified antibody compositions. For administration to an individual, any of the modified antibody compositions would be produced to be preferably at least 80% pure and free of pyrogens and other contaminants. It is further understood that the therapeutic compositions of the modified antibody proteins may be used in conjunction with a pharmaceutically acceptable excipient. The pharmaceutical compositions according to the present invention are prepared conventionally, comprising substances that are customarily used in pharmaceuticals, e.g., Remington's Pharmaceutical Sciences, (Alfonso R. Gennaro, ed., 18th edition, 1990), including excipients, carriers, adjuvants, and buffers. The compositions can be administered, e.g., parenterally, enterally, intramuscularly, subcutaneously, intravenously, or other routes useful to achieve an effect. For example: anti-CD52 antibodies can be given intravenously (Cloes et al. (1999) *Ann. Neurol.*, 46:296-304; Moreau et al. (1996) *Multiple Sclerosis*, 1:357-65; Moreau et al. (1994) *Lancet*, 344:298-301, all herein incorporated by reference) and subcutaneously (Schnitzer et al. (1997) *J. Rheumatol.*, 24:1031-6; Bowen et al. (1997) *Br. J. Hematol.*, 96:617-9, both herein incorporated by reference). Conventional excipients include pharmaceutically acceptable organic or inorganic carrier substances suitable for parenteral, enteral, and other routes of administration that do not deleteriously react with the agents. For parenteral application, particularly suitable are injectable sterile solutions, preferably oil or aqueous solutions, as well as suspensions, emulsions or implants, including suppositories. Ampoules are convenient unit dosages. The pharmaceutical preparations can be sterilized and, if desired, mixed with stabilizers, wetting agents, emulsifiers, salts for influencing osmotic pressure, buffers, or other substances that do not react deleteriously with the active compounds.

In the methods of the present invention, the actual dosage of the anti-CD52 antibodies of the present invention employed will depend on a variety of factors including the type and severity of disorder being treated, and other treatment modality or modalities selected. Guidance for dosage regimens is obtained from dosing of CAMPATH-1H known in the art.

EXPERIMENTAL EXAMPLES

Example 1

Construction of Anti-CD52 Antibody $V_H$ and $V_K$ Genes

The sequence of the rat anti-CD52 antibody was derived from data base entries RNIGHCC1G for the variable domain heavy chain ($V_H$), and RNIGKCC1G for the variable domain light chain ($V_K$). The sequences were modified slightly to remove internal HindIII and BamHI sites without altering the amino acid sequence. The $V_H$ and $V_K$ genes were made by gene synthesis. Briefly, a panel of synthetic oligonucleotides was designed and synthesised. The genes were assembled using a ligase chain reaction (LCR) wherein the oligonucleotides featuring complementary ends were allowed to anneal followed by amplification and fill-in using a polymerase chain reaction (PCR). The PCR was driven by addition of an increased concentration of the flanking oligonucleotides to act as primers. The PCR products were assembled into full-length antibody genes by further PCR from vectors containing 5' and 3' immunoglobulin gene flanking regions and sub-cloning into expression vectors for expression of whole antibody. The assembled $V_H$ and $V_K$ genes served as templates for mutagenesis and construction of multiple variant antibody sequences in which potential T-cell epitopes had been removed.

For assembly of the $V_H$ gene oligonucleotides VH1 to VH20 detailed in Table 3 were used. For assembly of the $V_K$ gene oligonucleotides VK1 to VK20 detailed in Table 4 were used. For both genes, the LCR was conducted by mixing 20 μl of phosphorylated oligonucleotides with 1 μl Pfu DNA ligase (Stratagene, Amsterdam, NL), 10 μl 10× reaction buffer (supplied with enzyme) and 69 μl water. The reaction mix was placed in a thermal cycler for incubation at 95° C. for 2 minutes followed by 25 cycles of 95° C. for 30 seconds, gradual cooling to 50° C., incubation at 50° C. for 30 seconds, and 55° C. for 20 minutes, followed by a final incubation of 3 hours at 55° C. Analysis of a sample of the LCR using 1% agarose gel electrophoresis gave a smear with a faint band of correct size just visible. The oligonucleotides in all cases were from Sigma-Genosys (Pampisford, UK) and were phosphorylated in vitro using T4 DNA kinase (Promega, Southampton, UK) and the supplier's recommended protocol. Following LCR, 5 μL of the reaction was transferred to a PCR mix to amplify the assembled fragment. Oligonucleotides VH1 and VH20 were used to drive the $V_H$ reaction, with oligonucleotides VK1 and VK20 used to drive the $V_K$ reaction. PCR was conducted in a total volume of 50 μl for 30 cycles using 1 μl Pfu DNA polymerase (Stratagene, Amsterdam, NL). Analysis of a sample of the PCR using 1% agarose gel electrophoresis gave a band of 380 bp for $V_H$ and 377 bp for $V_K$.

Variable region cassettes were assembled using overlapping PCR. Briefly, DNAs derived from the vectors M13-VHPCR1 and M13-VKPCR1 [Orlandi et al. (1989), PNAS, 89: 3833-7] were used as templates to produce a further two overlapping PCR fragments for each $V_H$ and $V_K$ chain including 5' flanking sequence encoding the leader signal peptide and 3' flanking sequence including a splice site and intron sequences. The DNA fragments so produced for the $V_H$ and $V_K$ were combined in a PCR using flanking primers required to obtain full-length DNA sequences. The primer pairs used in these "linking" reactions were oligonucleotides VHVK5'CHO/VHVK3'SIG and VH19/VH12 for the $V_H$ gene, whereas for the $V_K$ gene, the oligonucleotides VHVK5'CHO/VHVK3'SIG and VK19/VK3'CHO were used.

After purification using a Qiagen (Crawley, UK) PCR PREP kit the PCR products were cut with HindIII and BamHI (Promega, Southampton, UK) and run on a 1% agarose gel. The desired bands were removed and purified using a Qiagen (Crawley, UK) DNA extraction kit. The products were cloned into HindIII and BamHI cut pUC19 vector and the DNA sequence confirmed.

TABLE 3

Oligonucleotides for synthesis of $V_H$ gene

| Name | Sequence | SEQ ID NO: |
|------|----------|------------|
| VH1  | TCCACAGGTGTCCACTCCGA | 141 |
| VH2  | CCAGATTCCAACAGTTTCACCTCGGAGTGGACACCT GTGGA | 142 |
| VH3  | GGTGAAACTGTTGGAATCTGGAGGAGGCTTGGTACA GCC | 143 |
| VH4  | GGAGAGTCTCATAGAACCCCCCGGCTGTACCAAGCC TCCT | 144 |
| VH5  | GGGGGGTTCTATGAGACTCTCCTGTGCAGGTTCTGG ATTCA | 145 |
| VH6  | CATGTAGAAATCAGTGAAGGTGAATCCAGAACCTGC ACA | 146 |
| VH7  | CCTTCACTGATTTCTACATGAACTGGATTCGCCAGC CTGC | 147 |
| VH8  | GCCACTCAGGTGCCTTCCCTGCAGGCTGGCGAATCC AGTT | 148 |
| VH9  | AGGGAAGGCACCTGAGTGGCTGGGTTTTATTAGAGA CAAA | 149 |
| VH10 | TCTGTTGTGTAACCTTTAGCTTTGTCTCTAATAAAA CCCA | 150 |
| VH11 | GCTAAAGGTTACACAACAGAGTACAATCCATCTGTG AAGGGG | 151 |
| VH12 | TCTGGAGATGGTGAACCGCCCCTTCACAGATGGATT GTAC | 152 |
| VH13 | CGGTTCACCATCTCCAGAGATAATACCCAAAACATG CT | 153 |
| VH14 | GGGTGTTCATTTGAAGATAGAGCATGTTTTGGGTAT TATC | 154 |
| VH15 | CTATCTTCAAATGAACACCCTAAGAGCTGAGGACAC TGCC | 155 |
| VH16 | TCTCTTGCACAGTAGTAAGTGGCAGTGTCCTCAGCT CTTA | 156 |

TABLE 3-continued

Oligonucleotides for synthesis of $V_H$ gene

| Name | Sequence | SEQ ID NO: |
|---|---|---|
| VH17 | ACTTACTACTGTGCAAGAGAGGGCCACACTGCTGCTCCTTTT | 157 |
| VH18 | CTCCTTGGCCCCAGTAATCAAAAGGAGCAGCAGTGTGGCCC | 158 |
| VH19 | GATTACTGGGGCCAAGGAGTCATGGTCACCGTCTCCTCA | 159 |
| VH20 | TGAGGAGACGGTGACCATGA | 160 |
| VHVK5'CHO | GCATGTTGACCCTGACGCAAGCTTGCCGCCACCATGGG | 161 |
| VHVK3'SIG | GGAGTGGACACCTGTGGAGAGAAAGGC | 162 |
| VH12 | GCGATAGCTGGACTGAATGGATCCTATAAATCTCTG | 163 |

TABLE 4

Oligonucleotides for synthesis of $V_K$ gene

| Name | Sequence | SEQ ID NO: |
|---|---|---|
| VK1 | TCCACAGGTGTCCACTCCGAC | 164 |
| VK2 | AGACTGGGTCATCTTGATGTCGGAGTGGACACCTGTGGA | 165 |
| VK3 | ATCAAGATGACCCAGTCTCCCTCATTCCTGTCTGCATCTG | 166 |
| VK4 | AGAGTGACTCTGTCTCCCACAGATGCAGACAGGAATGAGGG | 167 |
| VK5 | TGGGAGACAGAGTCACTCTCAACTGCAAAGCAAGTCAGAA | 168 |
| VK6 | GTTTAAGTATTTGTCAATATTCTGACTTGCTTTGCAGTTG | 169 |
| VK7 | TATTGACAAATACTTAAACTGGTATCAGCAAAAGCTGGGA | 170 |
| VK8 | TCAGGAGTTTGGGAGATTCTCCCAGCTTTTGCTGATACCA | 171 |
| VK9 | GAATCTCCCAAACTCCTGATATATAATACAAACAATTTGC | 172 |
| VK10 | CCTTGATGGGATGCCCGTTTGCAAATTGTTTGTATTATATA | 173 |
| VK11 | AAACGGGCATCCCATCAAGGTTCAGTGGCAGTGGATCTGG | 174 |
| VK12 | GGTGAGTGTGAAATCAGTACCAGATCCACTGCCACTGAA | 175 |
| VK13 | TACTGATTTCACACTCACCATCAGCAGCCTGCAGCCTGAA | 176 |
| VK14 | CAGAAATATGTGGCAACATCTTCAGGCTGCAGGCTGCTGAT | 177 |
| VK15 | GATGTTGCCACATATTTCTGCTTGCAGCATATAAGTAGG | 178 |

TABLE 4-continued

Oligonucleotides for synthesis of $V_K$ gene

| Name | Sequence | SEQ ID NO: |
|---|---|---|
| VK16 | CCCAGTTCCAAACGTGCGCGGCCTACTTATATGCTGCAAG | 179 |
| VK17 | CCGCGCACGTTTGGAACTGGGACCAAGCTGGAGCTGAAAC | 180 |
| VK18 | AAAGTTTAAATTCTACTCACGTTTCAGCTCCAGCTTGGT | 181 |
| VK19 | GTGAGTAGAATTTAAACTTTGCTTCGTCGACTGGATCC | 182 |
| VK20 | GGATCCAGTCGACGAAGC | 183 |
| VHVK5'CHO | GCATGTTGACCCTGACGCAAGCTTGCCGCCACCATGGG | 184 |
| VHVK3'SIG | GGAGTGGACACCTGTGGAGAGAAAGGC | 185 |
| VK3'CHO | GCGATAGCTGGACTGAATGGATCCAGTCGACGAAGC | 186 |

Chimeric heavy and light chain expression vectors have been constructed consisting of the rat anti-CD52 variable regions linked to human IgG1 [Takahashi et al. (1982) *Cell* 29: 671] or κ [Heiter et al. (1980) *Cell* 22: 197] constant regions. These composite antibody genes were then transferred to expression vectors for production of recombinant antibody. The antibody genes are under the control of the human cytomegalovirus immediate early promoter. The heavy chain vector includes the dhfr gene and the light chain vector the neo gene for selection in mammalian cells. The DNA sequence was confirmed to be correct for the $V_H$ and $V_K$ in the chimaeric expression vectors.

Example 2

Construction of Modified Antibody $V_H$ and $V_K$ Genes

Modified $V_H$ and $V_K$ genes were constructed by PCR mutagenesis using the rat anti-CD52 variable region cassettes generated in Example 1 as templates. Table 5 lists the oligonucleotides used in the production of modified $V_H$s. The following mutations are identified by the Kabat number of the residue with the linear number relating to the respectively identified polypeptide acid sequence in parenthesis. DIVHv1 (polypeptide SEQ ID NO: 3; polynucleotide SEQ ID NO: 71) included the mutations K3Q (3), M18L (18), I37V (37), P40A (40), A41P (41), A44G (44), P45L (45), L48V (48), T74S (77), Q75K (78), M77T (80), T82bS (87), T89V (95), V107T (115), M108L (116), and used oligonucleotides VHVK5'CHO, DIVH1, DIVH2, DIVH3, DIVH4, DIVH5, DIVH6, DIVH7, DIVH8, DIVH9, DIVH10, and VH12. DIVHv2 (polypeptide SEQ ID NO: 4; polynucleotide SEQ ID NO: 72) included the mutations K3Q (3), M18L (18), A41P (41), L48I (48), T74S (77), Q75K (78), M77T (80), T82bS (87), T89V (95), V107T (115), M108L (116), and used oligonucleotides VHVK5'CHO, DIVH1, DIVH2, DIVH3, DIVH4, DIVH5A, DIVH6A, DIVH7, DIVH8, DIVH9, DIVH10, and VH12. DIVHv3 (polypeptide SEQ ID NO: 5; polynucleotide SEQ ID NO: 73) included the mutations L5Q (5), L20I (20), A23S (23), A41P (41), A44G (44), L48I (48), M77T (80), Y79H (82), M82A (85), T89V (95), V107T (115), M108T (106), and used oligonucleotides VHVK5'CHO, DIVH11, DIVH12, DIVH13, DIVH14, DIVH15, DIVH16, DIVH17, DIVH18, DIVH19, DIVH20, and VH12. DIVHv4 (polypeptide SEQ ID NO: 6; polynucleotide SEQ ID NO: 74) included the mutations K3Q (3), M18L (18), I37V (37), P40A (40), A41P (41), A44G (44), P45L (45), L48V (48), T74A (77), Q75K (78), M77S (80), T82bS (87), T89V (95), V107T (115), M108L (116), and used oligonucleotides VHVK5'CHO, DIVH1, DIVH2, DIVH3, DIVH4, DIVH5, DIVH6, DIVH7, DIVH8, DIVH9, DIVH10, DIVH21, DIVH22 and VH12. DIVHv5 (polypeptide SEQ ID NO: 7; polynucleotide SEQ ID NO: 75) included the mutations K3Q (3), M18L (18), A41P (41), T74S (77), Q75K (78), M77T (80), T82bS (87), T89V (95), V107T (115), M108L (116) and used oligonucleotides VHVK5'CHO, DIVH1, DIVH2, DIVH3, DIVH4, DIVH23, DIVH6A, DIVH7, DIVH8, DIVH9, DIVH10, and VH12.

TABLE 5

Oligonucleotides used in the construction of modified ant-CD52 V$_H$s

| Name | Sequence | SEQ ID NO: |
|---|---|---|
| VHVK5'CHO | GCATGTTGACCCTGACGCAAGCTTGCCGCCACCATGGG | 187 |
| DIVH1 | CCACTCCGAGGTGCAACTGTTGGAATCTGG | 188 |
| DIVH2 | CCAGATTCCAACAGTTGCACCTCGGAGTGG | 189 |
| DIVH3 | AGCCGGGGGGTTCTCTGAGACTCTCCTGTG | 190 |
| DIVH4 | CACAGGAGAGTCTCAGAGAACCCCCCGGCT | 191 |
| DIVH5 | AGGGAAGGGACTTGAGTGGGTGGGTTTTATTAGAG | 192 |
| DIVH5A | CGGGAAAGCACCTGAGTGGATTGGTTTTATTAGAG | 193 |
| DIVH6 | CCACTCAAGTCCCTTCCCTGGAGCCTGGCGGACCCAGTTCATG | 194 |
| DIVH6A | CCACTCAGGTGCTTTCCCGGGAGGCTGGCGAATCC | 195 |
| DIVH7 | TCTTCAAATGAACTCCCTAAGAGCTGAGGACACTGCCGTTTACTACTG | 196 |
| DIVH8 | AGGGAGTTCATTTGAAGATAGAGGGTGTTTTTGGAATTATCTCTGG | 197 |
| DIVH9 | TGGGGCCAAGGAACACTGGTCACCGTCTCCTCAGG | 198 |
| DIVH10 | GGAGACTGTGACCAGTGTTCCTTGGCCCCAG | 199 |
| DIVH11 | TCCGAGGTGAAACTGCAGGAATCTGGAGGAGGC | 200 |
| DIVH12 | CCAGATTCCTGCAGTTTCACCTCGGAGTGG | 201 |
| DIVH13 | GGGGGTTCTATGAGAATCTCCTGTTCAGGTTCTGG | 202 |
| DIVH14 | GAACCTGAACAGGAGATTCTCATAGAACCCCCGG | 203 |
| DIVH15 | CGGGAAAGGACCTGAGTGGATTGGTTTTATTAGAG | 204 |
| DIVH16 | CCAATCCACTCAGGTCCTTTCCCGGGAGGCTGGCG | 205 |
| DIVH17 | GCTAACACCCTAAGAGCTGAGGACACTGCCGTTTACTACTG | 206 |
| DIVH18 | CTCTTAGGGTGTTAGCTTGAAGATGGAGGGTGTTTTGGG | 207 |

TABLE 5-continued

Oligonucleotides used in the construction of modified ant-CD52 V$_H$s

| Name | Sequence | SEQ ID NO: |
|---|---|---|
| DIHH19 | TGGGGCCAAGGAACTACCGTCACCGTCTCCTCAGG | 208 |
| DIVH20 | GGAGACGGTGACGGTAGTTCCTTGGCCCCAG | 209 |
| DIVH21 | GATAATGCCAAAAACTCCCTCTATCTTCAAATGAAC | 210 |
| DIVH22 | ATAGAGGGAGTTTTTGGCATTATCTCTGGAGATGG | 211 |
| DIVH23 | CGGGAAAGCACCTGAGTGGCTGGGTTTTATTAGAG | 212 |
| VH12 | GCGATAGCTGGACTGAATGGATCCTATAAATCTCTG | 213 |

Table 6 lists the oligonucleotides used in the production of modified V$_K$s. The following mutations are identified by the Kabat numbers of the residues and are the same as the linear numbering of the respectively identified polypeptide sequences. DIVKv1 (polypeptide SEQ ID NO: 8; polynucleotide SEQ ID NO: 76) included the mutations K3Q, F10S, L21I, N22T, K24R, L40P, E42K, S43A, L46S, T56S, I58V, V83I, F87Y, and used oligonucleotides VHVK5'CHO, DIVK1, DIVK2, DIVK3A, DIVK4A, DIVK5B, DIVK6, DIVK7, DIVK8A, DIVK9, DIVK10, and VK3'CHO. DIVKv2 (polypeptide SEQ ID NO: 9; polynucleotide SEQ ID NO: 77) included the mutations K3Q, F10S, L21I, N22T, L40P, E42K, S43A, I58V, V83I, F87Y, and used oligonucleotides VHVK5'CHO, DIVK1, DIVK2, DIVK3, DIVK4, DIVK5, DIVK6, DIVK7, DIVK8, DIVK9, DIVK10, and VK3'CHO. DIVKv3 (polypeptide SEQ ID NO: 10; polynucleotide SEQ ID NO: 78) included the mutations K3Q, F10S, L21I, N22T, K24R, L40P, E42K, S43A, T56S, I58V, V83I, F87Y, and used oligonucleotides VHVK5'CHO, DIVK1, DIVK2, DIVK3A, DIVK4A, DIVK5, DIVK6, DIVK7, DIVK8A, DIVK9, DIVK10, and VK3'CHO. DIVKv4 (polypeptide SEQ ID NO: 11; polynucleotide SEQ ID NO: 79) included the mutations K3Q, F10S, L21I, N22T, L40P, E42K, S43A, L46S, I58V, V83I, F87Y, and used oligonucleotides VHVK5'CHO, DIVK1, DIVK2, DIVK3, DIVK4, DIVK5B, DIVK6, DIVK7, DIVK8, DIVK9, DIVK10, and VK3'CHO. DIVKv5 (polypeptide SEQ ID NO: 12; polynucleotide SEQ ID NO: 80) included the mutations K3Q, F10S, L21I, N22T, L40P, E42K, I58V, V83I, F87Y, and used oligonucleotides VHVK5'CHO, DIVK1, DIVK2, DIVK3, DIVK4, DIVK5A, DIVK6A, DIVK7, DIVK8, DIVK9, DIVK10, and VK3'CHO.

TABLE 6

Oligonucleotides used in the construction of modified ant-CD52 V$_K$s

| Name | Sequence | SEQ ID NO: |
|---|---|---|
| VHVK5'CHO | GCATGTTGACCCTGACGCAAGCTTGCCGCCACCATGGG | 214 |
| DIVK1 | ATGACCCAGTCTCCCTCATCCCTGTCTGCATC | 215 |
| DIVK2 | GAGGGAGACTGGGTCATCTGGATGTCGGAGTGGAC | 216 |
| DIVK3 | CAGAGTCACTATCACCTGCAAAGCAAGTCAGAAT | 217 |

TABLE 6-continued

Oligonucleotides used in the construction of modified ant-CD52 V$_K$s

| Name | Sequence | SEQ ID NO: |
|---|---|---|
| DIVK3A | CAGAGTCACTATCACCTGCAGAGCAAGTCAGAAT | 218 |
| DIVK4 | ATTCTGACTTGCTTTGCAGGTGATAGTGACTCTGT | 219 |
| DIVK4A | ATTCTGACTTGCTCTGCAGGTGATAGTGACTCTGT | 220 |
| DIVK5 | CCCGGAAAAGCTCCCAAACTCCTGATATATAATAC | 221 |
| DIVK5A | CCCGGAAAATCTCCCAAACTCCTGATATATAATAC | 222 |
| DIVK5B | CCCGGAAAAGCTCCCAAATCCTGATATATAATAC | 223 |
| DIVK6 | TTTGGGAGCTTTTCCGGGCTTTTGCTGATACC | 224 |
| DIVK6A | TTTGGGAGATTTTCCGGGCTTTTGCTGATACC | 225 |
| DIVK7 | CGTCCCATCAAGGTTCAGTGGCAGTGG | 226 |
| DIVK8 | GCCACTGAACCTTGATGGGACGCCCGTTTGC | 227 |
| DIVK8A | CACTGAACCTTGATGGGACGCCAGATTGCAAATTG | 228 |
| DIVK9 | GCCTGAAGATATTGCCACATATTACTGCTTGCAGC | 229 |
| DIVK10 | TGCAAGCAGTAATATGTGGCAATATCTTCAGGCTG | 230 |
| VK3'CHO | GCGATAGCTGGACTGAATGGATCCAGTCGACGAAGC | 231 |

The modified V$_H$ and V$_K$ expression cassettes produced were cloned as HindIII to BamHI fragments (DNA and amino acid sequences for DIVHYv1-DIVHv5 are shown in FIG. 3-FIG. 7 and for DIVKv1-DIVKv5 are shown in FIG. 8-FIG. 12 respectively) into the plasmid vector pUC19 and the entire DNA sequence was confirmed to be correct for each modified V$_H$ and V$_K$.

Figure 13:
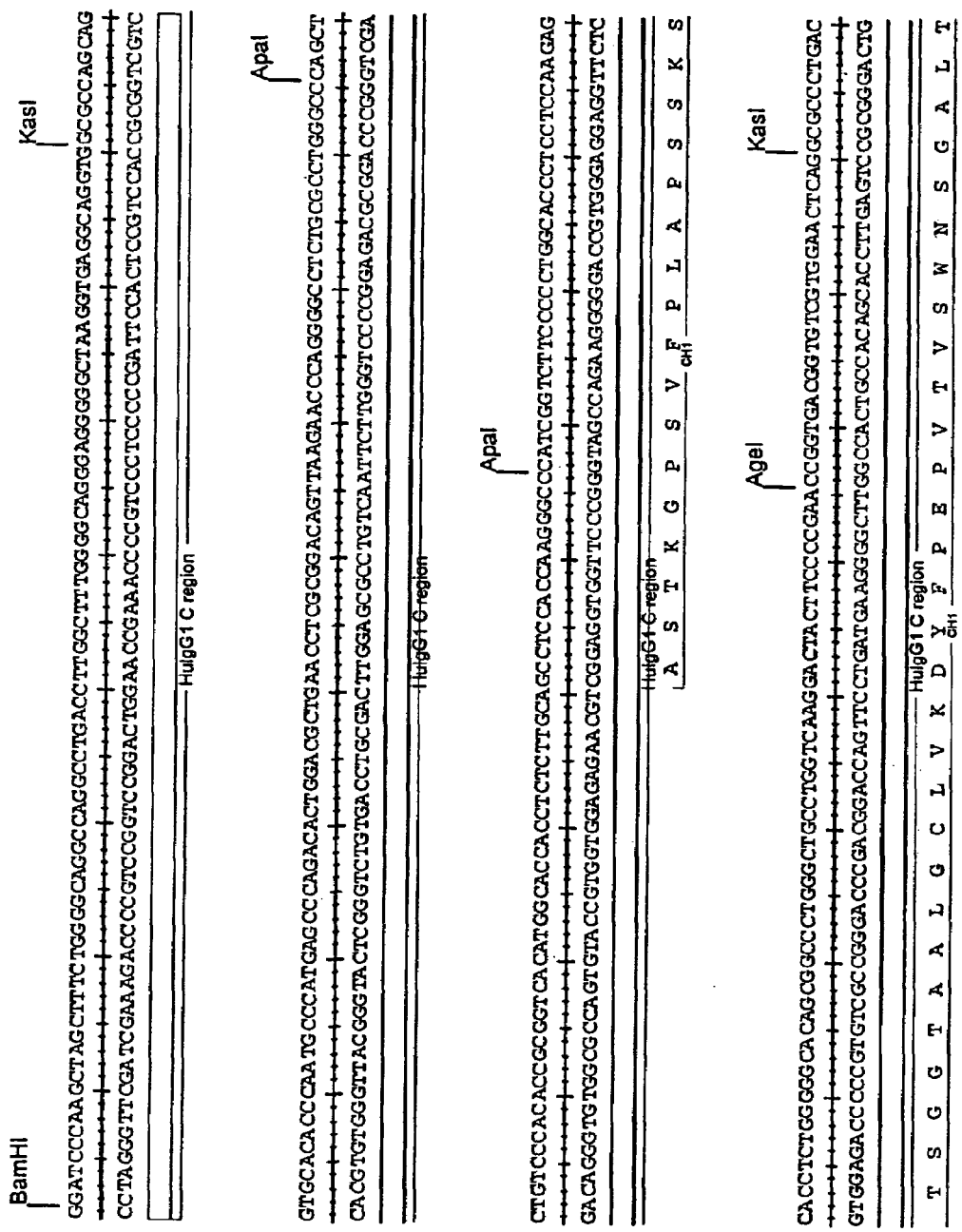
FIG. 13 depicts the DNA and amino acid sequence of human IgG1 constant region (SEQ ID NO:232 and SEQ ID NO:233, respectively).
Figure 13:
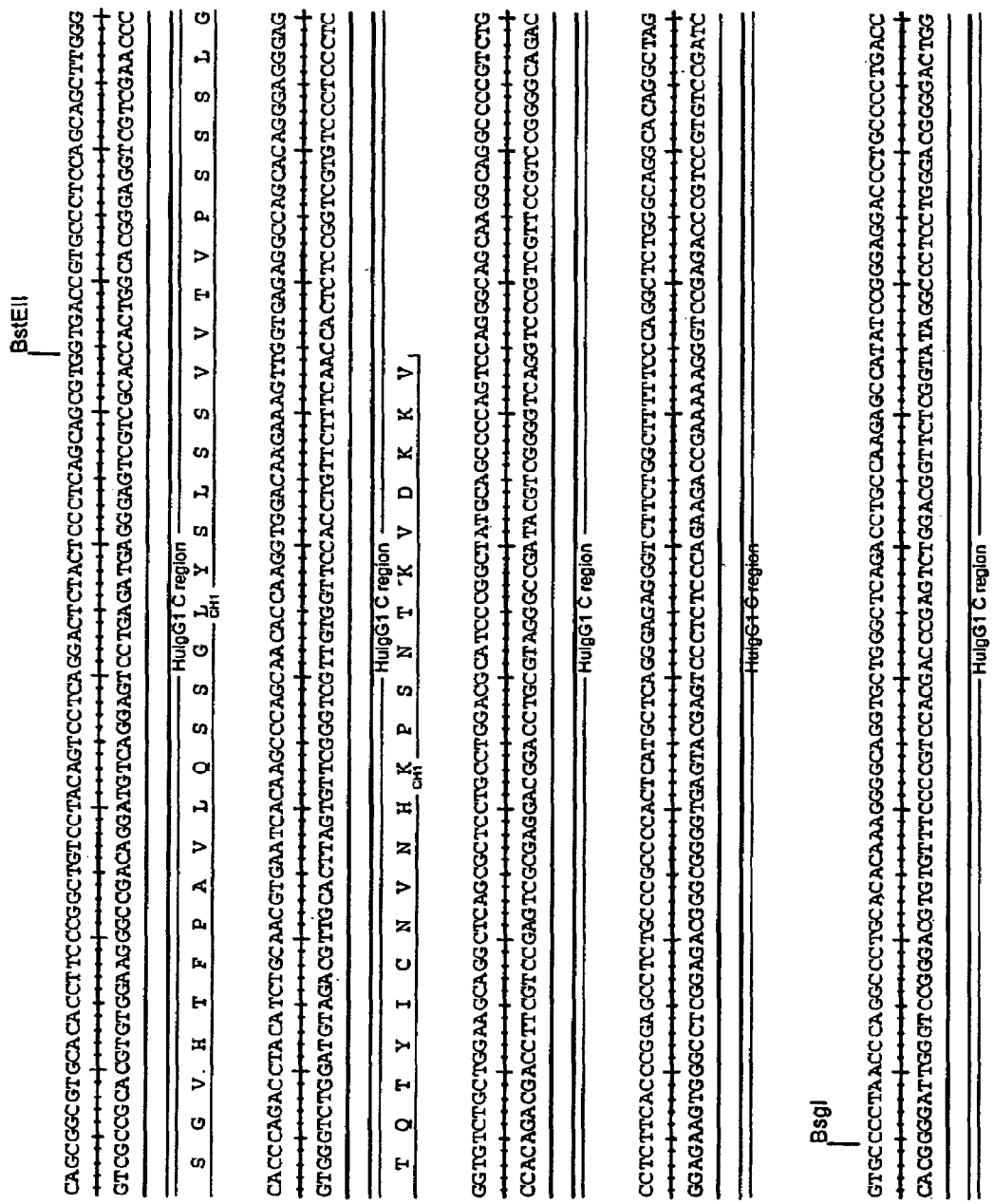
Figure 13:
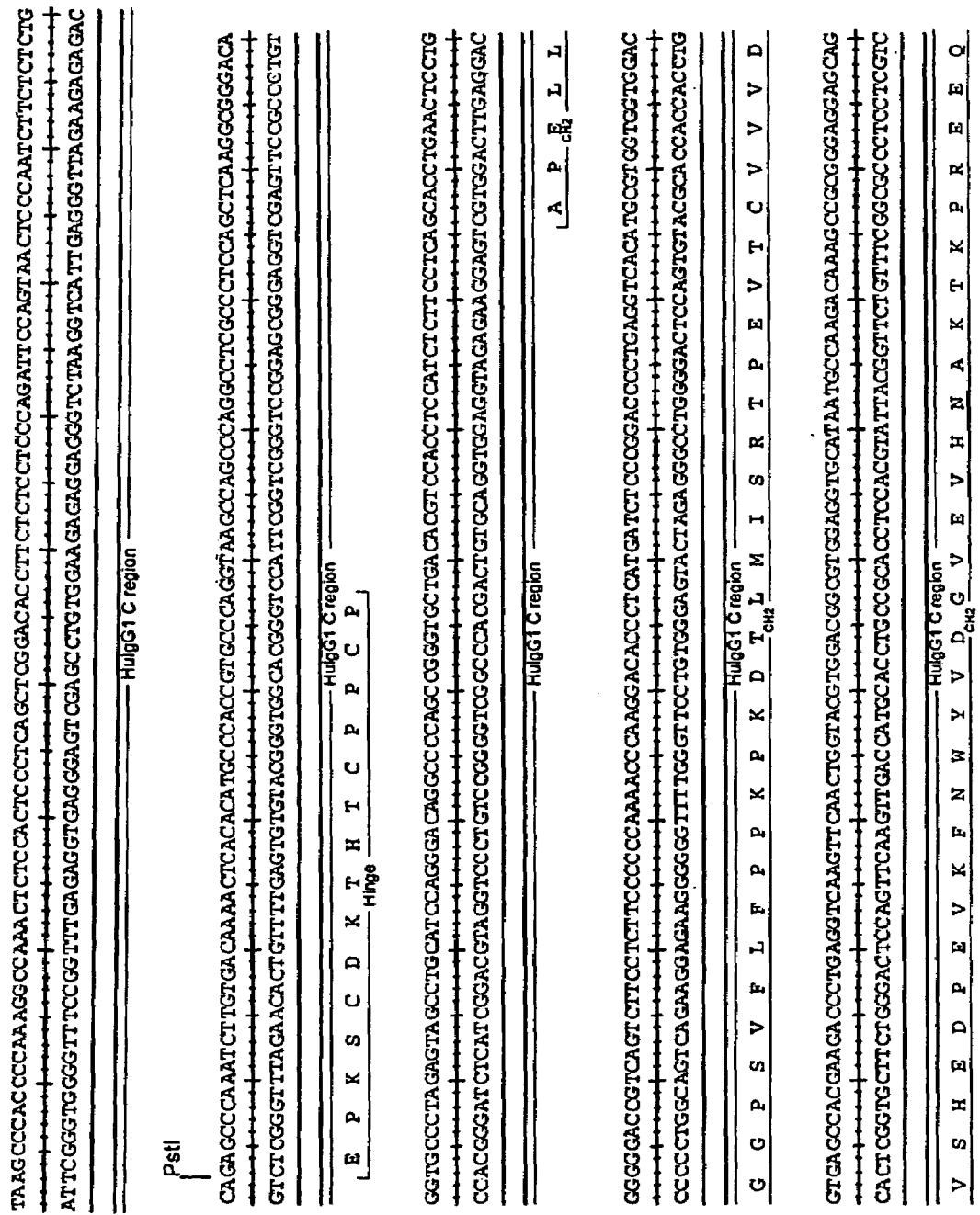
Figure 13:
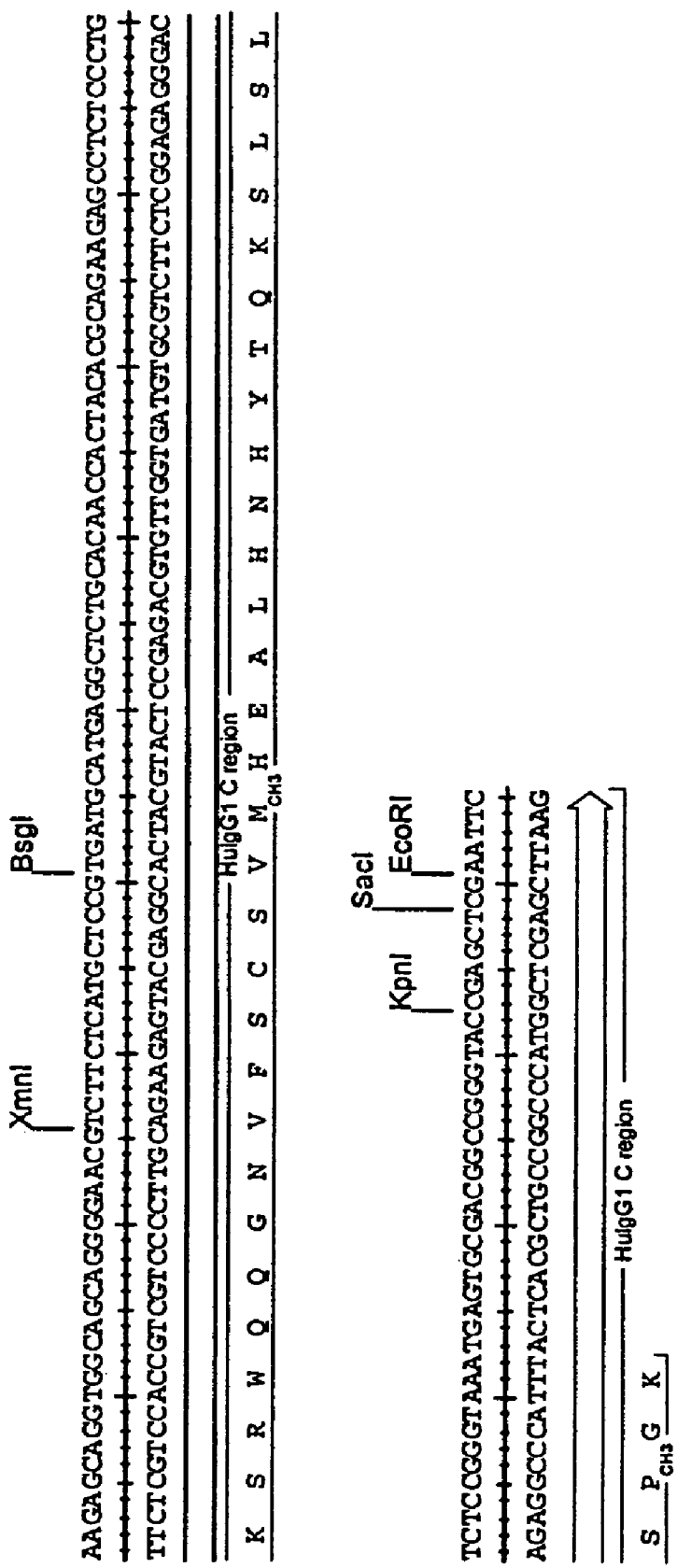
Figure 14:
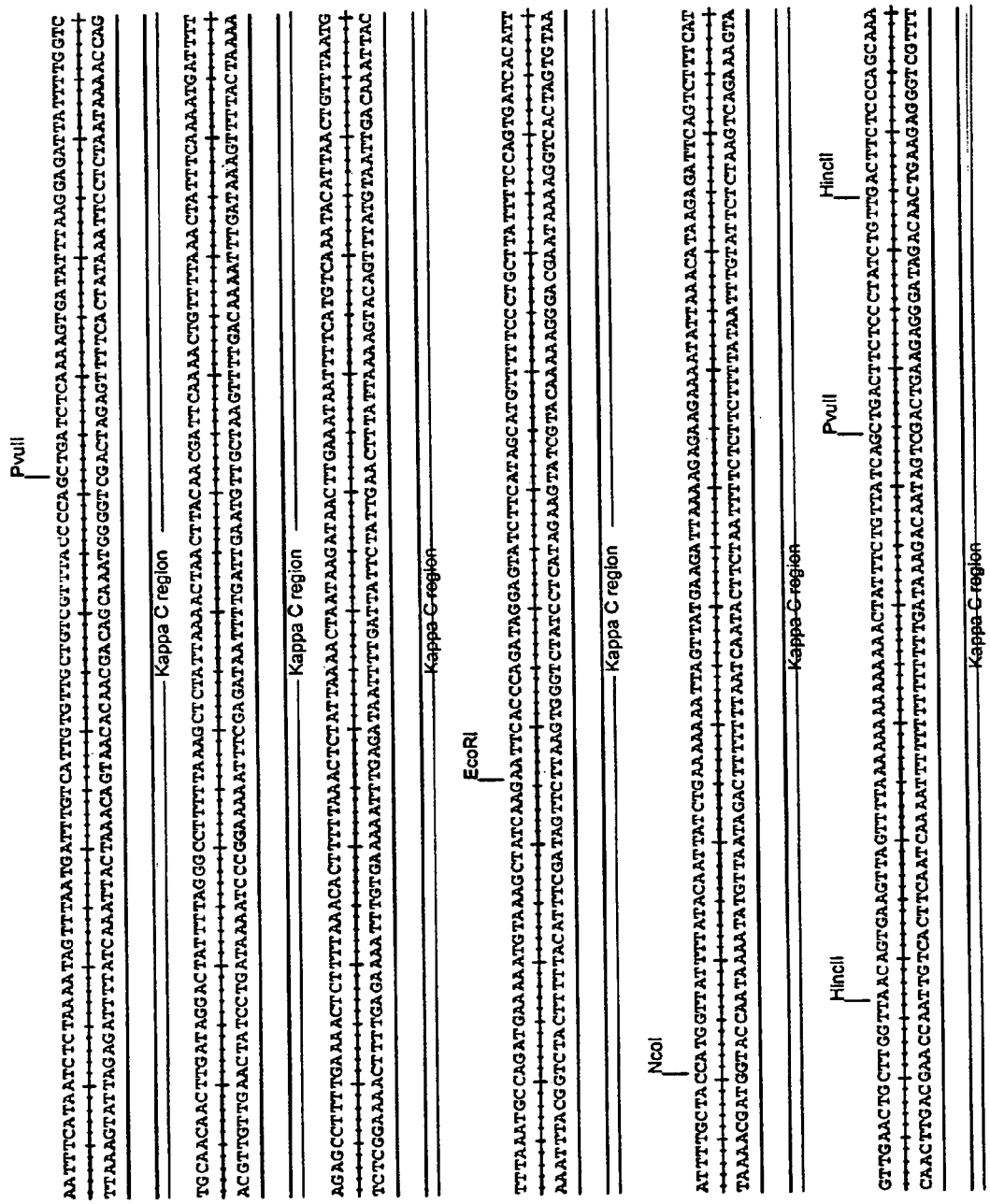
FIG. 14 depicts the DNA and amino acid sequence of human kappa constant region (SEQ ID NO:234 and SEQ ID NO:235, respectively).
Figure 14:
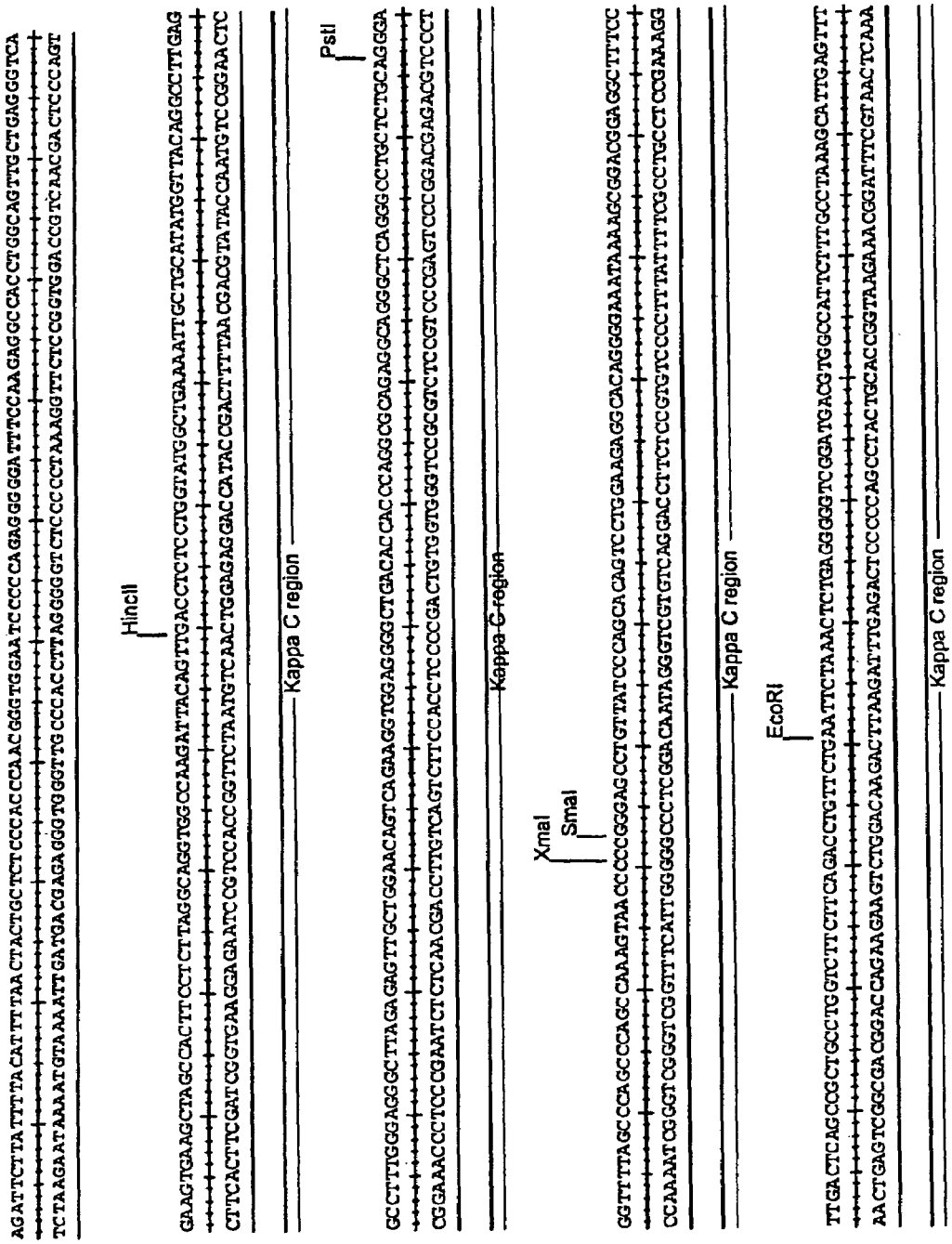
Figure 14:
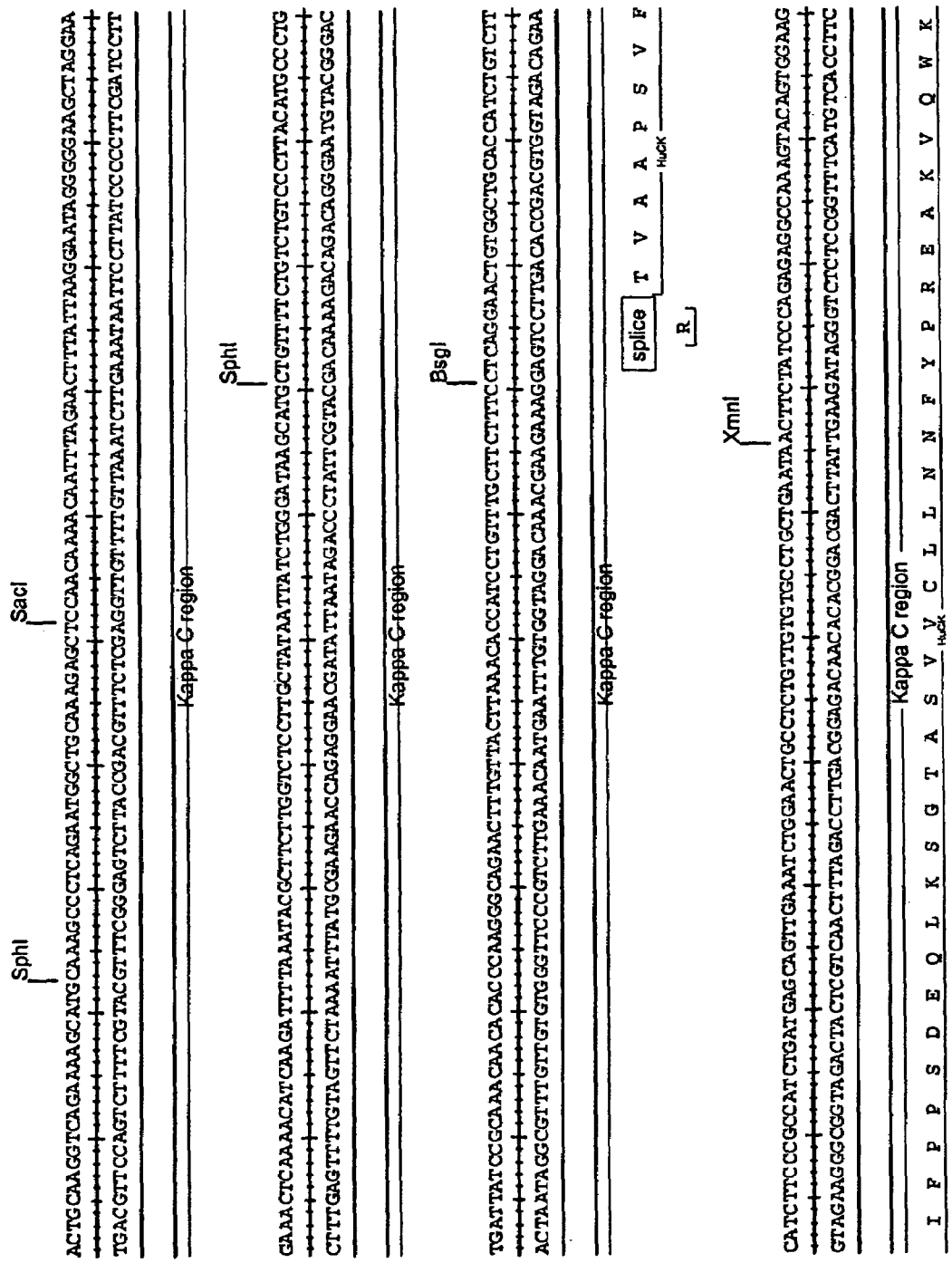
Figure 14:
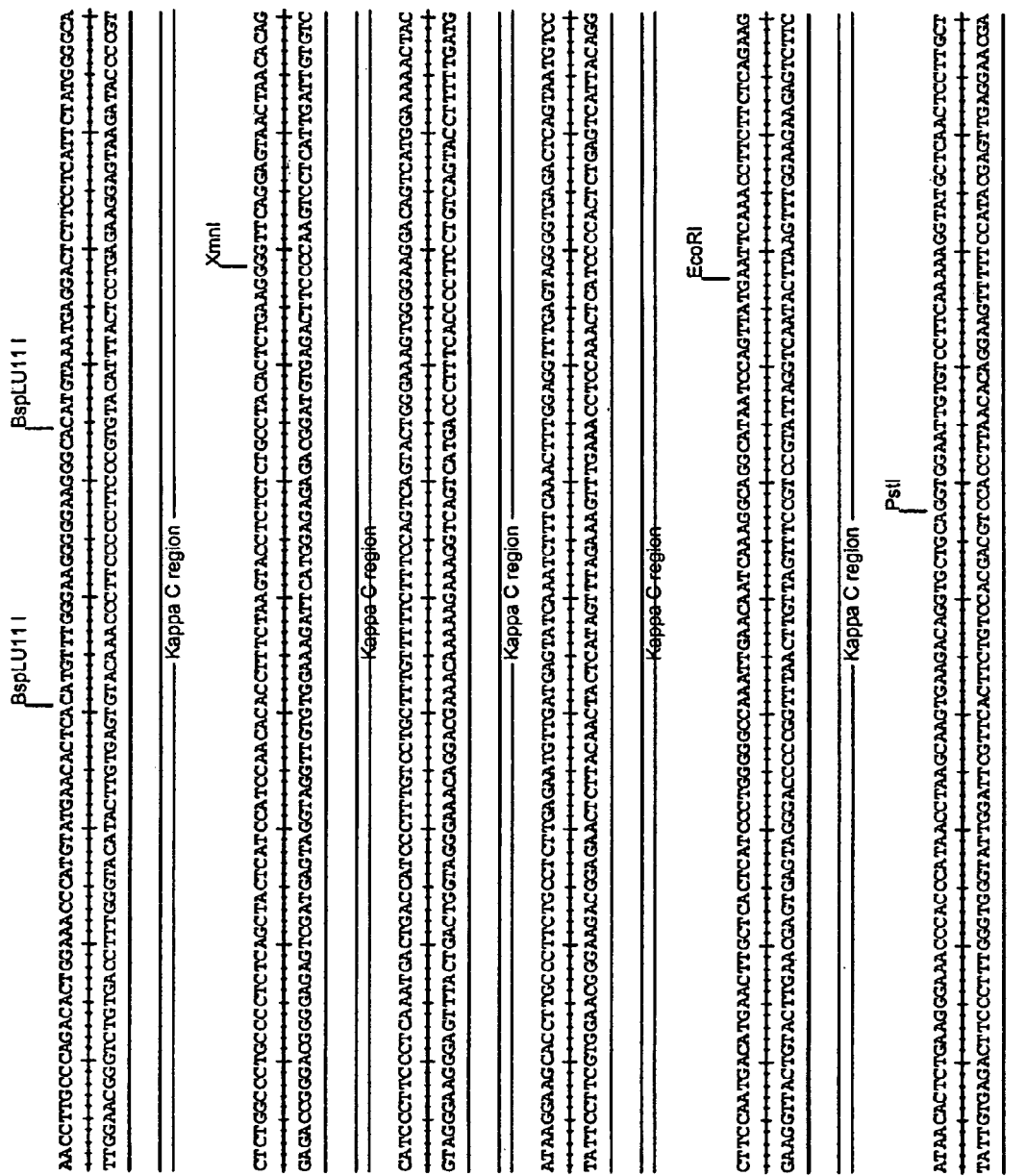
Figure 14:
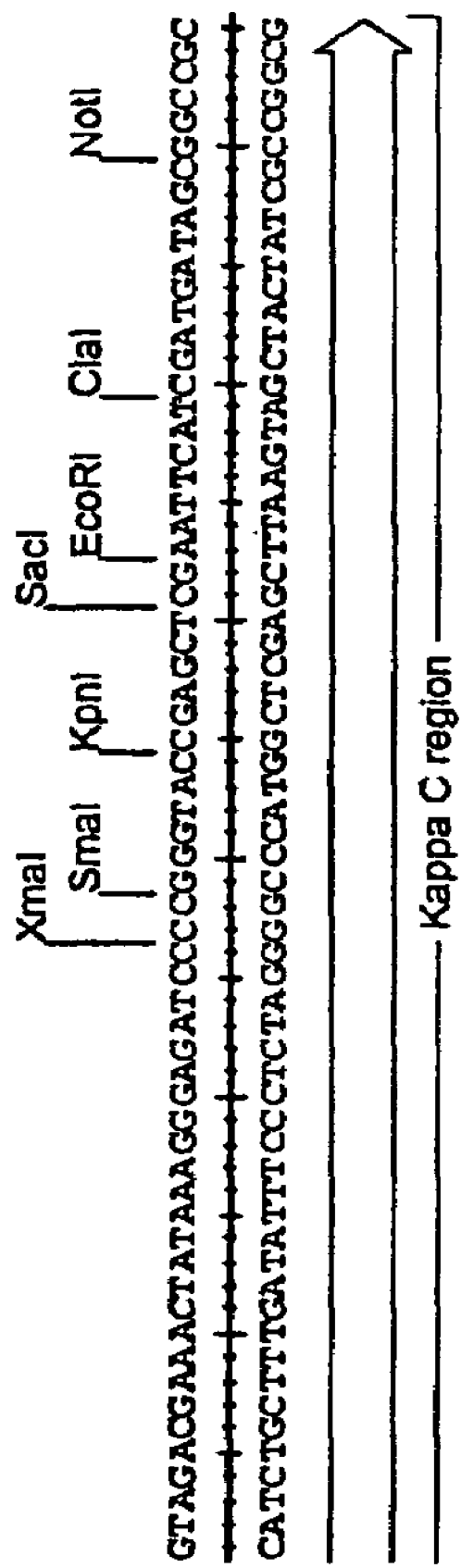

The modified V$_H$ and V$_K$ expression cassettes were linked to human IgG1 (SEQ ID NO: 139; FIG. 13) [Takahashi et al. (1982) Cell 29: 671] and K (SEQ ID NO: 140; FIG. 14) [Heiter et al. (1980) Cell 22: 197] constant regions respectively. These composite antibody genes were then transferred to expression vectors for production of recombinant antibody. The antibody genes are under the control of the human cytomegalovirus immediate early promoter. The heavy chain vector includes the dhfr gene and the light chain vector the neo gene for selection in mammalian cells. The DNA sequence was confirmed to be correct for the V$_H$ and V$_K$ in the expression vectors.

Example 3

Expression, Purification and Quantitation of Anti-CD52 Antibodies

The host cell line for antibody expression was CHO dhFf, obtained from the European Collection of Animal Cell Cultures, Porton UK (ECACC No 94060607). The heavy and light chain expression vectors were co-transfected into CHO cells by electroporation. Colonies expressing the neo and dhfr genes were selected in Iscove's Modified Dulbecco's Medium (IMDM) without nucleosides, supplemented with 10% dialysed foetal bovine serum and 400 μg/ml geneticin (G-418 sulphate) (all from Gibco, Paisley, UK). Transfected cell clones were screened for production of human antibody by ELISA for human IgG [Tempest et al. (1991) BioTechnology 9: 266]. Cell lines secreting antibody were expanded and the highest producers selected and frozen down in liquid nitrogen. The anti-CD52 antibodies were purified using PROSEP®-A (Bioprocessing Ltd) antibody purification kits according to the manufacturer's instructions. The concentration was determined by ELISA for human IgG1 κ antibody.

The assay was conducted in 96-well plates and all determinations were conducted in duplicate. For the assay, plates (Dynatech Immulon 2) were coated using 100 μl per well of sheep anti-human κ antibody (The Binding Site, Birmingham, UK) diluted 1:250 in carbonate/bicarbonate coating buffer pH9.6 (Sigma, Poole, UK). Coating was conducted for 1 hr at 37° C. and the wells washed 3 times with PBST (PBS with 0.05% Tween 20). The wells were filled with 100 μL of PBST and the dilutions for the control and test antibodies set out. The negative control uses PBST only and no antibody was added. The standard antibody (Human IgG1/κ purified myeloma protein, The Binding Site, UK) was diluted to 2 micrograms per ml in PBST. 100 μL was added to duplicate wells in the first column (giving a final concentration of 1 μg/ml) and doubling dilutions made across the plate. Doubling dilution series were also set out for the test antibody preparations. The plate was incubated at room temperature for 1 hr and the wells washed as previously. Bound antibody was detected using a peroxidase conjugated sheep ant-human IgG γ chain specific reagent (The Binding Site, Birmingham, UK). This secondary antibody was diluted 1:1000 in PBST and 100 μl added to each well of the plate. The plate was incubated for a further 1 hour at room temperature and washed as previously. Detection was with o-phenylene diamine (OPD) substrate. One tablet (20 mg) of OPD (Sigma, Poole, UK) was dissolved in 45 ml of peroxidase buffer (Sigma, Poole, UK) with 10 μL 30% (w/w) hydrogen peroxide (Sigma, Poole, UK) added just before use. 100 μL of substrate was added per well and incubated at room temperature for five minutes or as required. Color development was stopped by adding 25 μL of 12.5% H$_2$SO$_4$ and the results at 492 nm. Antibody concentration versus A$_{492}$ was plotted and the concentration of the sample antibody determined by comparison with the standard antibody curve.

Example 4

Testing of Modified Anti-CD52 Antibodies Using a Binding Assay

Human T-cell lymphoma cell line HUT-78 is CD52 positive and was used to assess binding of the modified antibodies of the present invention. In the present example, different concentrations of test antibody were incubated with the cells and the amount of bound antibody was assessed following incubation with a fluorescent-labelled reporter reagent. The reporter is measured using a fluorescence activated cell sorter (FACS).

Briefly, for each assay, $10^6$ HUT-78 cells were incubated with serial dilutions of test antibody and humanised (CAMPATH-1H) and chimaeric anti-CD52 antibodies as controls. The concentrations of the antibodies in ng/ml were: 40000, 20000, 10000, 5000, 2500, 1250, 625, 312.5, 156.25, 78.125, 39.06, 19.53 and 0. All incubations were carried out in a 96 well plate in a final volume of 100 μl PBS/2% FBS.

The antibody and cell mixtures were incubated on ice in the dark for 1 hr and washed twice with 200 µl of cold PBS/2% FBS.

For detection, the cells were incubated for 1 hour on ice with a 1:1000 dilution of FITC-labelled anti-human IgG Fc domain. This reagent is a goat anti-human IgG (Fc specific) obtained from Sigma (Poole, UK). The cells were washed as previously and re-suspended in 100 µl of PBS/2% FBS and transferred to 4 ml FACS tubes (Becton Dickinson) containing 900 µl of PBS/2% FBS/Propidium Iodide (1:1000). The cells were analysed using a conventional Becton Dickenson FACS Calibur instrument.

The binding of the test and control antibodies was determined using the Median Fluorescence value. The saturating concentration of antibody was determined from plots of the Median Fluorescence—Zero Antibody Median Fluorescence versus Concentration of antibody. The binding curves were fitted to a logistic 4 parameter sigmoidal equation using SigmaPlot, giving an excellent fit with 95% confidence levels. The titres, i.e., concentrations at which 50% of maximum binding occurred, are shown in Table 7. The results indicate that many of the antibodies of the present invention show near equivalent binding to the chimeric CAMPATH-1G and the humanized CAMPATH-1H antibodies.

TABLE 7

| Antibody | Titre (µg/ml)(Concentration which gave 50% of maximum binding) |
| --- | --- |
| Humanised CAMPATH-1H | 1.49, 1.44, 2.62, 2.99 |
| Chimaeric CAMPATH-1G | 1.03, 1.99, 2.55, 2.35, 4.20 |
| DIVH1/DIVK1 | 2.99 |
| DIVH1/DIVK2 | 1.66 |
| DIVH1/DIVK3 | 1.71 |
| DIVH1/DIVK4 | 3.45 |
| DIVH1/DIVK5 | 1.85 |
| DIVH2/DIVK1 | 5.56 |
| DIVH2IDIVK2 | 3.70 |
| DIVH2/DIVK3 | 3.89 |
| DIVH2/DIVK4 | 6.21 |
| DIVH2/DIVK5 | 1.18 |
| DIVH3/DIVK1 | 9.60 |
| DIVH3/DIVK2 | 17.79 |
| DIVH3/DIVK3 | >40.0 |
| DIVH3/DIVK4 | 8.63 |
| DIVH3/DIVK5 | 3.30 |
| DIVH4/DIVK1 | 4.43 |
| DIVH4/DIVK2 | 1.59 |
| DIVH4/DIVK3 | 2.28 |
| DIVH4/DIVK4 | 8.54 |
| DIVH4/DIVK5 | 2.39 |
| DIVH5/DIVK1 | 4.01 |
| DIVH5/DIVK2 | 2.45 |
| DIVH5/DIVK3 | 2.55 |
| DIVH5/DIVK4 | 4.05 |
| DIVH5/DIVK5 | 3.00 |

Example 5

Testing of Modified Anti-CD52 Antibodies Using a Competition Assay

Competition binding assays were conducted using the modified antibodies of the present invention. In these assays the test antibodies were assessed for their ability to compete for binding to CD52 against the humanised CAMPATH-1H reagent. In the present example, HUT-78 cells are co-incubated with a sub-saturating amount of a biotinylated CAMPATH-1H and several concentrations of competing non-labelled test antibody. The amount of biotinylated reference antibody bound to the cells was determined following further incubation with an avidin-FITC reporter and fluorescence determination using a FACS instrument as per Example 4.

Briefly, for each competition assay, $10^6$ HUT-78 cells were incubated with 2 µg biotinylated human CAMPATH-1H. Pilot experiments had been previously conducted with the biotinylated CAMPATH-1H and unlabelled CAMPATH-1H to determine the optimum amount of biotinylated antibody required for subsequent to addition to each assay.

Serial dilutions of the test and control antibodies were set out into 96 well plates in a final volume of 100 µl PBS/2% FBS. Test antibodies were set out at 0, 0.1, 0.5, 1.0, 5.0, 10.0, 50.0, 100, 500, & 1000 µg/$10^6$ cells.

The cell and antibody mixtures were incubated on ice in the dark for 1 hour and washed twice with 200 µl of ice-cold PBS/2% FBS. The bound biotinylated antibody was detected by incubation with a 1:200 dilution of an avidin-FITC reagent (Sigma, Poole, UK). Incubation was for 1 hour on ice followed by two cycles of washing as previously. The cells were re-suspended in 100 µl of PBS/2% FBS and transferred to 4 ml tubes containing 900 µl of PBS/2% FBS/Propidium Iodide (diluted 1:1000). The cells were analysed using a Becton Dickenson FACS Calibur instrument.

The binding of the test and control antibodies was expressed as a per-cent inhibition relative to the maximal binding of the biotin labelled control.

The percent inhibition value was determined as below:

$$\%\text{Inhibition} = \frac{[\%\text{ of Gated Cells No Competitor} - \%\text{ of Gated Cells with Competitor}]}{[\%\text{ of Gated Cells No Competitor}]} \times 100$$

The binding curves were fitted to a logistic 4 parameter sigmoidal equation using SigmaPlot, giving an excellent fit with 95% confidence levels. The $EC_{50}$ values were calculated and are shown in Table 8. The results indicate that the antibodies of the present invention bind to CD52 on HUT-78 cells with equivalent efficiency to the chimeric CAMPATH-1G and the humanized CAMPATH-1H antibodies.

TABLE 8

| Antibody | $EC_{50}$ |
| --- | --- |
| Humanised CAMPATH-1H | 1.13, 1.43, 1.00 |
| Chimaeric CAMPATH-1G | 1.00, 2.02, 0.87 |
| DIVH1/DIVK2 | 2.15, 2.84 |
| DIVH1/DIVK3 | 0.93, 2.20 |
| DIVH1/DIVK5 | 1.95, 2.75 |
| DIVH2/DIVK5 | 0.79, 1.04 |
| DIVH4/DIVK2 | 1.25, 2.05 |
| DIVH4/DIVK3 | 2.19, 2.40 |
| DIVH4/DIVK5 | 2.20 |
| DIVH5/DIVK1 | 2.05 |
| DIVH5/DIVK2 | 2.25, 1.65 |
| DIVH5/DIVK3 | 1.97, 1.10 |
| DIVH5/DIVK5 | 1.39, 2.43 |

Example 6

T Cell Immunogenicity Analysis

Modified antibody CAMPATH-1G DIVHv2/DIVKv5, was prepared from the cell line CHO CAMPATH-1G DIVH2/DIVK5 grown in CHO Protein-free Animal Component-Free Medium (Sigma Cat No: G7513) supplemented with L-glutamine and Antibiotic-Antimycotic (Gibco/Invitrogen Cat No: 15240-062). Antibody was purified by PROSEP-A chromatography (Millipore), eluted with 0.1M glycine pH3.0, neutralised and dialysed against phosphate buffered saline (PBS), and finally sterilised by filtration.

Both the DIVH2/DIVK5 modified antibody and humanised CAMPATH control were subjected to a 2-stage purification using cation exchange and size exclusion chromatography. After buffer exchange into 50 mM MES pH6 on a Sephadex G25 (PD10 column), the protein was passed through a cation exchange column (Mono-S 10/10) and eluted with a sodium chloride gradient (0 to 0.5M). The eluted protein containing fractions were then applied to a Superdex 200 preparative column (XK16/60) run in PBS. Peak fractions were pooled and stored at 4° C. The antibody concentrations were determined by ELISA for human IgG.

Experimental: It was suspected that the anti-CD52 CAMPATH antibody would itself be inhibitory to T cells, and would interfere with the analysis of immunogenicity in the standard T cell assay. Preliminary experiments were carried out to test the effect of CAMPATH anti-CD52 antibody on T cells. PBMC were prepared from blood from three healthy normal donors. These were incubated with humanised CAMPATH-1H (supplied by Ilex) alone, Keyhole Limpet Haemocyanin (KLH) alone, KLH and CAMPATH-1H antibody together and untreated control. The results showed that there is a compete inhibition of the response to the control antigen KLH, in all 3 donors, due to the effect of the antibody on the T cells.

In order to analyze the immunogenicity of intact anti-CD52 antibody, a more complex T cell assay protocol was used where dendritic cells (DC) were loaded with whole anti-CD52 antibody and exogenous (non-processed) antigen was removed by washing prior to addition of autologous T cells. In this way, the inhibitory effect of anti-CD52 was avoided and normal responses to KLH achieved. A total of 10 healthy donors were used in this alternative protocol using humanized CAMPATH-1H as a test control antigen.

Briefly, PBMC were used as a source of monocytes, which were isolated by adherence to tissue culture plastic (>90% CD14$^+$). Monocytes were cultured in AIM V medium (Gibco) with 3% heat inactivated human AB serum (Autogen Bioclear) (growth medium) at an approximate density of 1×10$^6$ per well (24-well plate). To induce an APC-like phenotype (CD40$^+$, CD80$^{hi}$, CD83$^{hi}$, CD86$^{hi}$, MHC class II$^{hi}$) monocytes were incubated in growth medium containing human IL-4 (Peprotech) and GM-CSF (Peprotech) for 4 days. On day 4, 50 µg/ml of test antigen (humanised CAMPATH-1H or modified CAMPATH-1G DIVHv2/DIVKv5 antibody) was added. Control wells received medium only. After 24 hrs the growth medium and antigen was removed and the cells washed once before adding fresh growth medium containing TNFα (Peprotech), GM-CSF and IL-4 for 4 days. Then both adherent and non-adherent dendritic cells (DCs) were harvested and counted. The DCs were distributed at 1×10$^4$ per well of 96 well round bottom plates, in sextuplicate cultures per treatment (humanised CAMPATH-1H or modified CAMPATH-1G DIVHv2/DIVKv5 antibody or control) per donor. The DC were gamma irradiated with 4000 rads before adding autologous CD4$^+$ T cells that were negatively isolated from PBMC (Dynal Human CD4$^+$ Negative Isolation Kit) at 1×10$^5$ per well. Plates were incubated for 7 days and proliferation was measured by incorporation of tritiated thymidine (a 6-hr pulse with $^3$H-Thymidine at 1 µCi/well). These data are expressed as a stimulation index where:

$$\text{Stimulation Index} = \frac{CPM \text{ of test antigen}}{CPM \text{ of untreated control}}$$

Figure 15:
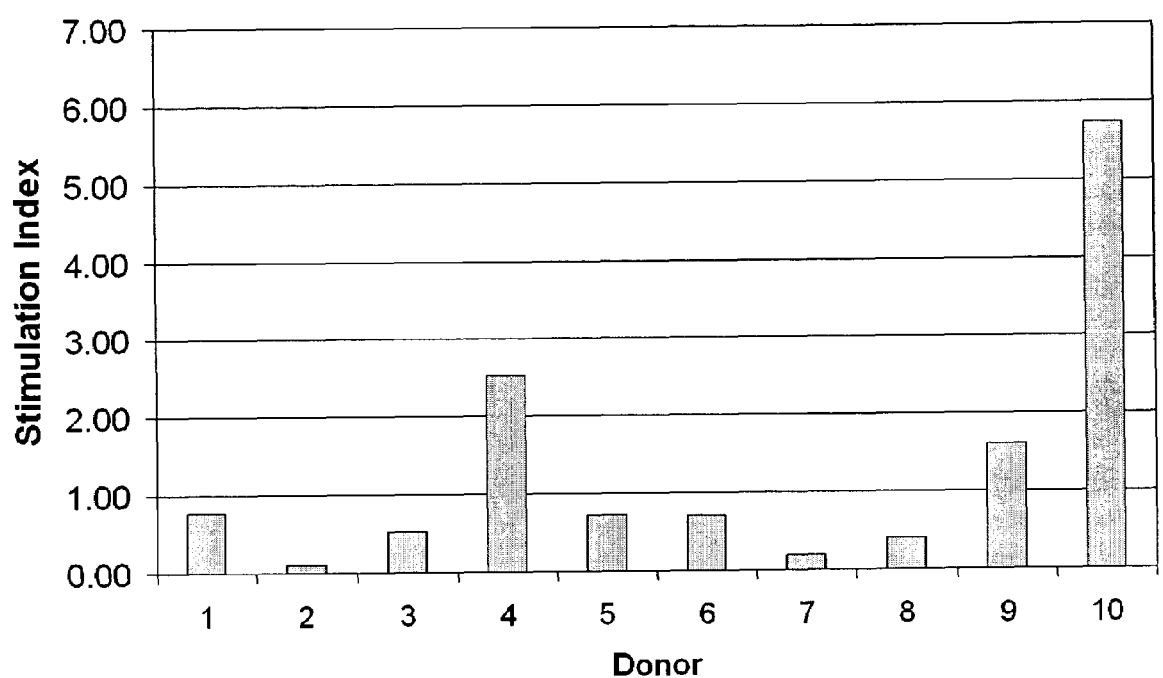
FIG. 15 summarizes the results of the preliminary studies using the alternative dendritic cell:T cell protocol with the modified DIVHv5/DIVKv2 antibody.

A positive result is defined as a stimulation index (SI) greater than 2. Preliminary results (FIG. 15) show that 2 out of 10 these donors responded to CAMPATH-1H, one with a very high stimulation index.

Comparison of CAMPATH-1H and modified DIVHv5/DIVKv2 antibody: A panel of twenty healthy donors were selected based on HLA-DR typing (see Table 9) for screening the humanised and modified antibodies in T cell assays. This enabled the screening of the antibodies against greater than 80% of DR alleles expressed in the world population.

TABLE 9

HLA DR haplotypes of the set of 20 healthy donors used to test the immunogenicity of humanised and modified CAMPATH antibodies

| DONOR | Allotype |
|---|---|
| 1 | DRB1*04, DRB4*01 |
| 2 | DRB1*03, DRB1*04, DRB4*01, DRB5 |
| 3 | DRB1*01, DRB1*13, DRB3 |
| 4 | DRB1*01, DRB1*07, DRB4*01 |
| 5 | DRB1*11 AND DRB1*13 OR 14, DRB3 |
| 6 | DRB1*03 AND DRB1*08, 11 OR 13, DRB3 |
| 7 | DRB1*01, DRB1*11, DRB3 |
| 8 | DRB1*10, DRB1*15, DRB5 |
| 9 | DRB1*04, DRb1*15, DRB4*01, DRB5 |
| 10 | DRB1*03, DRB1*15, DRB3, DRB5 |
| 11 | DRB1*13, DRB1*16, DRB3, DRB5 |
| 12 | DRB1*03, DRB1*07, DRB3, DRB4 |
| 13 | DRB1*03, DRB1*10, DRB3 |
| 14 | DRB1*04, DRB1*09, DRB4*01 |
| 15 | DRB1*09, DRB1*15, DRB4*01, DRB5 |
| 16 | DRB1*03, DRB1*08, DRB3 |
| 17 | DRB1*08, DRB1*15, DRB5 |
| 18 | DRB1*13 & DRB1*14 OR DRB13, DRB3 |
| 19 | DRB1*07, DRB4*01 |
| 20 | DRB1*07, DRB1*16, DRB4*01, DRB5 |

Figure 16:
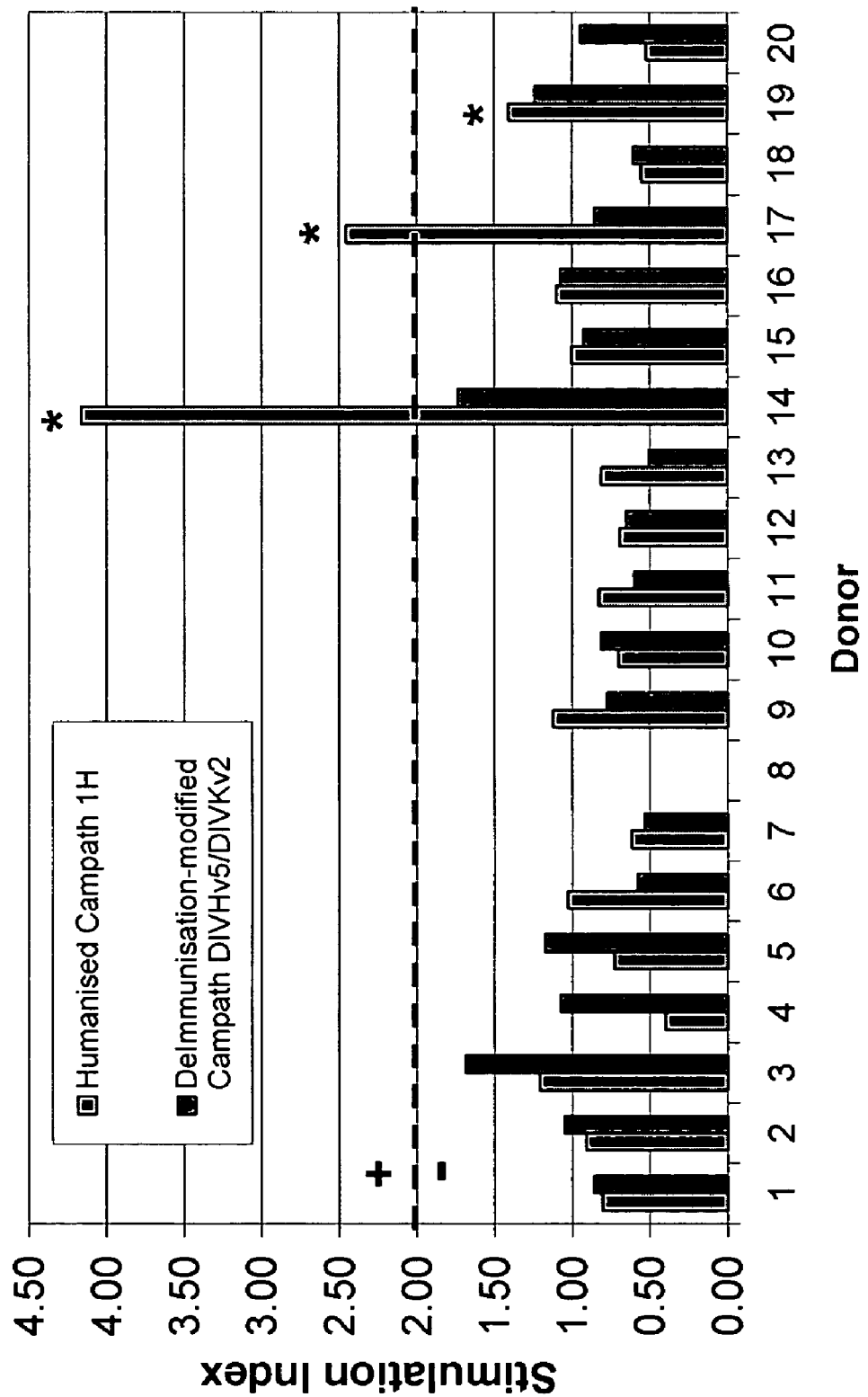
FIG. 16 summarizes the comparison of T cell immunogenicity (dendritic cell:T cell assay) of humanised CAMPATH 1H and the modified DIVKv5/DIVKv2 antibody. Cpm values were compared (*) against untreated controls using Students T-Test ($p<0.05$).

FIG. 16 shows that humanised CAMPATH 1H induced significant (p<0.05) proliferative responses (cpm compared to untreated controls) in three healthy individuals (donors 14, 17 and 19). However only T cells from donors 14 and 17 produced sufficiently high (SI>2) stimulation indexes of 4.2 and 2.5, respectively. The donor 19 response was excluded since the stimulation index was considerably lower (SI~1.5) than the threshold set for this experiment. For Donor 8 the untreated control produced less than 400 cpm and was therefore excluded from the study. Importantly, none of the donors responded to the modified DIVHv5/DIVKv2 antibody.

Thus, the humanised CAMPATH 1H antibody has the potential to induce a T cell dependent humoral immune response (marked by affinity matured, isotype switched anti-CAMPATH 1H antibodies) in some human patients with certain MHC Class II allotypes. This observation was supported by ex vivo T cell assays in which T cell activation occurred in at least two healthy individuals (donors 14 and 17) in response to treatment with antigen processed CAMPATH 1H (expressed by matured DC). Comparison of ex vivo T cell responses using antigen processed modified DIVHv5/DIVKv2 antibody showed that this completely failed to induce T cell proliferation in any of the donors tested. These data demonstrate that the modified antibody is likely to provide an improved therapeutic molecule when substituted for humanised CAMPATH-1H, particularly when used for indications where repeated dosing is required.

---

We claim:

1. An expression vector comprising a nucleic acid sequence coding for SEQ ID NO: 72.

2. An expression vector comprising a nucleic acid sequence coding for SEQ ID NO: 80.

* * * * *